(12) United States Patent
Boyle, Jr. et al.

(10) Patent No.: US 11,103,272 B2
(45) Date of Patent: Aug. 31, 2021

(54) MINIMALLY INVASIVE METHODS AND APPARATUS FOR TARGET-TISSUE EXCISION

(71) Applicant: PRECISION THORACIC, LLC, Orange, CA (US)

(72) Inventors: Edward M. Boyle, Jr., Bend, OR (US); Kenneth Allan Beres, Burbank, CA (US); Richard Fischel, Orange, CA (US)

(73) Assignee: PRECISION THORACIC, LLC, Irvine, CA (US)

( * ) Notice: Subject to any disclaimer, the term of this patent is extended or adjusted under 35 U.S.C. 154(b) by 333 days.

(21) Appl. No.: 16/205,309

(22) Filed: Nov. 30, 2018

(65) Prior Publication Data

US 2019/0099197 A1 Apr. 4, 2019

Related U.S. Application Data

(63) Continuation of application No. 15/767,934, filed as application No. PCT/US2018/016685 on Feb. 2, 2018.

(Continued)

(51) Int. Cl.
*A61B 17/32* (2006.01)
*A61B 17/3205* (2006.01)
(Continued)

(52) U.S. Cl.
CPC .... *A61B 17/32053* (2013.01); *A61B 10/0266* (2013.01); *A61B 10/04* (2013.01);
(Continued)

(58) Field of Classification Search
CPC .... A61B 17/32053; A61B 2017/00809; A61B 2017/306; A61B 2017/320064;
(Continued)

(56) References Cited

U.S. PATENT DOCUMENTS 4,007,732 A 2/1977 Kvavle et al.
5,190,561 A 3/1993 Graber
(Continued)

FOREIGN PATENT DOCUMENTS

WO 199603163 A1 2/1996
WO 2005110508 A2 11/2005
WO 2007014313 A2 2/2007

OTHER PUBLICATIONS

International Search Report & Written Opinion issued in corresponding PCT application No. PCT/US2018/016685 dated May 23, 2018, 18 pages.

(Continued)

*Primary Examiner* — Erich G Herbermann
*Assistant Examiner* — Chima U Igboko
(74) *Attorney, Agent, or Firm* — Pearne & Gordon LLP

(57) ABSTRACT

Methods and apparatus are provided to facilitate the minimally invasive removal of tissue and to facilitate the direct approach to anesthetizing a body wall of a patient. A pull-type cutting device also is disclosed to introduce an opening into the body wall to provide access for intra-chest surgical interventions, for example a minimally invasive biopsy technique as also described for excising target tissue from within a patient, including a nodule from within the patient's lung.

18 Claims, 42 Drawing Sheets

Related U.S. Application Data

(60) Provisional application No. 62/453,672, filed on Feb. 2, 2017, provisional application No. 62/463,312, filed on Feb. 24, 2017.

(51) Int. Cl.

| | | |
|---|---|---|
| *A61B 10/02* | (2006.01) | |
| *A61B 10/04* | (2006.01) | |
| *A61B 17/00* | (2006.01) | |
| *A61B 18/14* | (2006.01) | |
| *A61B 17/3207* | (2006.01) | |
| *A61B 17/22* | (2006.01) | |
| *A61B 17/34* | (2006.01) | |
| *A61B 90/00* | (2016.01) | |
| *A61B 17/30* | (2006.01) | |
| *A61M 25/10* | (2013.01) | |
| *A61B 18/00* | (2006.01) | |
| *A61B 17/3209* | (2006.01) | |
| *A61B 17/06* | (2006.01) | |
| *A61B 17/221* | (2006.01) | |
| *A61B 10/00* | (2006.01) | |

(52) U.S. Cl.
CPC .... *A61B 17/0057* (2013.01); *A61B 17/00491* (2013.01); *A61B 17/320016* (2013.01); *A61B 17/32056* (2013.01); *A61B 17/320725* (2013.01); *A61B 18/1477* (2013.01); *A61B 10/0283* (2013.01); *A61B 17/221* (2013.01); *A61B 17/32075* (2013.01); *A61B 17/32093* (2013.01); *A61B 17/3423* (2013.01); *A61B 18/14* (2013.01); *A61B 2010/0006* (2013.01); *A61B 2017/005* (2013.01); *A61B 2017/0065* (2013.01); *A61B 2017/00349* (2013.01); *A61B 2017/00508* (2013.01); *A61B 2017/00606* (2013.01); *A61B 2017/00654* (2013.01); *A61B 2017/00659* (2013.01); *A61B 2017/00663* (2013.01); *A61B 2017/00809* (2013.01); *A61B 2017/06171* (2013.01); *A61B 2017/22034* (2013.01); *A61B 2017/22038* (2013.01); *A61B 2017/22061* (2013.01); *A61B 2017/306* (2013.01); *A61B 2017/320056* (2013.01); *A61B 2017/320064* (2013.01); *A61B 2018/00291* (2013.01); *A61B 2018/00392* (2013.01); *A61B 2018/00601* (2013.01); *A61B 2090/3908* (2016.02); *A61M 2025/105* (2013.01); *A61M 2025/1013* (2013.01); *A61M 2025/1086* (2013.01)

(58) Field of Classification Search
CPC ........ A61B 2017/320056; A61B 10/02; A61B 10/0233; A61B 10/0266; A61B 10/06; A61B 2010/0208; A61B 2090/3908; A61B 2017/0065; A61B 2017/22061; A61B 2017/00508; A61B 2017/06171; A61B 2017/0809; A61B 2017/00349; A61B 2017/00606; A61B 2017/22034; A61B 2017/22038; A61B 2017/00663; A61B 2017/005; A61B 2017/00654; A61B 2017/00659; A61B 2018/00601; A61B 2018/00291; A61B 2018/00392; A61B 17/32093; A61B 17/221; A61B 17/32075; A61B 17/320725; A61B 17/00491; A61B 17/0057; A61B 17/320016; A61B 17/32056; A61B 17/3423; A61B 2010/0006; A61B 10/0283; A61B 10/04; A61B 18/14; A61B 18/1477; A61M 2025/1086; A61M 2025/1013; A61M 2025/105

See application file for complete search history.

(56) References Cited

U.S. PATENT DOCUMENTS

| | | |
|---|---|---|
| 5,196,024 A | 3/1993 | Barath |
| 5,353,804 A | 10/1994 | Kornberg et al. |
| 5,643,282 A | 7/1997 | Kieturakis |
| 5,681,281 A | 10/1997 | Vigil et al. |
| 5,779,698 A | 7/1998 | Clayman et al. |
| 5,908,435 A | 6/1999 | Samuels |
| 5,961,526 A | 10/1999 | Chu et al. |
| 6,213,957 B1 | 4/2001 | Milliman et al. |
| 6,258,108 B1 | 7/2001 | Lary |
| 6,652,520 B2 | 11/2003 | Moorman et al. |
| 6,770,070 B1 | 8/2004 | Balbierz |
| 7,517,352 B2 | 4/2009 | Evans et al. |
| 7,811,303 B2 | 10/2010 | Fallin et al. |
| 8,602,973 B2* | 12/2013 | Wendlandt ......... A61B 1/00147 600/114 |
| 8,734,362 B2 | 5/2014 | Boyle, Jr. |
| 2002/0019597 A1 | 2/2002 | Dubrul et al. |
| 2002/0082614 A1 | 6/2002 | Logan et al. |
| 2002/0095101 A1 | 7/2002 | Fontenot |
| 2006/0025815 A1 | 2/2006 | McGurk et al. |
| 2006/0074484 A1 | 4/2006 | Huber |
| 2007/0073343 A1 | 3/2007 | Jahns et al. |
| 2009/0054805 A1* | 2/2009 | Boyle, Jr. ...... A61B 17/320016 600/564 |
| 2009/0105745 A1* | 4/2009 | Culbert .............. A61B 17/3439 606/192 |
| 2010/0036312 A1 | 2/2010 | Krolik et al. |
| 2012/0316608 A1 | 12/2012 | Foley |
| 2013/0150701 A1* | 6/2013 | Budar .................... A61B 10/04 600/407 |
| 2014/0276009 A1 | 9/2014 | Boyle, Jr. |
| 2015/0342638 A1* | 12/2015 | Smith ................ A61B 17/3423 600/204 |
| 2017/0042516 A1 | 2/2017 | Boyle, Jr. |

OTHER PUBLICATIONS

Supplemental European Search Report issued in corresponding application No. EP18748579 dated Oct. 22, 2020, 7 pages.

\* cited by examiner

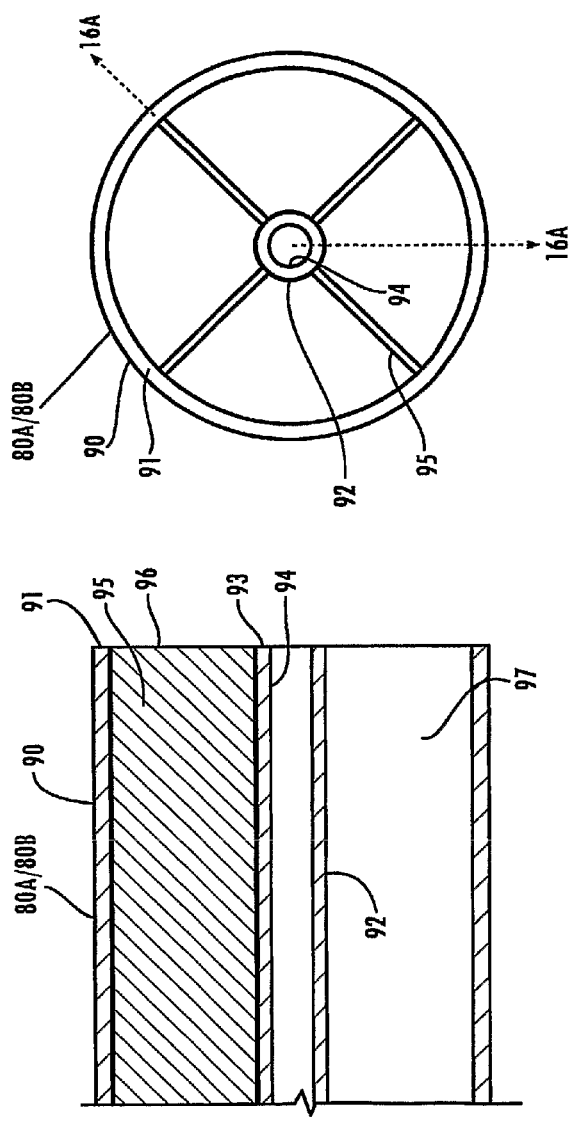

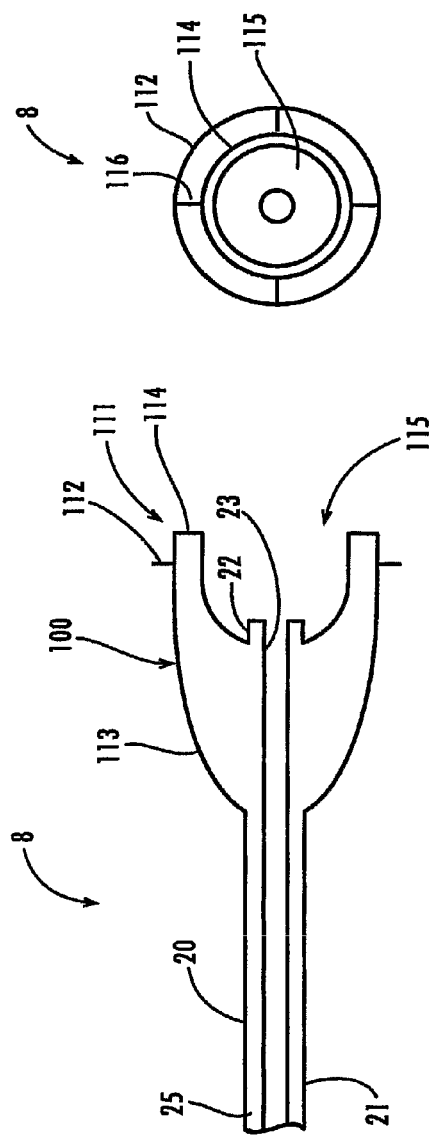

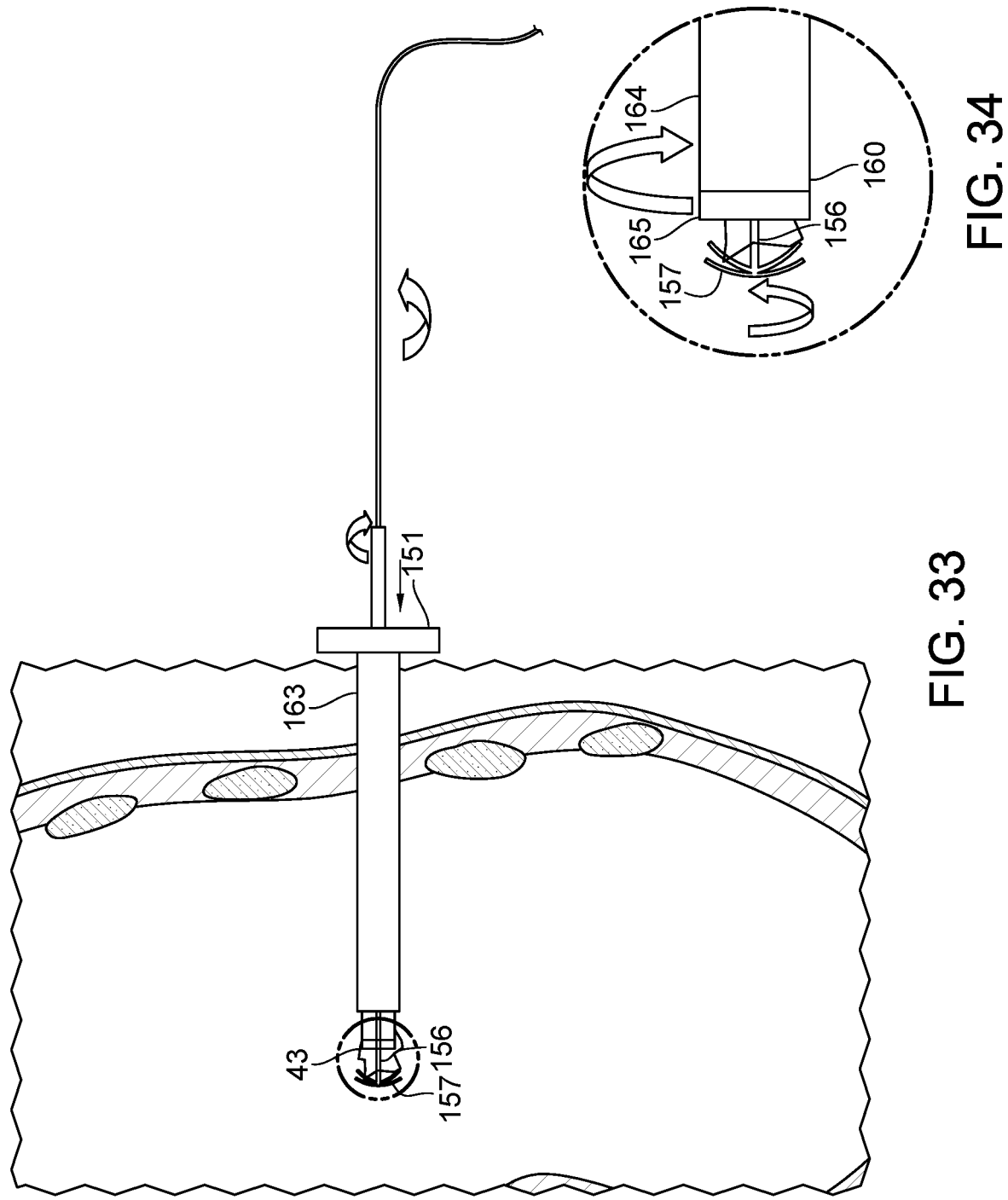

MINIMALLY INVASIVE METHODS AND APPARATUS FOR TARGET-TISSUE EXCISION

RELATED APPLICATION

This application is a continuation of U.S. patent application Ser. No. 15/767,934 filed on Apr. 12, 2018, which is the US national stage of PCT/US2018/016685 filed Feb. 2, 2018, which claims the benefit of Provisional applications Nos. 62/453,672 filed on Feb. 2, 2017 and 62/463,312 filed on Feb. 24, 2017, all of which are in their entirety incorporated herein by reference.

FIELD OF THE INVENTION

The present invention is related to surgical tools and methods.

BACKGROUND

According to the American Lung Association, each year over 344,000 Americans die of lung disease, making it the third most frequent cause of death in this country. An even more staggering statistic is that an additional 35 million Americans are living with chronic, debilitating lung diseases. Not uncommonly, patients with lung disease or at risk for lung disease undergo various forms of thoracic imaging. This has led to an unprecedented number of patients presenting to lung specialists with nodular abnormalities suspicious for cancer or interstitial abnormalities suspicious for various forms of Interstitial Lung Disease (ILD). When a patient is found with these abnormalities, it is often necessary to biopsy the tissue to establish the diagnosis, the prognosis, and guide further therapy.

One of the factors that contribute to lung disease is smoking. According to the Center for Disease Control, there are 94 million past and current smokers in the US. Half are over the age of 45 (the age at which lung cancer incidences increase). Many smokers are concerned about the risk of developing lung cancer, which explains the growing success of CT based lung cancer screening programs. The problem with these programs is that about 30% of the screened patients will have suspicious nodules suggestive of cancer, but only a small percentage are ultimately proven to be cancer. While there is considerable evidence to suggest that CT based lung cancer early detection programs are beneficial in detecting early stage lung cancer, the area of biggest clinical unmet need is in the ability to differentiate between a benign and malignant nodule. The currently available lung biopsy techniques, such as CT guided biopsy, bronchoscopy, thoracoscopy or thoracotomy are either too insensitive or too invasive, limiting their usefulness and making the determination difficult at best. Thus one of the most significantly limiting factors that has prevented success of lung cancer screening programs has been a lack of safe and effective ways to sample lung tissue in a minimally invasive fashion.

A similar dilemma exists for the diagnosis of interstitial lung disease. In a number of cases where there is a suspicious imaging pattern suggestive of ILD or cancer, it is desirable to sample the tissue so that a pathologist can establish the exact cause of the abnormality. The problem is that the current lung biopsy techniques are invasive, painful and many require general anesthesia, which is not always well tolerated in patients with impaired lung function. Many patients are judged "not a surgical candidate," due to the patient's degree of medical disability and lung dysfunction. Both thoracotomy (a large incision through the chest muscles and between the ribs) and thoracoscopy (the use of a scope and other working ports through the ribs to operate in the space around the lung) can be very disabling and painful. In fact, these forms of surgery are generally much more painful and disabling than other forms of surgery, such as heart surgery and abdominal surgery due to the manipulation of the chest wall muscles, ribs and intercostal nerves between the ribs. Currently, thoracotomy and thoracoscopy often require long hospital stays and even longer recovery times. Both procedures can lead to chronic pain syndromes in a surprisingly high percentage of patients.

When a determination is made to biopsy a lung nodule 510, there are several options, as illustrated in FIG. 1. One option is to use a bronchoscopic approach. This, however, is most useful for larger, more central tumors. Generally, a central approach is not a useful option for the more common small nodules since most lung nodules 510 are in the periphery 501 of the lung 502 and not connected to the airway 503. Another option is to use a CT guided needle biopsy 522 of the lung 502. While this approach can be useful in larger, more peripheral tumors, it is not particularly helpful for smaller nodules 510 that are deeper in the lung 502. Furthermore, only a small core sampling of the tissue can be taken, and thus false negative biopsies are common. Additionally, since there is no mechanism to seal the lung 502, bleeding complications and pneumothorax are frequent concerns, occurring in nearly 20% of patients.

Thoracic surgical approaches to biopsy lung nodules can be divided into two categories: thoracotomy and thoracoscopy. A thoracotomy 530 is a 300 to 450 mm (12 to 18 inches) incision 532 on the chest wall skin 304, followed by division or dissection of the major back muscles to move them out of the way, partial removal of the rib 42, and the placement of a rib spreader 534 to provide intra thoracic access to the operating surgeon. The advantage of a thoracotomy is that the surgeon has excellent access to the intrathoracic structures, and can see and manually feel the lung 502 and other structures directly. This is especially important when targeting a tiny lung nodule 510. The major disadvantage is the degree of pain and the potential for complications related to the magnitude of the incision. A thoracotomy is well known to be a very painful operation for the patient, with significant acute and chronic pain issues. Because of the degree of invasiveness, it is reserved only for the most optimal surgical candidates as many patients with significant lung disease cannot tolerate a thoracotomy and recover without significant morbidity and mortality. For these reasons it is recognized that there is a need in the art to lessen the invasiveness of thoracic surgery.

One approach that has been around for many years is to utilize an endoscope 542 to facilitate visualization within in the chest, thereby precluding the need for a large thoracotomy incision. Thoracoscopy 540 is the use of a specialized viewing instrument, usually a rigid endoscope 542, introduced through a thoracostomy, or a small hole placed in between the ribs 42. Once the endoscope 542 is placed in the space that surrounds the lung 502, known as the pleural space, usually two to three additional thoracostomy holes are made to introduce additional instruments 544. Additional instruments 544 include grasping instruments, cutting instruments, and in the case of a thoracoscopic lung biopsy, a cutting stapler, such as the Ethicon Endosurgery Endo GIA 45 mm stapler. Using the endoscope 542 and the other instruments 544, a "triangulation" technique is utilized where, for example, the endoscope 542 is used to view as the grasping instrument is brought in from one direction, and the stapler is brought in from another, and tissue is cut with the stapler and removed through one of the ports.

One of the major disadvantages of this approach is the number and size of ports needed to triangulate in order to carry out the biopsy. While this approach is commonplace in most laparoscopic operations carried out in the abdomen, such as the laparoscopic cholecycstecomy, there are unique features of an endothoracic operation that make this approach undesirable. First, it is almost always necessary to utilize a general anesthetic to perform a thoracoscopic lung biopsy. In addition, it is nearly always necessary to utilize a specially placed, and more complicated dual lumen endrotracheal tube so that artificial ventilation can be delivered to the opposite lung, and excluded to the side of the lung that is being biopsied. This technique, known as single lung ventilation, is needed for nearly all current thoracoscopic operations. Many patients with end stage lung disease, however, are unable to tolerate a general anesthetic, and of those that tolerate a general anesthetic, many cannot tolerate single lung ventilation because their respiratory reserve is so limited. Additionally, the intercostal spaces are particularly sensitive to pressure, as there is a fixed and limited space between the ribs, and the intercostal nerve runs underneath each rib in the intercostal space. Each time a thoracostomy is performed, pain can be severe and prolonged. This is especially the case with larger thoracostomy port sizes, such as 10 mm and 12 mm ports that are commonly used for contemporary thoracoscopy. Some studies have estimated that as many as one third of patients have chronic pain in their chest wall up to one year after thoracoscopy, and it is believed this is due to intercostal nerve irritation that occurs when multiple, large ports are introduced into the pleural space between the ribs. Single port procedures have been reported in the literature for very limited procedures, but they generally require very large incisions, 30 mm or more, to get multiple instruments through a single port.

Because of the drawbacks of bronchoscopy, open lung biopsy, and thoracoscopy, a large percentage of patients are simply not referred for lung biopsy because the referring physician is uncomfortable with the degree of invasiveness coupled with the accuracy of the available techniques. Given the advancements in imaging and the improved appreciation of the value of tissue diagnosis in lung disease, new techniques are needed to biopsy the lung in a precise, minimally invasive manner.

BRIEF DESCRIPTION OF THE DRAWINGS

Like reference numbers generally indicate corresponding elements in the figures.

FIGS. 16A and 16B are side cross-sectional and front views of a needle, respectively, suitable for advancing along the snare shaft and cutting a tract in the tissue, in accordance with an embodiment of the present invention;

FIGS. 18A and 18B are side cross-sectional and end views, respectively, of a pull-type cutting device in a deployed or expanded configuration, in accordance with an embodiment of the present invention;

FIGS. 25-40 are cross-sectional views illustrating a method for obtaining an excision of lung tissue from a patient, in accordance with the present invention.

DETAILED DESCRIPTION

Figure 1:
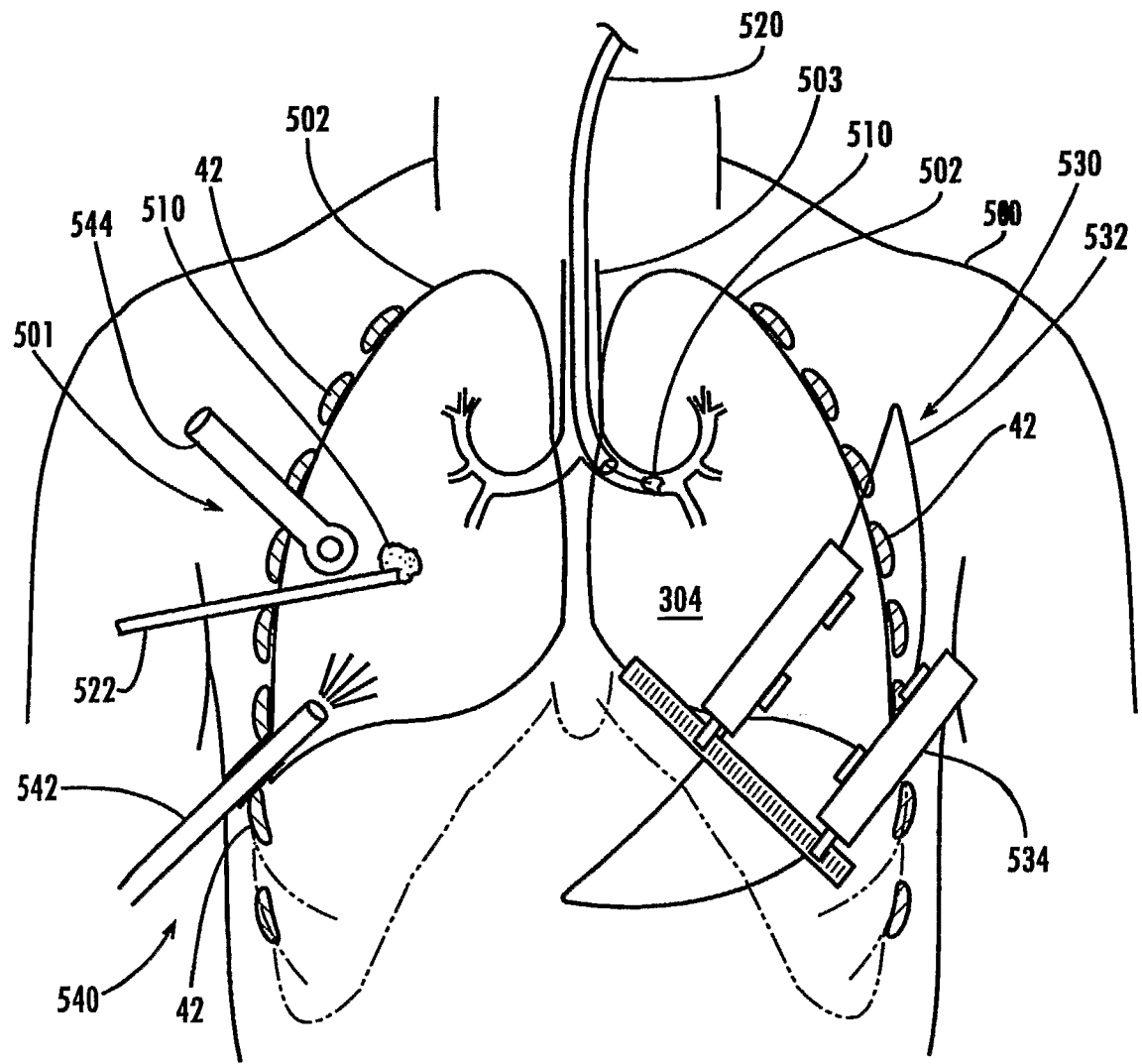
FIG. 1 is an illustration showing various prior art methods to biopsy a lung nodule.

Reference will now be made to embodiments illustrated in the drawings and specific language which will be used to describe the same. It will nevertheless be understood that no limitation of the scope of the invention is thereby intended, such alterations and further modifications in the illustrated devices, as such further applications of the principles of the invention as illustrated therein as being contemplated as would normally occur to one skilled in the art to which the invention relates.

Methods and apparatus are provided to facilitate the minimally invasive removal of tissue biopsies, in accordance with embodiments of the present invention.

Methods and apparatus are provided to facilitate the direct approach to anesthetizing the chest wall, in accordance with embodiments of the present invention.

Methods and apparatus are provided to create a microport channel to introduce instruments through a channel in the chest wall.

Methods, devices and apparatus to secure and excise lung tissue, in accordance with embodiments of the present invention.

Methods, devices, and apparatus to dilate an access tract within the lung tissue accordance with embodiments of the present invention.

Methods, devices, and apparatus to utilize suction/vacuum to suck down the dilated tract within the lung tissue to minimize bleeding and air leak during the procedure accordance with embodiments of the present invention.

Methods, devices, and apparatus to utilize suction/vacuum to suck or draw down the dilated tissue tract within the lung tissue to minimize bleeding and air leak during the procedure accordance with embodiments of the present invention.

Methods, devices, and apparatus to utilize cut out and excise the target tissue.

Methods and apparatus are provided to determine if an air leak is present from a lung biopsy, in accordance with embodiments of the present invention.

Methods and apparatus are provided to drain and seal a lung tract, in accordance with embodiments of the present invention.

Methods and apparatus are provided to seal or plug a body space defect or defect in an internal lumen of the bronchus or gut, in accordance with embodiments of the present invention.

One of the challenges in performing a minimally invasive lung biopsy is how to create a small hole or port in the chest wall. In traditional thoracoscopy, when it is desired to place a thoracostomy port across the chest wall into the pleural space, or when placing a chest tube to drain fluid from the pleural space surrounding the lung, it is commonly taught that a big enough incision be made to allow the operator to finger dissect through the intercostal space, the space between adjacent ribs, into the pleural space so that any lung that is adhered to the chest wall can be dissected free prior to placing the chest tube. This will not suffice when one wishes to place 3 to 5 mm ports, as a finger dissection usually requires at least a 12 to 15 mm port. Thus, in order to make a small sized port that is far smaller than the operator's finger, currently the operator must make an incision, dissect down with a sharp instrument, and blindly push through the chest wall without feeling the underlying tissue or structures. This adds considerable risk to the procedure, as it potentially endangers the underlying critical structures such as the lung itself, the large blood vessels in the chest, the diaphragm and liver, and the heart. Thus it is commonly taught that one should never advance an instrument into the chest without manually feeling and dissecting the underlying structures to make sure they are not in proximity to the incoming sharp instrument.

Apparatus and methods are provided to create measured microports of predetermined size through body tissue, in accordance with embodiments of the present invention. The apparatus provides access to a body space through one or more small incisions, for example, but not limited to, less than 10 mm (0.4 inch), without endangering underlying structures in the space. The apparatus provides tissue cutting directed away from the critical internal structures, and towards the operator. The apparatus creates a cutting action when pulled on, and therefore, can be referred to as a pull-type cutting device.

Figure 2A:
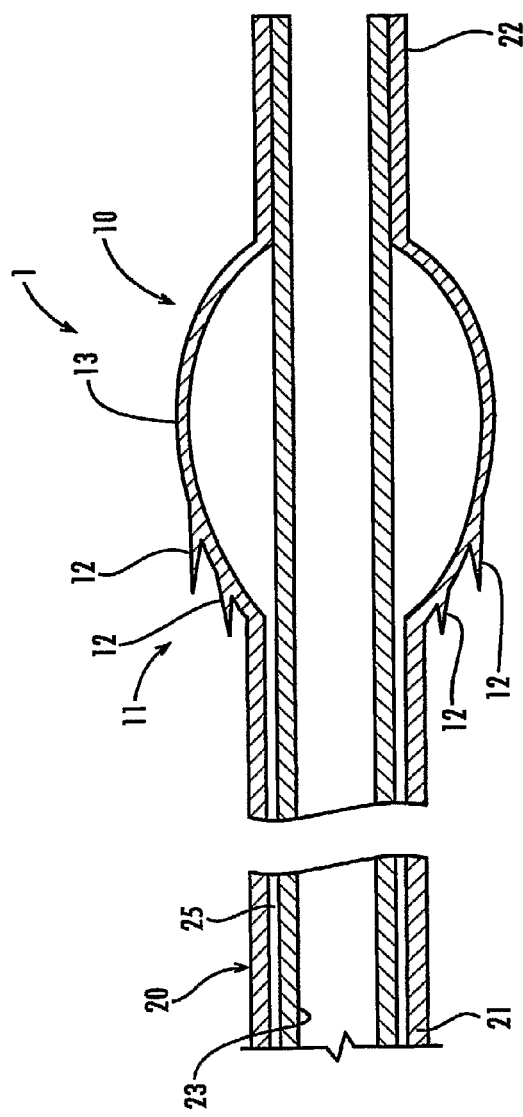
FIGS. 2A and 2B are side cross-sectional views of a pull-type cutting device in an expanded and deflated configuration, respectively, in accordance with an embodiment of the present invention.
Figure 2B:
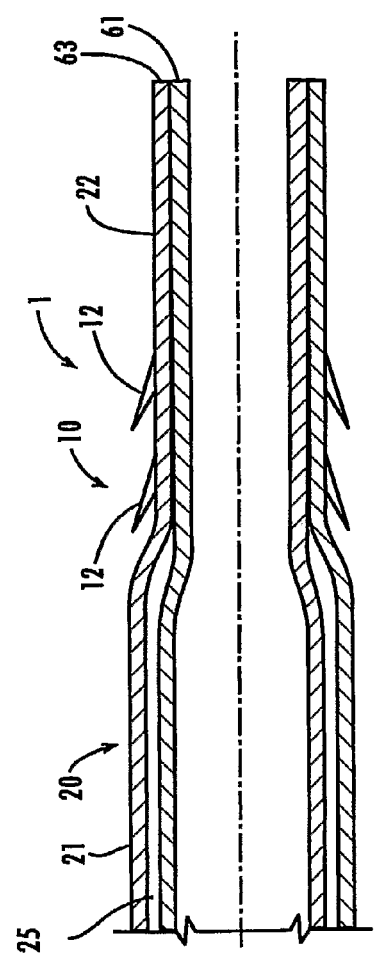
Figure 3A:
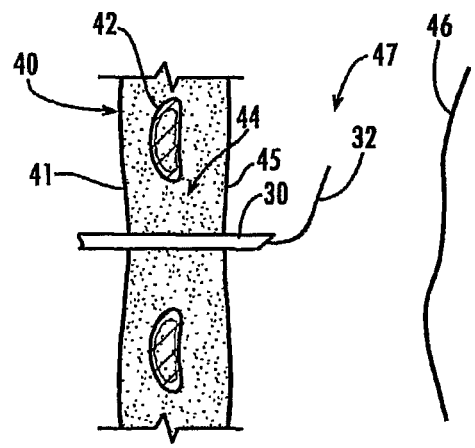
FIGS. 3A-3E are cross-sectional views showing an embodiment of a method of the present invention, wherein a body space, such as, but not limited to, a pleural space, is accessed and provided with a microport.
Figure 3B:
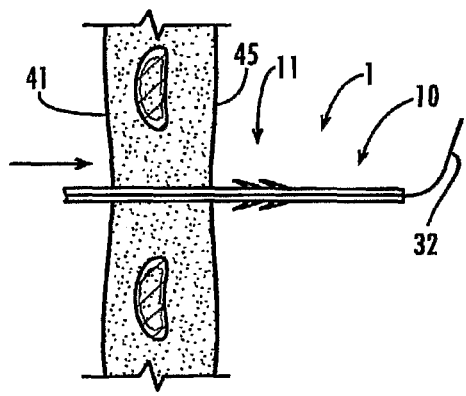
Figure 3C:
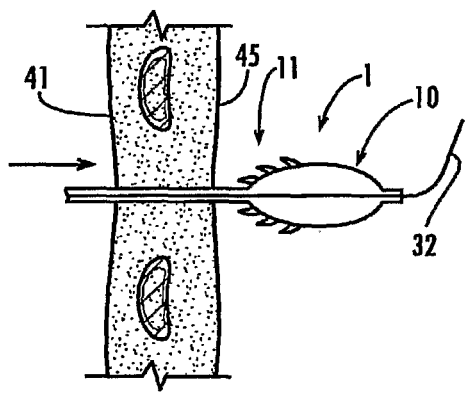
Figure 3D:
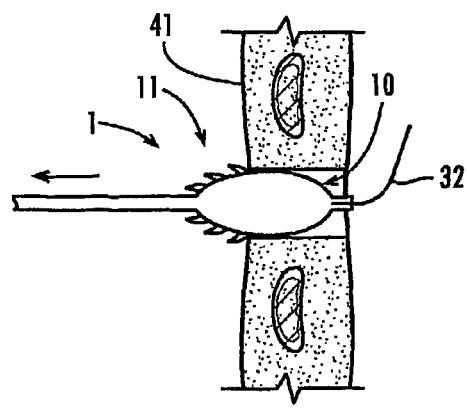
Figure 3E:
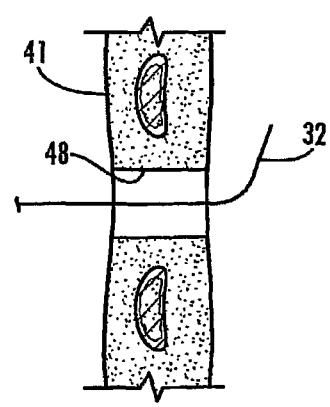

FIGS. 2A and 2B are side cross-sectional views of a pull-type cutting device 1 in a deployed or expanded configuration and in an undeployed, deflated configuration, respectively, in accordance with an embodiment of the present invention. The pull-type cutting device 1 comprises an elongated shaft 20 having a shaft distal end 22 and a shaft proximal end 21 and a shaft lumen 23 extending there through. The pull-type cutting device 1 comprises two coaxially nested tubes, each extending from the proximal end 21 to the distal end 22; a first tube 61 and a second tube 63. The first tube 61 defines a guide wire lumen 23 extending there through adapted to slidingly receive a guide wire therein. The second tube 63 extends over the first tube 60 and coupled thereto at the shaft distal end 22. The second tube 63 defines an expandable portion 13 adjacent the shaft distal end 22. The second tube 63 defines an inflation lumen 25 extending from the shaft proximal end 21 to the expandable portion 13. The inflation lumen 25 is adapted to communicate inflation fluid from the shaft proximal end 21 to the expandable portion 13 so as to inflate and deploy the expandable portion 13 to a diameter larger than that of the deflated or pre-deployed position. Disposed adjacent the shaft distal end 22 is a cutting head 10. The cutting head 10 comprises the expandable portion 13 having a cutting portion 11 distal from the shaft distal end 22.

In an embodiment, the pull-type cutting device 1 comprises an over-the-wire balloon catheter, wherein the expandable portion 13 is a balloon, and the shaft lumen 23 is adapted to pass over a guide wire. Over-the-wire balloon catheters are known in the cardiovascular art. The cutting portion 11 is adapted to be pulled into contact with the inner wall of a body space. Extending from the cutting portion 11 are a plurality of cutting elements 12. Examples of cutting elements 12 include, but are not limited to, blades, radiofrequency, laser, and electrocautery cutting elements, that are adapted to create an incision when pulled against tissue. Since the pulling and cutting action is towards the operator, this results in an improved safety profile as it lessens the risk that an internal organ or other structure can be damaged as the body space opening is created.

In an embodiment, the device 1 is referred to as a microthoratome, adapted to make measured microports through the chest wall and adjacent or into the thoracic cavity, in accordance with embodiments of the present invention.

Other embodiments are anticipated that are directed to procedures outside of the thoracic cavity, such as, but not limited to, for accessing the peritoneal space for laparoscopy, abscess cavities, the GU tract, the air way for a tracheostomy, and blood vessels.

FIGS. 3A-3E are cross-sectional views showing an embodiment of a method of the present invention, wherein a body space 47, such as, but not limited to, a pleural space, is accessed and provided with a microport 48. Utilizing the known over-the-wire Seldinger technique, a needle 30 is advanced from the chest wall outer surface 41 between two ribs 42 and into the body space 47 a predetermined distance and position. A guide wire 32 is passed through the needle 30 and into the body space 47 (such as the pleural space). The needle 30 is advanced and removed from the guide wire 32. The deflated pull-type cutting device 1 is advanced over the guide wire 32 by passing the lumen 23 over the guide wire 32. The cutting head 10 is placed beyond the tissue 45 to be cut. The cutting head 10 is deployed such that the cutting portion 11 is adjacent the tissue 45 to be cut. The pull-type cutting device 1 is pulled into contact with the inner surface 45 of the body space 47 such that the cutting elements 12 are pulled into contact with the inner surface 45 of the body space 47. The operator pulls the cutting head 10 towards the chest wall outer surface 41, whereby cutting a microport 48 through the tissue of the intercostal space 44 towards the chest wall outer surface 41 of the body space 47. In this fashion a microport 48 is created where the cutting direction is towards the chest wall outer surface 41 of a body space 47, rather than towards the chest wall inner surface 45. This results in an improved safety profile as it lessens the risk that an internal organ or other structure can be damaged as the microport is created.

One of the biggest areas of unmet need in thoracic surgery relates to pain control. Embodiments of the present invention are adapted to very precisely anesthetize the patient with local anesthesia prior to putting in the microports. Unlike traditional thoracotomy and thoracoscopy which is usually done on a patient under general anesthesia, embodiments of the present invention allow the formation of microports and subsequent procedures to be done on awake patients to minimize risks and facilitate a speedier recovery.

Apparatus and methods are provided for safe and precise access to the intercostal space for the infiltration of fluids or substances for diagnostic or therapeutic purposes, such as an anesthetic agent, in accordance with embodiments of the present invention.

Figure 4:
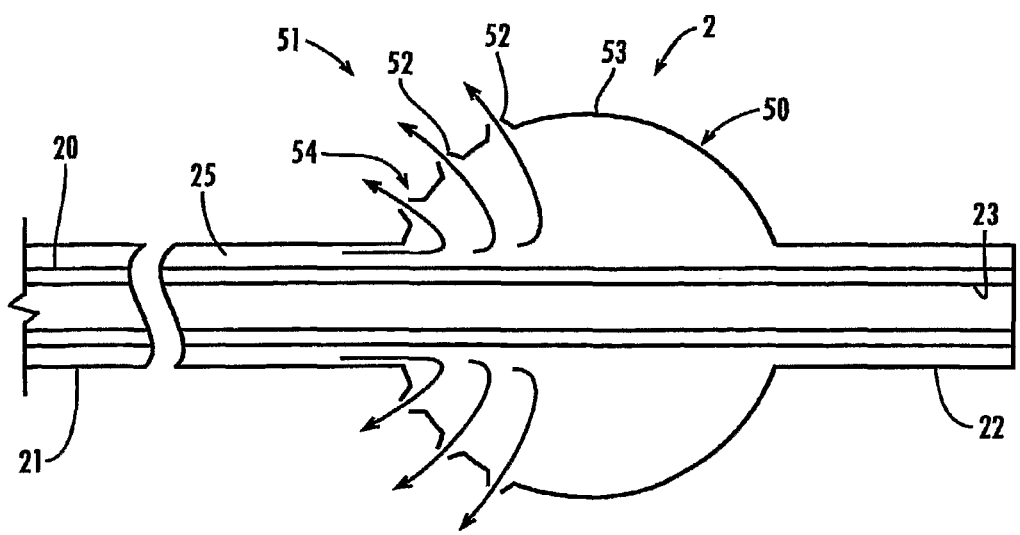
FIG. 4 is a side view of an anesthesia delivery catheter comprising a shaft having a shaft distal end and a shaft proximal end, a guide wire lumen extending there through, and a fluid lumen extending there through, in accordance with an embodiment of the present invention.
Figure 6:
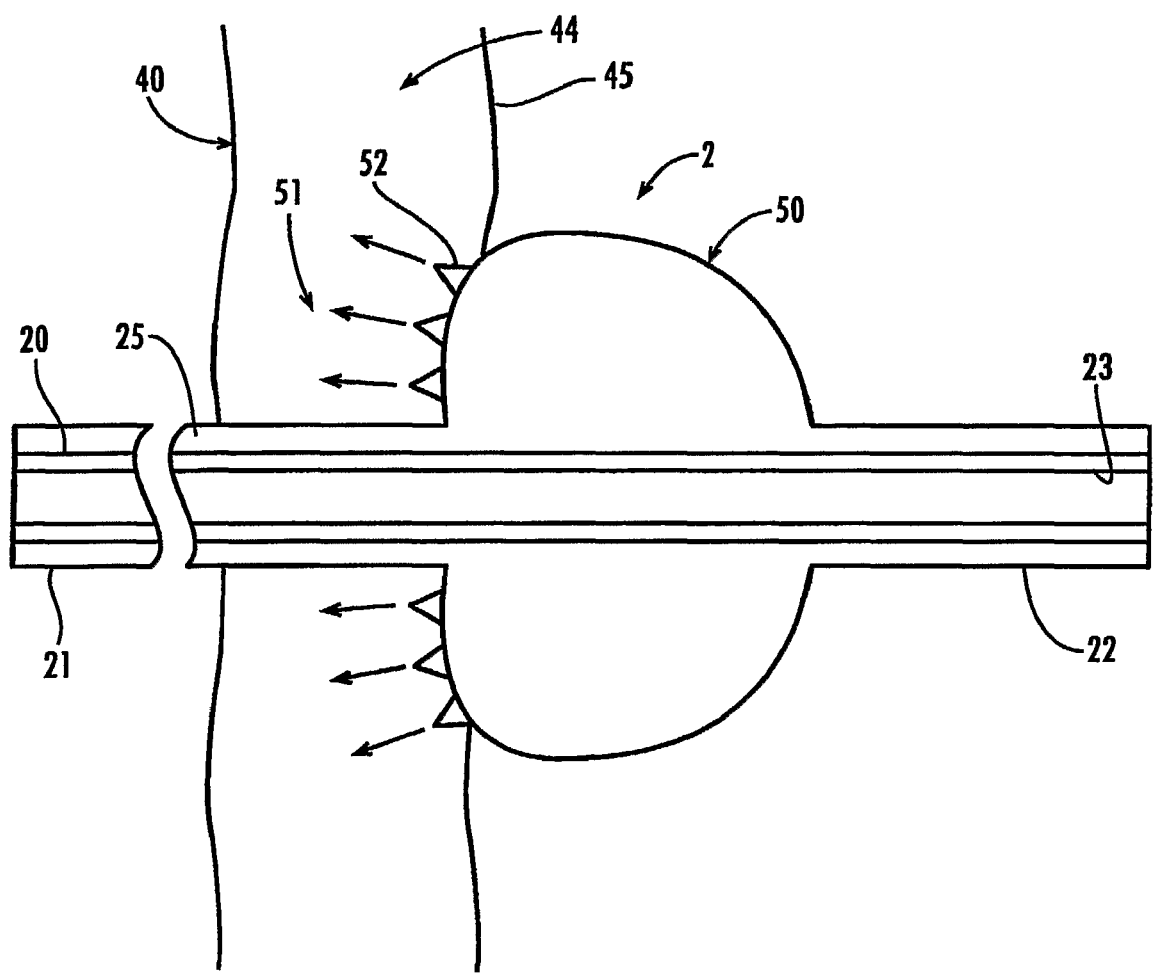
FIG. 6 is a side view of the wherein the anesthesia delivery catheter is engaged such that the delivery elements are delivering fluid to the tissue of the intercostal space, in accordance with another embodiment of the present invention.

FIG. 4 is a side view of an anesthesia delivery catheter 2 comprising a shaft 20 having a shaft distal end 22 and a shaft proximal end 21, a guide wire lumen 23 extending there through, and a fluid lumen 25 extending there through, in accordance with an embodiment of the present invention. Disposed adjacent the shaft distal end 22 is a treatment head 50. The treatment head 50 comprises an expandable portion 53 in the form of a balloon. The expandable portion 53 includes a treatment portion 51. The expandable portion 53 is in fluid communication with the fluid lumen 25 and is adapted to fill with a fluid that is introduced into a fluid lumen 25 at the shaft proximal end 21. The treatment portion 51 comprises a plurality of delivery elements 52, such as, but not limited to, hollow tines and micro introducer needles, that are adapted to extend from the treatment portion 51 and to come into contact with the pleural surface 45 of the intercostal space 44 when the expandable portion 53 is deployed, as shown in FIG. 6. FIG. 6 is a side view of the anesthesia delivery catheter 2 wherein the anesthesia delivery catheter 2 is engaged such that the delivery elements 52 are delivering fluid to the tissue of the intercostal space 44.

The delivery elements 52 comprise an aperture 54 that is in fluid communication with the fluid lumen 25. The apertures 54 are adapted to communicate a fluid from the fluid lumen 25 directly into the tissue 45 of the intercostal space 44 from "the inside out". Possible fluids for infusion into the tissue 45 include, but are not limited to, short or long acting local anesthetic agents, steroids, and neurolytic ablative agents such as alcohol or phenol.

Figure 5:
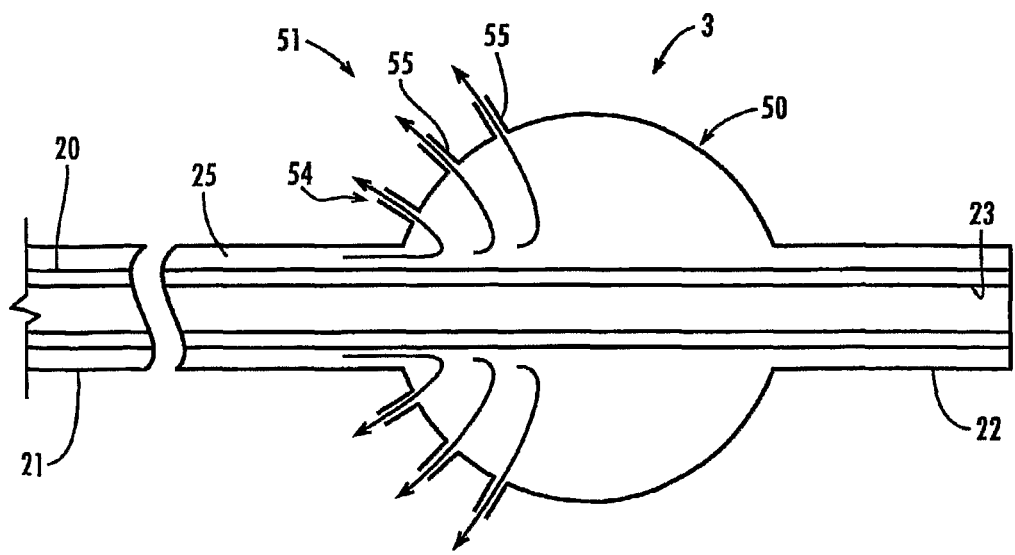
FIG. 5 is a side view of an anesthesia delivery catheter wherein the treatment head comprises delivery elements in the form of micro-needles, in accordance with another embodiment of the present invention.

Referring again to the embodiment of FIG. 4, the delivery elements 52 are in the form of a hollow cone, in accordance with an embodiment of the present invention. FIG. 5 is a side view of an anesthesia delivery catheter 3 wherein the treatment head 50 comprises delivery elements 55 in the form of micro-needles, in accordance with another embodiment of the present invention.

Figure 7A:
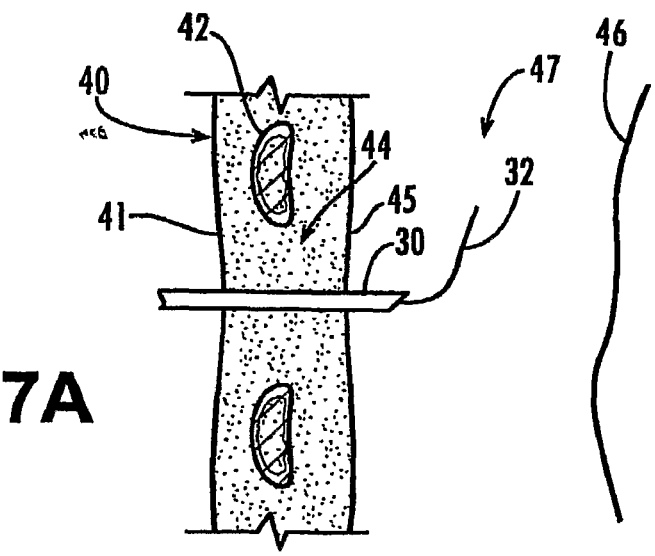
FIGS. 7A-7C are cross-sectional views showing an embodiment of a method of the present invention, wherein a body space, such as, but not limited to, a pleural space, is accessed and the intercostal space is provided with a local anesthesia, in accordance with another embodiment of the present invention.
Figure 7B:
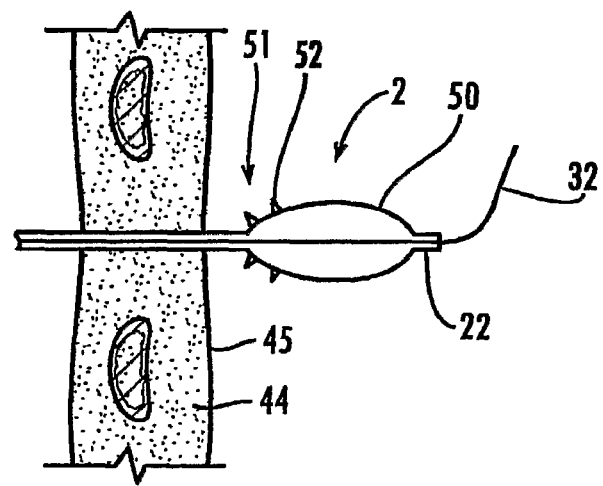
Figure 7C:
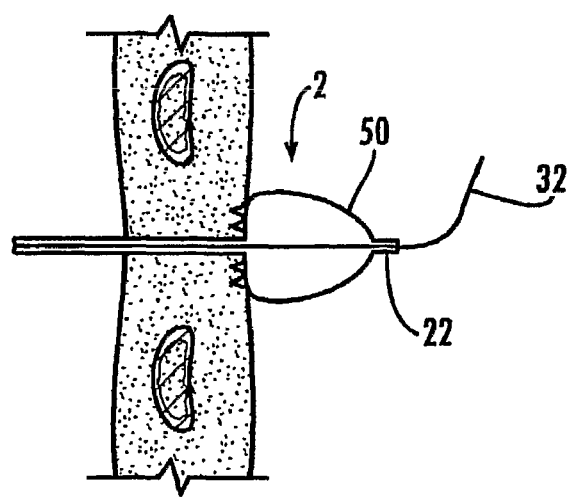

FIGS. 7A-7C are cross-sectional views showing an embodiment of a method of the present invention, wherein a body space 47, such as, but not limited to, a pleural space, is accessed and the intercostal space 44 is provided with a local anesthesia. In an embodiment of a method of the present invention, a micro-introducer needle 30 is advanced between two ribs 42 into the pleural space 47. A guide wire 32 is advanced through the needle 30 to a predetermined location beyond the needle 30. The needle 30 is removed from the guide wire 32 leaving the guide wire 32 in place. The guide wire lumen 23 of the anesthesia delivery catheter 2 is advanced over the guide wire 32 with the treatment head 50 advanced into the pleural space 47. The treatment head 50 adjacent the distal end 22 of the anesthesia delivery catheter 2 is then insufflated with a fluid, including, but not limited to, air, gas, or liquid, such as saline, water, or therapeutic substances including local anesthetic agents. The anesthesia delivery catheter 2 is then pulled back towards the operator pulling the treatment portion 51 in urging contact with the inner surface 45 of the intercostal space 44. The delivery elements 52 penetrate the inner surface 45 so as to infuse fluid into the tissue of the intercostal space 44.

This method is superior to a standard intercostal nerve block due to the precise delivery of therapeutic agent into the intercostal space. In a standard intercostal nerve block, the operator has to guess how deep to insert the needle. When it is too shallow, the nerve is missed and the therapeutic benefit is not achieved. When the needle is too deep, the therapeutic agent is instilled into the pleural space, and the therapeutic benefit is not achieved. Furthermore, if the needle is put in too deep, the lung, or other intrathoracic structures can be injured, such as the heart and great vessels, leading to a pneumothorax. While this is a risk any time a needle is inserted between the ribs into the pleural space, it is a particular concern in an intercostal nerve block when the needle is moved in and out of the space in an attempt to maximally infiltrate the space around the intercostal nerve. A needle that is too deep or too shallow is particularly a problem when infusing a neurolytic agent with the aim of ablating the nerve permanently. To minimize misplacement of the needle in the course of an intercostal nerve block, image guidance in the form of fluoroscopy is used to help guide the needle. Even with image guidance, however, it is nearly impossible to be sure that the needle is appropriately placed in a location where the treating substance can come in contact with the intercostal nerve without injuring the deeper structures, such as the lung.

In another embodiment of a method of the present invention, tumescent anesthesia is used to infiltrate intercostal tissue. Tumescent means swelling or distention. Tumescent anesthesia is commonly employed in outpatient, office-based procedures such as liposuction or endovenous saphenous vein ablation. With tumescent anesthesia, the tissues are flooded with dilute liquid anesthetic and become distended. The unique feature of tumescent anesthesia is that it involves the use of a very low concentration of local anesthetic. The large volume of fluid causes vessels to be compressed resulting in minimal bleeding. The anesthesia achieved by this technique is excellent and has a prolonged duration. This approach has allowed procedures to be employed in the out-patient setting that formerly required a general anesthetic or major regional anesthesia.

A critical component in utilizing tumescent anesthesia in a thoracic procedure is the precise infiltration of the anesthetic agent into the proper location around the intercostal nerve, without going too deep where the lung can be injured by the needle or the pleural space can be infused.

General anesthesia with single-lung ventilation is considered mandatory for any open or thoracoscopic thoracic procedure. Both thoracotomy and Video-assisted thoracoscopy surgery (VATS) are classically performed using general anesthesia, usually with a double-lumen endrotracheal tube to allow collapse of the operated lung. While thoracoscopic surgery has been performed in awake patients, the adequate delivery of anesthetic agent to the intercostal space can be challenging, even with image guidance.

Figure 8A:
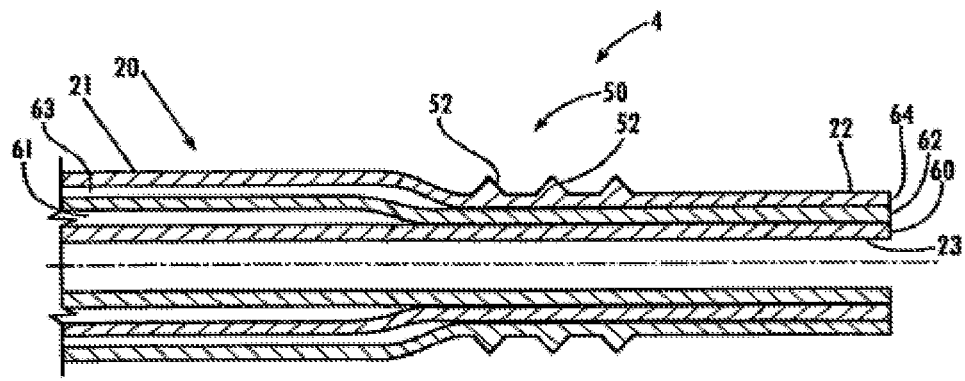
FIGS. 8A and 8B are side views of an anesthesia delivery catheter, in a pre-deployed and deployed state, respectively, comprising a shaft having a shaft distal end and a shaft proximal end, in accordance with an embodiment of the present invention.
Figure 8B:
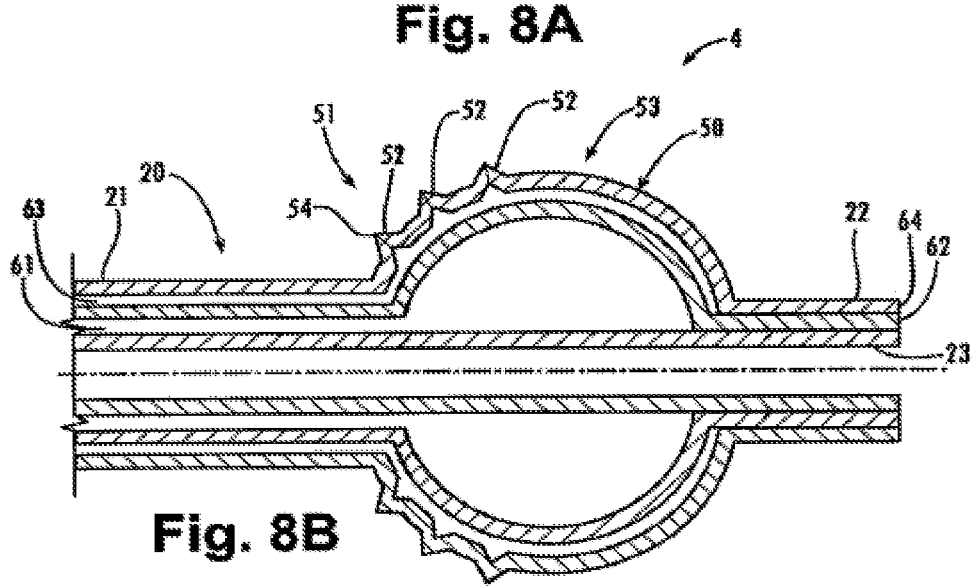

FIGS. 8A and 8B are side views of an anesthesia delivery catheter 4, in a pre-deployed and deployed state, respectively, comprising a shaft 20 having a shaft distal end 22 and a shaft proximal end 21, in accordance with an embodiment of the present invention. The delivery catheter 4 comprises three coaxially nested tubes, each extending from the proximal end 21 to the distal end 22; a first tube 60, a second tube 62, and a third tube 64. The first tube 60 defines a guide wire lumen 23 extending there through adapted to slidingly receive a guide wire therein. The second tube 62 extends over the first tube 60 and coupled thereto at the shaft distal end 22. The second tube 62 defines an expandable portion 53 adjacent the shaft distal end 22. The second tube 62 defines an inflation lumen 61 extending from the shaft proximal end 21 to the expandable portion 53. The inflation lumen 61 is adapted to communicate inflation fluid from the shaft proximal end 21 to the expandable portion 53 so as to inflate and deploy the expandable portion 53 to a diameter larger than that of the deflated or pre-deployed position.

The third tube 64 extends over the second tube 62 and coupled thereto at the shaft distal end 22. The third tube 64 defines a treatment portion 51 collocated with the expandable portion 53. The third tube 64 defines a fluid delivery lumen 63 extending from the shaft proximal end 21 to the treatment portion 51. The treatment portion 51 comprises a plurality of delivery elements 52, such as, but not limited to, hollow tines and micro introducer needles, that are adapted to extend from the treatment portion 51 and to come into contact with the pleural surface 45 of the intercostal space 44 when the expandable portion 53 is inflated. The delivery elements 52 comprise an aperture 54 that is in fluid communication with the fluid delivery lumen 63.

Figure 9A:
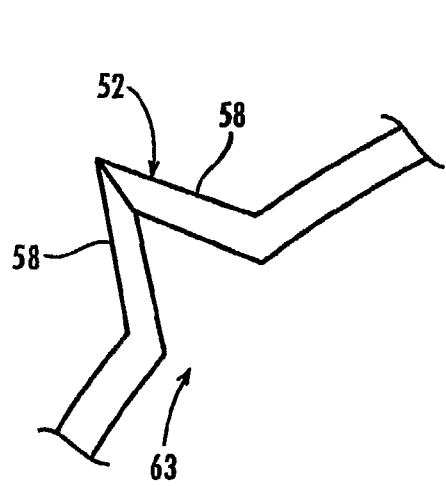
FIGS. 9A and 9B are side cross-sectional views of a delivery element, in accordance with embodiments of the present invention.
Figure 9B:
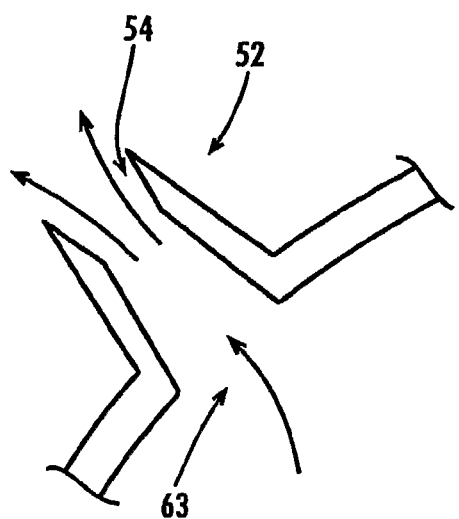

FIGS. 9A and 9B are side cross-sectional views of a delivery element 52, in accordance with an embodiment of the present invention. The delivery element 52 comprises extending resilient members 58 that are adapted to open under a predetermined fluid pressure to form an aperture 54 in fluid communication with the fluid delivery lumen 63 so as to allow fluid to exit the delivery element 52. The fluid delivery element 52 acts as a one-way valve to allow fluid to exit the aperture 54 but not enter.

Figure 10:
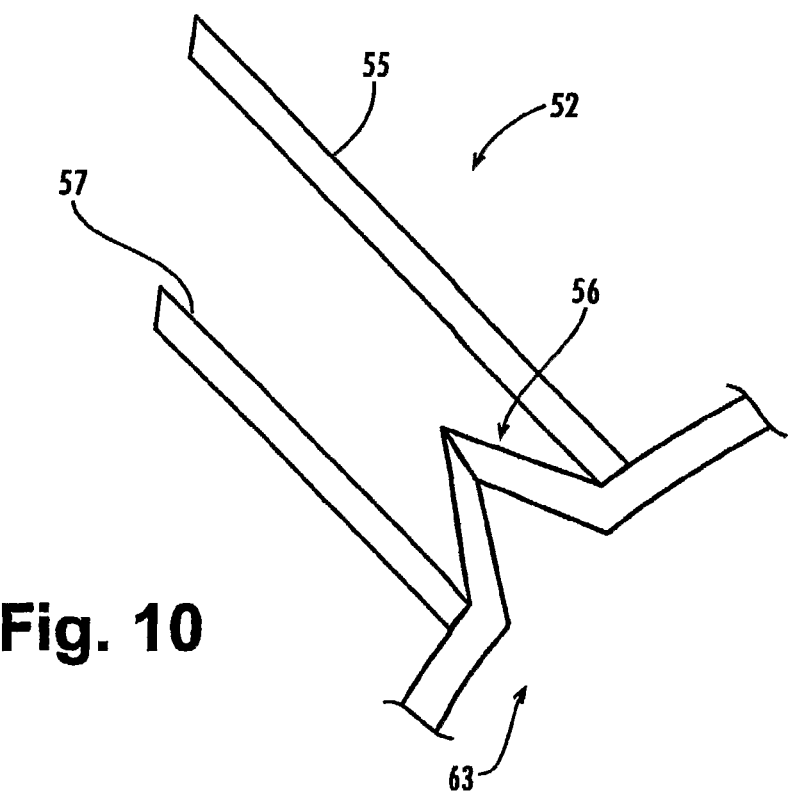
FIG. 10 is a side cross-sectional view of a delivery element, in accordance with an embodiment of the present invention.

FIG. 10 is a side cross-sectional view of a delivery element 52, in accordance with an embodiment of the present invention. The delivery element 52 comprises a micro-needle 55 having a needle lumen 57 in fluid communication with the fluid delivery lumen 63. A valve 56 between the needle lumen 57 and the fluid delivery lumen 63 is adapted to open at a predetermined pressure within the fluid delivery lumen 63, so as to allow fluid to exit the delivery element 52.

Figure 11:
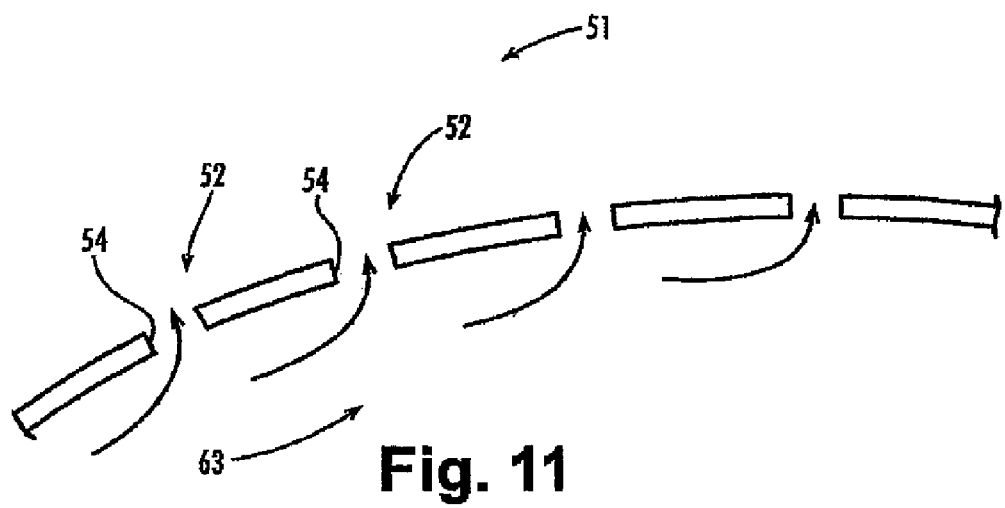
FIG. 11 is a side cross-sectional view of a delivery element, in accordance with an embodiment of the present invention.

FIG. 11 is a side cross-sectional view of a delivery element 52, in accordance with an embodiment of the present invention. The delivery element 52 comprises an aperture 54 or pore defined by the treatment portion 51. The apertures 54 are placed in urging contact with the inner surface 45 of the intercostal space 44 when the anesthesia delivery catheter 4 is pulled back towards the operator when the expandable portion 53 is inflated. Therapeutic fluid, such as anesthesia, is introduced into the fluid delivery lumen 63 at a predetermined pressure so as to expel the therapeutic fluid out of the delivery elements 52 and into the inner surface 45 under hydrostatic pressure. This type of delivery may take the form of tumescent anesthesia, used to infiltrate intercostal tissue with anesthesia fluid. Tumescent means swelling or distention. Tumescent anesthesia is commonly employed in outpatient, office-based procedures such as liposuction or endovenous saphenous vein ablation. With tumescent anesthesia, the tissues are flooded with dilute liquid anesthetic and become distended. The unique feature of tumescent anesthesia is that it involves the use of a very low concentration of local anesthetic. The large volume of fluid causes vessels to be compressed resulting in minimal bleeding. The anesthesia achieved by this technique is excellent and has a prolonged duration. This approach has allowed procedures to be employed in the out-patient setting that formerly required a general anesthetic or major regional anesthesia.

Referring again to FIGS. 7A-7C, in accordance with a method of the present invention, wherein a body space 47, such as, but not limited to, a pleural space, is accessed and the intercostal space 44 is provided with a local anesthesia. A micro-introducer needle 30 is advanced between two ribs 42 into the pleural space 47. Through the needle 30 a guide wire 32 is advanced to a predetermined location beyond the needle 30. The needle 30 is removed from the guide wire 32 leaving the guide wire 32 in place. The guide wire lumen 23 of the anesthesia delivery catheter 4 is advanced over the guide wire 32 with the treatment head 50 advanced into the pleural space 47. An inflation fluid is introduced into the inflation lumen 61 under a predetermined pressure to inflate the expandable portion 53 so as to inflate and deploy the expandable portion 53, and thus the treatment head 50. The anesthesia delivery catheter 4 is then pulled back towards the operator pulling the treatment portion 51, and thus the delivery elements 52, in urging contact with the inner surface 45 of the intercostal space 44. The delivery elements 52 penetrate the inner surface 45 so as to infuse fluid into the tissue of the intercostal space 44. Therapeutic fluid, such as anesthesia, is introduced into the fluid delivery lumen 63 at a predetermined pressure so as to expel the therapeutic fluid out of the delivery elements 53 and into the inner surface 45. Upon completion of the treatment, the introduction of therapeutic fluid is terminated and the inflation fluid is extracted from the inflation lumen 61 adapted to cause the expandable portion 53 to deflate and substantially conform to the pre-expanded state. The anesthesia delivery catheter 4 is withdrawn from the guide wire 32. The guide wire 32 is left in place.

After the intercostal space is anesthetized, a cutting catheter is advanced over the guide wire 32 and a micro-port is created substantially as provided in FIGS. 3B-3E.

In another embodiment of the present invention, this method and device is used to instill tumescent anesthesia into an awake patient for the purpose of anesthetizing an intercostal spaces. This could be used clinically for the placement of a chest tube, or the placement of intercostal ports for awake thoracoscopy. In another embodiment, the method and device is used to treat acute or sub acute rib fractures with pain or anti-inflammatory agents such as steroids. In another embodiment, the method and device is used to instill a neurolytic agent for the permanent ablation of a nerve for the purpose of chronic pain management.

Figure 8C:
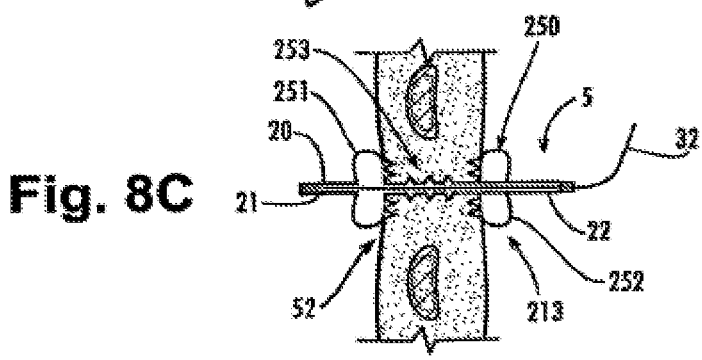
FIG. 8C is a side view of an anesthesia delivery catheter, in accordance with an embodiment of the present invention.

FIG. 8C is a side view of another embodiment of a treatment catheter 5 comprising a shaft 20 having a shaft distal end 22 and a shaft proximal end 21, a guide wire lumen extending there through, and a fluid lumen extending there through, in accordance with an embodiment of the present invention. Disposed adjacent the shaft distal end 22 is a treatment head 250. The treatment head 250 comprises an expandable portion 213 in the form of a balloon. The balloon 213 has a distal end 252 proximate the distal end 22 of the shaft 20 and a proximal end 212 distal from the distal end 22 of the shaft 20, and a balloon central portion 253 there between. The distal 252 and proximal 251 ends of the balloon 213 are larger than the balloon central portion 253; resembling a dumbbell. The balloon 213 is in fluid communication with the fluid lumen and is adapted to fill with a fluid that is introduced into a fluid lumen at the shaft proximal end. The balloon 213 has a plurality of delivery elements 52 adapted to release fluid from within the balloon 213 to external the balloon 213 at a predetermined pressure.

In another embodiment of a method of the present invention, the treatment catheter 5 is collapsed and advanced over a placed guide wire. The balloon 213 is preferentially placed within the intercostals space. The balloon 213 is pressurized with an anesthetic agent, such as, but not limited to, a tumescent anesthesia utilizing a dilute lidocaine solution. Once the intercostal space has been infiltrated with the anesthetic agent, the fluid expanding the balloon 213 is withdrawn and the balloon 213 is deflated, and the catheter 5 is removed.

In other embodiments of the present invention, the treatment catheter comprises a combination of the anesthetic instilling embodiments with delivery elements 52 with the cutting embodiments with a cutting portion 11 so that as soon as the chest wall is very precisely anesthetized, a small port can be cut by pulling the cutting element out towards the operator.

Figure 12A:
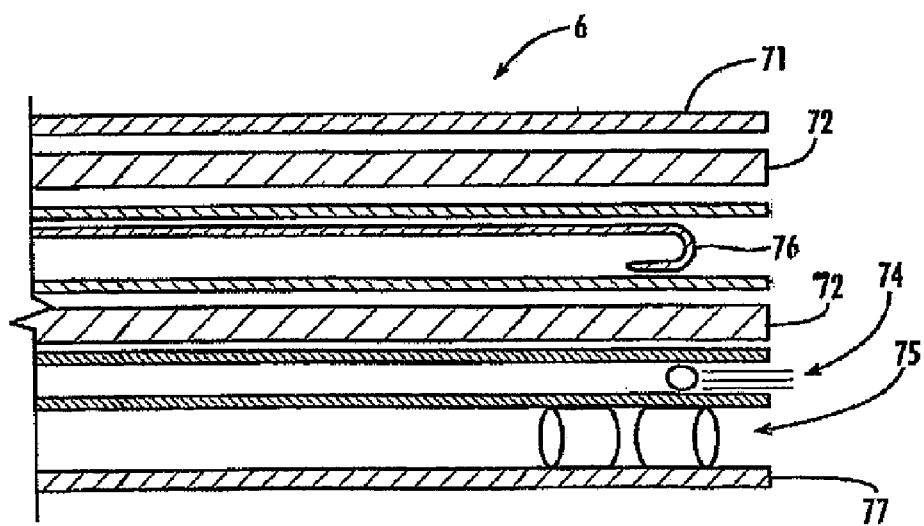
FIGS. 12A-C are side cross-sectional views of a biopsy tool for gathering a biopsy sample, such as lung tissue, in accordance with an embodiment of the present invention.
Figure 12B:
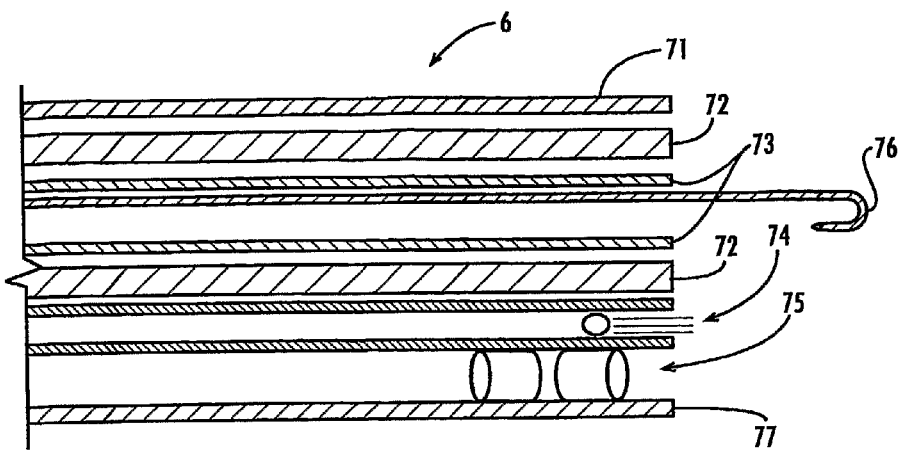
Figure 12C:
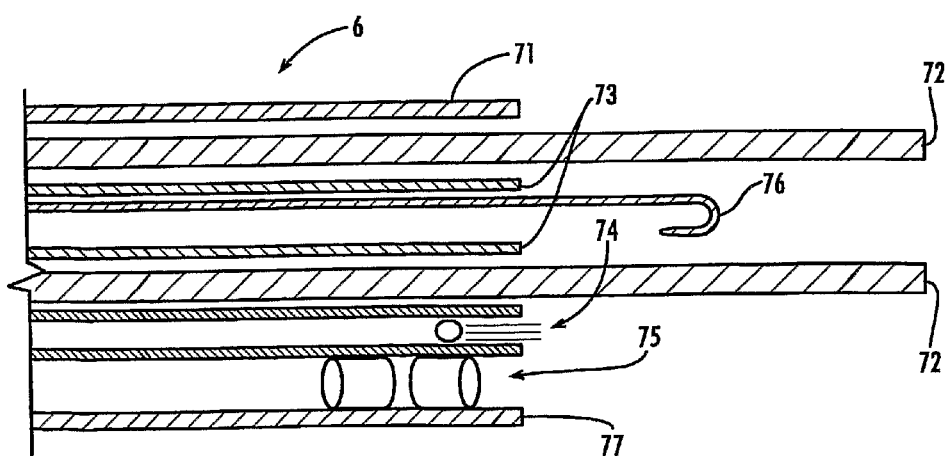

FIGS. 12A-12C are side cross-sectional views of a biopsy tool 6 for gathering a biopsy sample, such as lung tissue, in accordance with an embodiment of the present invention. The biopsy tool 6 comprises an outer sheath 71 housing a tissue cutting element 72, an endoscope 75 with light source 74, and a tissue grasping element 76. The tissue cutting element 72 and the tissue grasping element 76 are adapted to extend from and retract into the outer sheath distal end 71, suitable for a particular purpose.

FIG. 12A shows the biopsy tool 6 wherein the tissue cutting element 72 and the tissue grasping element 76 are stowed within the outer sheath 71. When stowed, the biopsy tool 6 may be inserted through a microport and into the body space, such as, but not limited to, the pleural space to adjacent the lung. FIG. 12B shows the biopsy tool 6 wherein the tissue grasping element 76 is extended from the outer sheath distal end 71 so as to couple with target tissue to be biopsied. FIG. 12C shows the biopsy tool 6 where the tissue cutting element 72 extends beyond the tissue grasping element 76 so as to sever and contain the target tissue.

In accordance with an embodiment of the present invention, the biopsy tool 6 has an outer diameter between 2 and 5 mm, suitable for insertion into microports as described above. It is anticipated that other elements may be housed within the outer sheath 71.

Figure 13A:
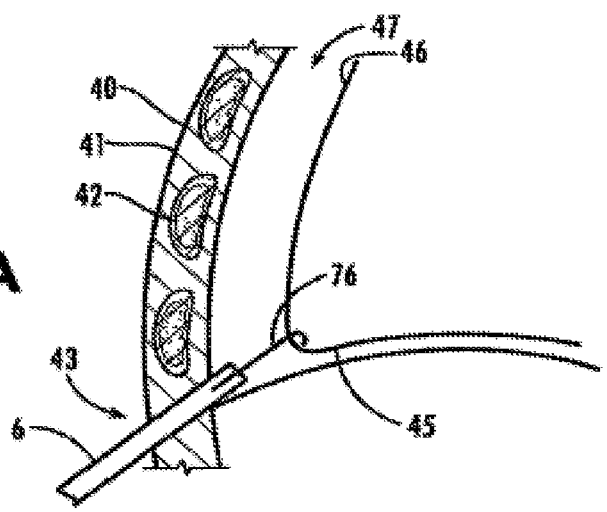
FIGS. 13A-C illustrates a method for obtaining a biopsy of lung tissue using the biopsy tool, in accordance with the present invention.
Figure 13B:
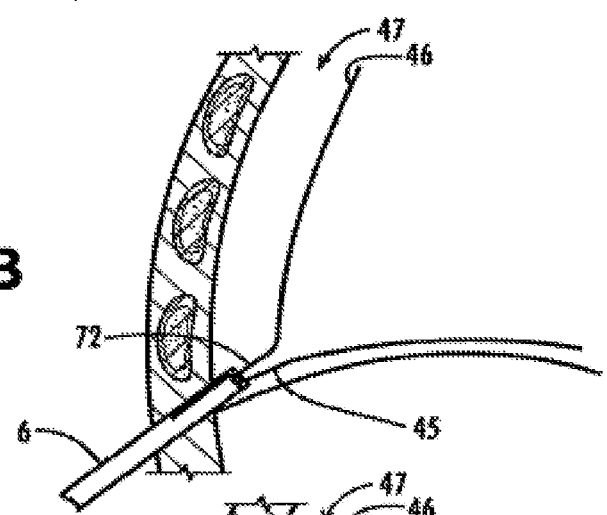
Figure 13C:
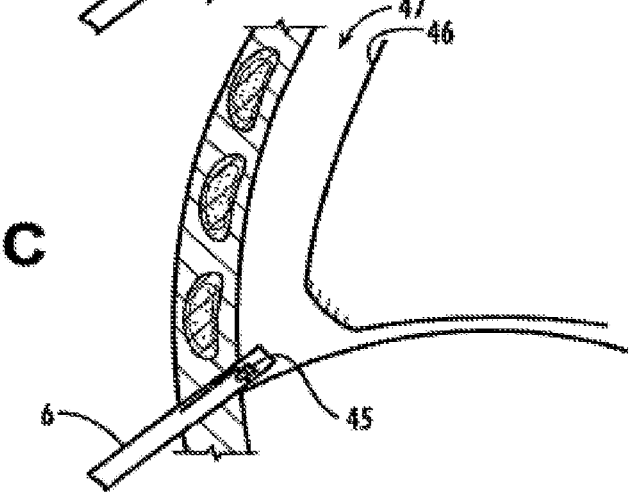

FIGS. 13A-13C illustrate a method for obtaining a biopsy of lung tissue using the biopsy tool 6, in accordance with the present invention. The chest wall 40 is anesthetized and a microport is created as provided in the embodiments above. The outer sheath distal end 77 is inserted through the microport 48 and placed in the pleural space 47 adjacent the target tissue 45 to be biopsied. The tissue grasping element 76 is extended and coupled with the tissue, as shown in FIG. 13A. The tissue grasping element 76 is retracted and/or the biopsy tool 6 is withdrawn a predetermined amount so as to stretch, elongate and thin out the tissue in preparation for severing. The tissue cutting element 72 is extended over the stretched tissue so that the target tissue is contained between the tissue cutting element 72 and the tissue grasping element 76, as shown in FIG. 13B. The tissue cutting element 72 severs the target tissue from the lung as well as seals the lung at the surgical site, as shown in FIG. 13C. The biopsy tool 6 is withdrawn from the microport with the target tissue contained within the tissue cutting element 72 and held by the tissue grasping element 76.

In an embodiment of a method for obtaining a biopsy of lung tissue using the biopsy tool 6, the method and biopsy tool 6 are adapted to sample lung tissue non-specially, as is done for a biopsy for ILD. The method to sample lung tissue utilizes a minimally invasive, direct approach where the viewing, grasping, and cutting mechanisms are all combined into one instrument that can be inserted through a small thoracoscopy. Because the approach is direct, and therefore does not require triangulation, single lung ventilation is not an absolute requirement as it is in traditional thoracoscopy. Furthermore, because the biopsy tool 6 is small, this approach can be carried out with the aid of a local anesthetic rather than a general anesthetic.

Embodiments of the endoscope 75 of the biopsy tool 6 include, but are not limited to, wherein the endoscope 75 is flexible, the endoscope 75 is rigid, wherein the endoscope 75 is fixed in the outer sheath 71, and wherein the endoscope 75 is adapted to be advanced in and out of the outer sheath 71 and fixed in a desired position to offer maximal visualization of the target tissue to be biopsied. In another embodiment, the distal end of endoscope 75 can have a variety of configurations allowing it to view from 0 degrees to 180 degrees.

It is appreciated that the tissue grasping element 76 can comprise many configurations suitable for the particular purpose. In the embodiment of FIGS. 12A-C and 13A-C, tissue grasping element 76 is a hook. In this embodiment, the hook is advanced out of the outer sheath distal end 77 towards the target tissue 45 and the tissue is "hooked" by the hooked shaped tissue grasping element 76. Once the target tissue 45 is hooked, the tissue grasping element 76 is pulled back towards the outer sheath distal end 77, stretching the target tissue 45 towards the optical system of the endoscopic 75. The tissue cutting element 72 is then used to shear off the target tissue 45 and the tissue grasping element 76 is adapted to pull the target tissue 45 into a channel where it is protected as the biopsy tool 6 is removed.

Other embodiments of apparatus and methods suitable to grasp the target tissue include, but not limited to, the use of suction to stabilize the tissue, the use of cryogenic freezing, and the use of a highly sticky polymer substance, among others.

It is appreciated that the tissue cutting element 72 can comprise many configurations suitable for the particular purpose. In embodiments of the present invention, the tissue cutting element 72 cuts the tissue while a separate element seals the surgical site. Embodiments of tissue cutting elements 72 where cutting is followed by sealing include cutting mechanisms, such as, but not limited to, a fitted scalpel blade that follows a predetermined loop beyond the extension of the tissue grasping element 76 from the outer sheath distal end 77 to cut tissue. The biopsy tool 6 further comprises a sealing element, such as, but not limited to, a stapling device, crimping device, and a compression device, such as but not limited to, an elastic band and a suture.

In other embodiments, the tissue cutting element 72 is adapted to cut the tissue and seal the surgical site. Apparatus suitable for cutting the tissue and sealing the surgical site include, but not limited to, elements incorporating radiofrequency, laser, high frequency ultrasound, and electrocautery.

When the purpose of the operation is to specifically sample a lung nodule or a very localized, specific interstitial abnormality, a thoracoscopy is of limited utility since there is no way to manually palpate the lung and localize the nodule or interstitial abnormality as is done in open surgery at thoracotomy. While some surgeons have attempted to localize tissue abnormalities with a coil or wire localized by CT, and then perform a generous wedge resection of tissue using standard lung stapling techniques, this technique is of limited utility due to the logistical challenges, as well as due to the continued need to wedge out a large area of lung so that a small nodule can be removed. Thus, an additional technical concern of the current methods of lung tissue excision is the need to create a wedge type incision in the lung to remove a nodule or interstitial abnormality. Generally the deeper the nodule in the lung parenchyma, the more lung tissue that must be removed due to the wider cut of the staples to form the wedge. As the wedge is cut, larger blood vessels and airways are cut, some of which can leak.

Leakage of air after lung stapling is a very common occurrence, and is especially common in deep wedge resections where the staple lines end up under great tension. When a lung leaks air after a lung wedge resection the patients hospital stay is considerably lengthened and their complication rate goes up significantly. Thus great attention is directed intra operatively to positioning staplers and technically managing the risk of air leak, but despite these efforts deep wedge resections can be difficult and the risk of air leak increases significantly the deeper the nodule, and the more technically challenging the wedge resection. When this occurs during thoracoscopy, the case is converted to a thoracotomy to provide the operating surgeon more access to mitigate these delicate issues.

In accordance with apparatus and methods of the present invention, there is provided a way to specifically excise lung tissue which provides a mechanism to locate a nodule or tissue abnormality, excise the tissue and a rim of normal lung around the tissue, and seal the cutting tract. Since the number and size of the ports utilized for thoracic surgery is directly related to the amount of acute and chronic pain, desirable features include the ability to thoracscopically sample lung tissue where a single, small port, or microport, is utilized, without utilizing standard triangulation methods. In accordance with the embodiments of FIGS. 12A-C and 13A-C, methods are adapted to sample lung tissue utilizing a minimally invasive, direct approach where the viewing, grasping, and cutting mechanisms are all combined into biopsy tool 6 adapted to be inserted through a small thoracoscopy port. Because the approach is direct, and therefore does not require triangulation, single lung ventilation is not an absolute requirement as it is in traditional thoracoscopy where the lung must be deflated to allow room in the pleural space for the instruments to work. Furthermore, because the biopsy tool 6 is small, this approach can be carried out with the aid of a local anesthetic, rather than a general anesthetic.

Figure 14A:
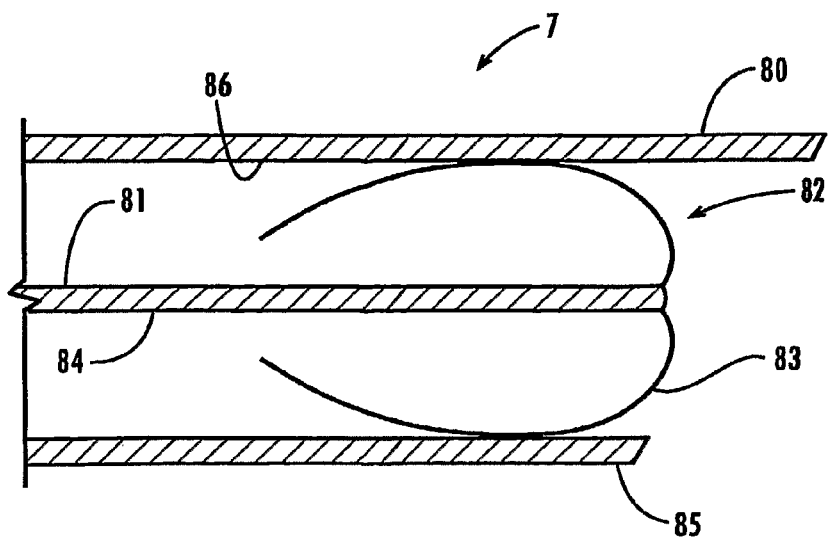
FIGS. 14A and 14B are side cross-sectional views of a biopsy tool comprising a hollow needle and a deployable and retractable snare in a retracted and deployed state, respectively, in accordance with an embodiment of the present invention.
Figure 14B:
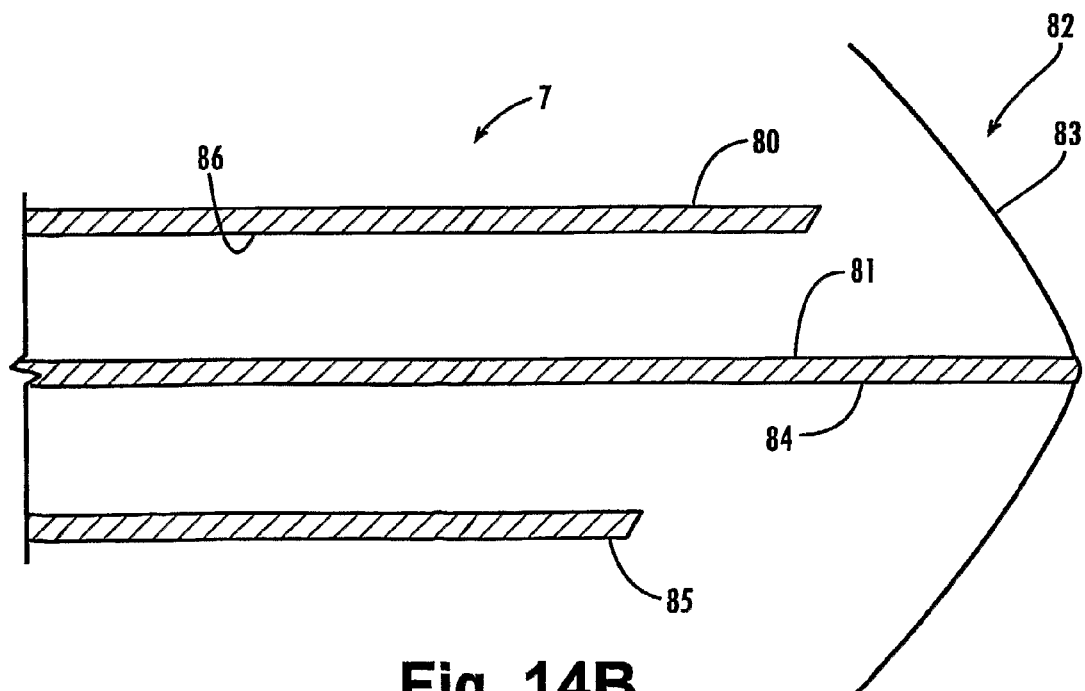

FIGS. 14A and 14B are side cross-sectional views of a biopsy tool 7 comprising a hollow needle 80 and a deployable and retractable snare 81 in a retracted and deployed state, respectively, in accordance with an embodiment of the present invention. The needle distal end 85 is sharpened so as to pass through tissue. The needle 80 defines a needle bore 86. The snare 81 comprises a snare shaft 84 and a snare head 82 at a distal end of the snare shaft 84. The snare head 82 is adapted to collapse to a low-profile state when housed within the needle bore 86, and the snare head 82 is adapted to deploy to a higher profile when extended from the needle bore 86.

The snare 81 is adapted to be advanced beyond the needle distal end 85 after the needle distal end 85 is advanced beyond the target tissue as explained below.

Figure 15A:
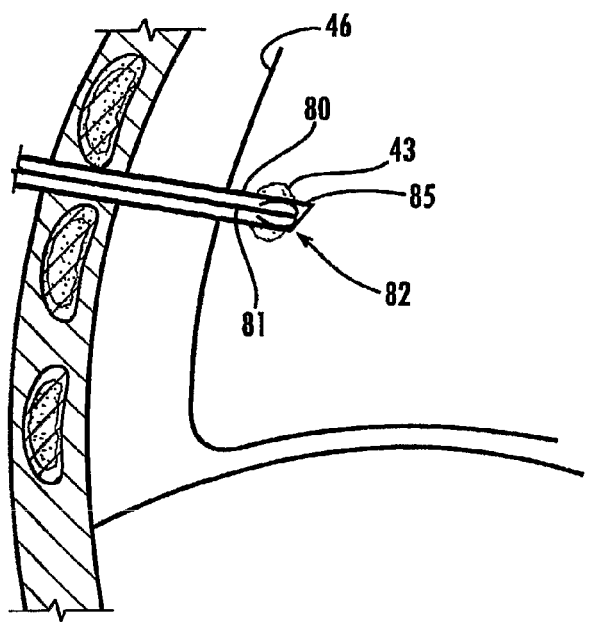
FIGS. 15A-F illustrate a method for obtaining a biopsy of lung tissue using the biopsy tool of the embodiment of FIGS. 14A and 14B, in accordance with an embodiment of the present invention.
Figure 15B:
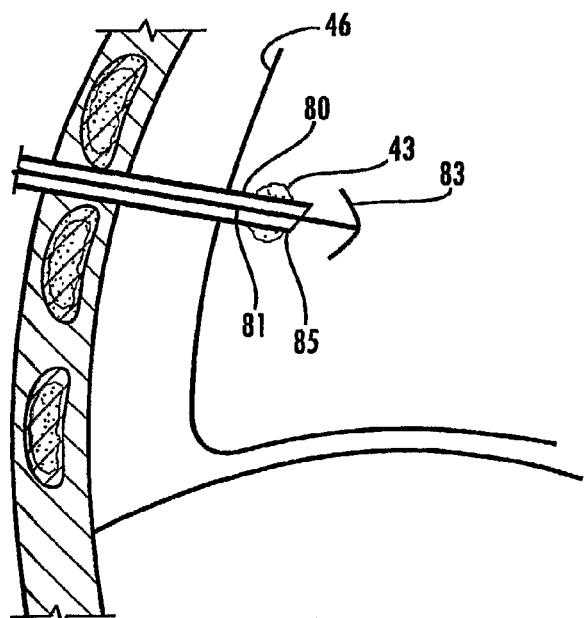
Figure 15C:
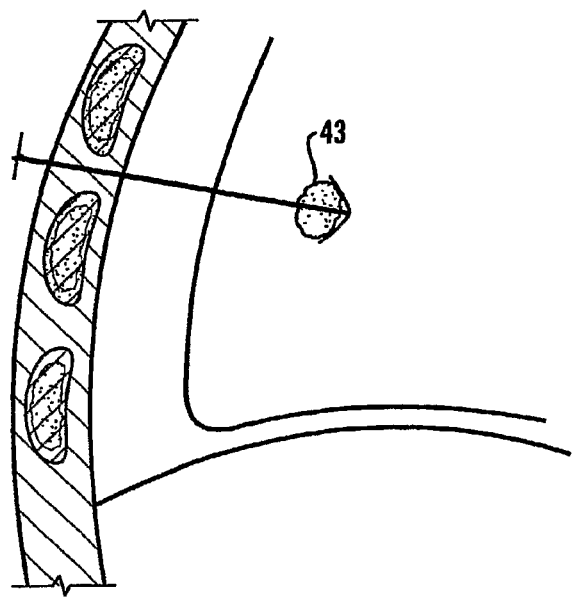
Figure 15D:
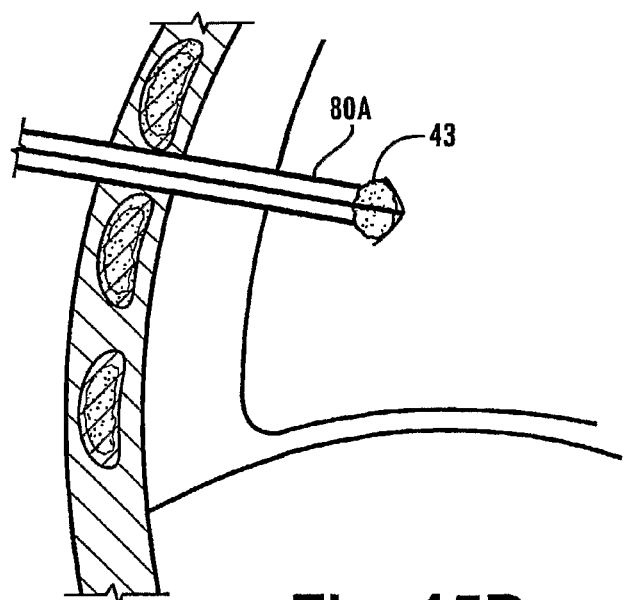
Figure 15E:
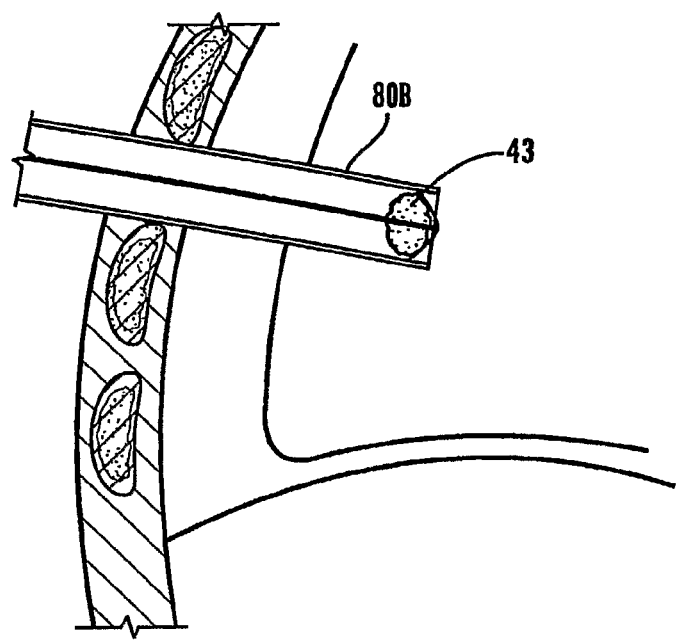
Figure 15F:
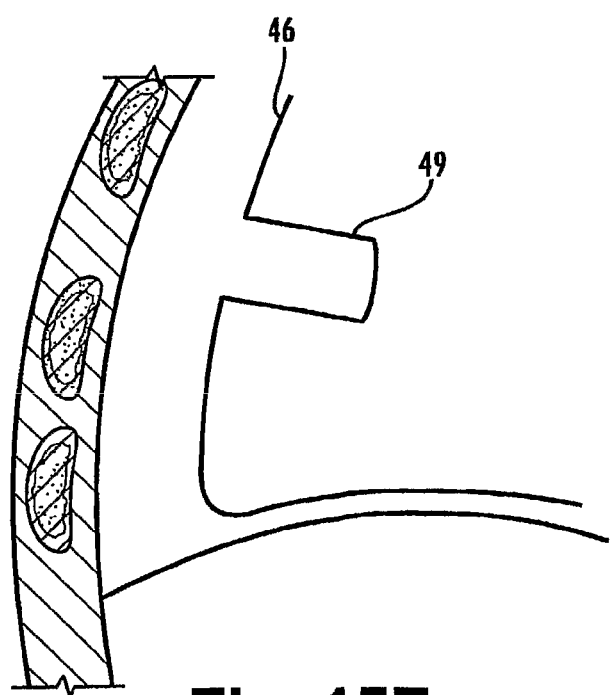

FIGS. 15A-F illustrate a method for obtaining a biopsy of lung tissue 46 using the biopsy tool 7, in accordance with the present invention. The biopsy tool 7 is advanced through the target tissue 43, a shown in FIG. 15A. The snare 81 is advanced beyond the needle distal end 85 and the snare head 82 is deployed, as shown in FIG. 15B. The target tissue 43 is therefore, between the snare head 82 and the operator. The needle 80 is slidably withdrawn along the snare shaft 84 and removed there from, leaving the snare 81 in place, as shown in FIG. 15C. One or more hollow needles 80A, 80B of increasing outer diameter, respectively, are advanced and withdrawn along the snare shaft 84 to adjacent the snare head 82 and adapted to dilate a larger tract 49 by cutting through the lung tissue 46 to the target tissue 43, as shown in FIGS. 15D and 15E. The tract having been dilated to at least the diameter of the target tissue 43, the target tissue 43 is excised and the snare 81 removed, as shown in FIG. 15F. A tract 49 cored from the lung tissue 46 can be left as is to heal or sealed to prevent bleeding and/or air leakage, as provided below.

In another embodiment of a method of the present invention, the patient has specific lung abnormality imaged. A needle 80 is passed through the chest wall and into and just beyond the lung abnormality to be biopsied, target tissue 48, such as a lung nodule or an abnormal tissue. In an embodiment, the needle 80 has a tip that imparts energy to the tissue to cauterize or seal the tissue as the needle 80 is advanced. A securing or anchoring mechanism is deployed from within the needle just beyond the nodule. In one embodiment, the securing mechanism is attached to a guide wire within in the needle and running from the proximal part of the needle to the distal securing or anchoring location. From within needle, the expandable member is advanced just beyond the nodule. The expandable member comprises a cutting mechanism that when pulled backwards towards the operator, is adapted to cut a diameter of tissue that includes the nodule. In an embodiment, as the cut occurs, the tissue is sealed with an energy mechanism, such as, but not limited to, RF, Laser, HIFU, polymer sealant. The cutting member comprises a catch assembly attached to its inner diameter. The needle is removed over a wire and a series of dilating sheaths are advanced and retracted to dilate the tract up to the desired diameter. In an embodiment, each dilating sheath contains a distal tip with a mechanism to impart energy to seal the tissue as it dissects the channel. As the cutting member is pulled back towards the operator, a core of tissue that contains the nodule is excised and deposited into a catch assembly. Once the catch assembly contains the biopsy material, it is pulled in close proximity to the sheath which compresses the material to a smaller volume to aid in extraction through the tissue. Once the tract is sufficiently dilated, the catch assembly containing the biopsy material is extracted by pulling towards the operator. In another embodiment, as the catch assembly is extracted, the tissue tract is impregnated with sealant I the form of laying a core of sealant that fills the tract and prevents tissue bleeding or air leak.

FIGS. 16A and 16B are side cross-sectional and front views of needle 80A, 80B, respectively, suitable for advancing along the snare shaft 84 and cutting a tact in the tissue, in accordance with an embodiment of the present invention. The needle 80A, 80B comprises an outer tube 90 with an outer tube lumen 97, an inner tube 94 coaxial with the outer tube 90, and a plurality of blades 95 there between. The blades 95 couple with and space apart the inner tube 94 with the outer tube 90 within the outer tube lumen 97. The outer tube 90 includes an outer tube distal edge 91 that is suitable for cutting through tissue. The inner tube 94 includes an inner tube distal edge 93 that is suitable for cutting through tissue. The blade 95 includes a blade distal edge 96 that is suitable for cutting through tissue. The inner tube lumen 94 is adapted to slidingly receive the snare shaft 84 such that the needle 80A, 80B can track over the snare shaft 84 to the target tissue. Tissue cut by the outer tube distal edge 91, the inner tube distal edge 93, and the blade distal edge 96 is contained within the outer tube lumen 97 as the needle 80A, 80B is advanced through the tissue.

In an embodiment, the needle 80A, 80B comprises means for cauterizing the tissue as it is cut, such as, but not limited to, RF energy.

In an embodiment of the methods in accordance with the present invention, the tract 49 is plugged with a biodegradable material so as to seal and promote healing of the lung tissue 46. In another embodiment of the methods of the present invention, the tract 49 is compressed closed. In another embodiment, the tract 49 is sutured closed. Where drainage is required, in another embodiment, a drainage tube is placed in the tract 49 and in communication with the peritoneal space to provide for drainage.

In another embodiment in accordance with the present invention, one or more of the hollow needles of increasing diameter incorporate means for sealing the tissue. The hollow needles may incorporate means for sealing the tissue, including, but not limited to, RF, laser, cryo, among other.

In an embodiment in accordance with the present invention, methods and apparatus are adapted to sample a very specific nodule within the lung parenchyma. In accordance with an embodiment of a method of the present invention, the nodule or specific localized interstitial abnormality is localized. It is anticipated that a number of image guidance techniques can be combined with these methods to localize the abnormality.

In an embodiment of the present invention, a patient is placed in a CT scanner and the nodule is imaged. Using standard CT guided interventional techniques commonly used in CT guided biopsy of the lung, the biopsy tool 7 is advanced through the skin, chest wall, pleural space and lung and through to the target tissue 43 to be sampled. Once the distal end of the biopsy tool 7 is passed through the nodule or interstitial abnormality, a snare in the form of a compressed wire hook, such as that comprised of shape memory metal such as Nitinol, is advanced out of the distal end of the needle 80. Once the snare head 82 is advanced out of the needle, it expands to a predetermined configuration just beyond the target tissue 43.

In an embodiment, the snare head 82 has the shape of a three pronged treble hook 83. At the base of the hook 83 is the snare shaft 84, comprising, such as, but not limited to, guide wire, nylon, braided cotton string, and other flexible filaments. The needle 80 is removed, leaving the attachment filament intact in the tract to the treble hook now just beyond the target tissue 43. Once the needle 80 is removed, the operator pulls on the snare shaft 84. This engages the treble hook 83 to the target tissue, with the snare shaft 84 traversing the target tissue 43, nodule or interstitial structure, to be sampled. Once the snare shaft 84 and treble hook 83 are engaged with the target tissue 43, a sheath is passed over the snare shaft 84 and the target tissue 43 viewed with the imaging device, such as, but not limited to, CT, MRI, Ultrasound, and Fluoroscopy.

By way of example, but not limited thereto, in one embodiment the patient has a specific lung abnormality imaged. Possible techniques to image the lung include, but not limited to, CT, Ultrasound, Fluoroscopy, MRI, PET, and PET/CT. The needle 80 is passed through chest wall into and just beyond the lung abnormality to be biopsied, such as a lung nodule. In an embodiment, a needle 80 is provided comprising a tip adapted to impart energy to the tissue to cauterize or seal the tissue as it is advanced. From within the needle 80, an expandable snare 81 is extruded just beyond nodule. The expandable snare 81 is attached to a snare shaft 84, such as, but not limited to, a guide wire or guide filament, that is within the needle 80. The needle 80 is removed, leaving the snare shaft 84 coupled to the snare head 82 in place. A sheath is passed over the snare shaft 84 to dilate the track through the tissue to the distal end just before the target tissue. More than one sheath can be utilized to progressively dilate the tract. A sealing mechanism can be utilized as the tract is developed to the target tissue. Once the tract is developed to sufficient diameter, the dilating sheath is replaced with a sheath that has a distal end that can core out the target tissue or the tissue around the target tissue, and lock into the snare head 82 just beyond the area to be encompassed between the distal end of the sheath and the snare head 82. The snare head 82, now locked into the distal end of the sheath and encompassing the biopsy material, target tissue 43, the assembly is pulled back towards the operator. As the assembly is withdrawn, the surrounding tissue is cauterized. As this is done an inner channel of the guide sheath, now connected to the expandable member is utilized to deliver tissue sealant material or core plugs to fill the space and prevent air leakage.

In another embodiment of a method of the present invention, the patient has specific lung abnormality imaged. A needle 80 is passed through the chest wall and into and just beyond the lung abnormality to be biopsied, target tissue 43, such as a lung nodule. In an embodiment, the needle 80 has a tip that imparts energy to the tissue to cauterize or seal the tissue as the needle 80 is advanced. A snare head 82 is deployed from within the needle just beyond the target tissue. In an embodiment, the snare head 82 is attached to a snare shaft 84 that runs through the length of the needle 80. From within needle, the expandable member is advanced just beyond the nodule. The expandable member comprises a cutting mechanism that when pulled backwards towards the operator, is adapted to cut a diameter of tissue that includes the nodule.

In an embodiment, as the cut occurs, the tissue is sealed with an energy mechanism, such as, but not limited to, RF, Laser, HIFU, polymer sealant. The cutting member comprises a catch assembly attached to its inner diameter. The needle is removed over a wire and a series of dilating sheaths are advanced and retracted to dilate the tract up to the desired diameter. In an embodiment, each dilating sheath contains a distal tip with a mechanism to impart energy to seal the tissue as it dissects the channel. As the cutting member is pulled back towards the operator, a core of tissue that contains the nodule is excised and deposited into a catch assembly. Once the catch assembly contains the biopsy material, it is pulled in close proximity to the sheath which compresses the material to a smaller volume to aid in extraction through the tissue. Once the tract is sufficiently dilated, the catch assembly containing the biopsy material is extracted by pulling towards the operator. In another embodiment, as the catch assembly is extracted, the tissue tract is impregnated with sealant I the form of laying a core of sealant that fills the tract and prevents tissue bleeding or air leak.

Figure 17A:
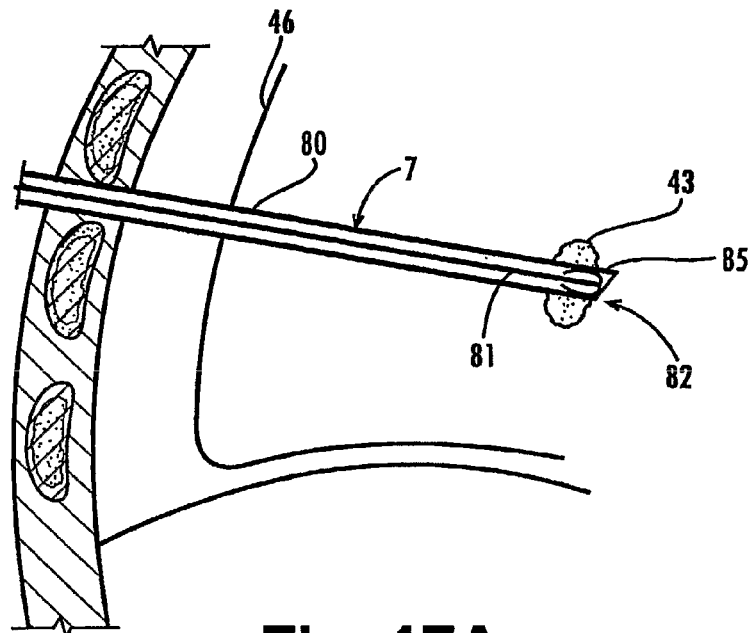
FIGS. 17A-E illustrate a method for obtaining a biopsy of lung tissue using a biopsy tool in combination with a pull-type cutting device, in accordance with an embodiment of the present invention.
Figure 17B:
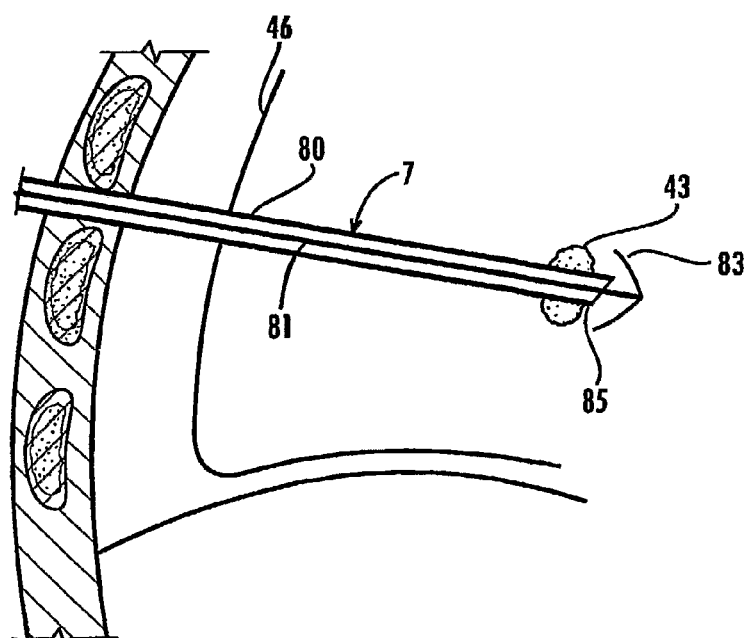
Figure 17C:
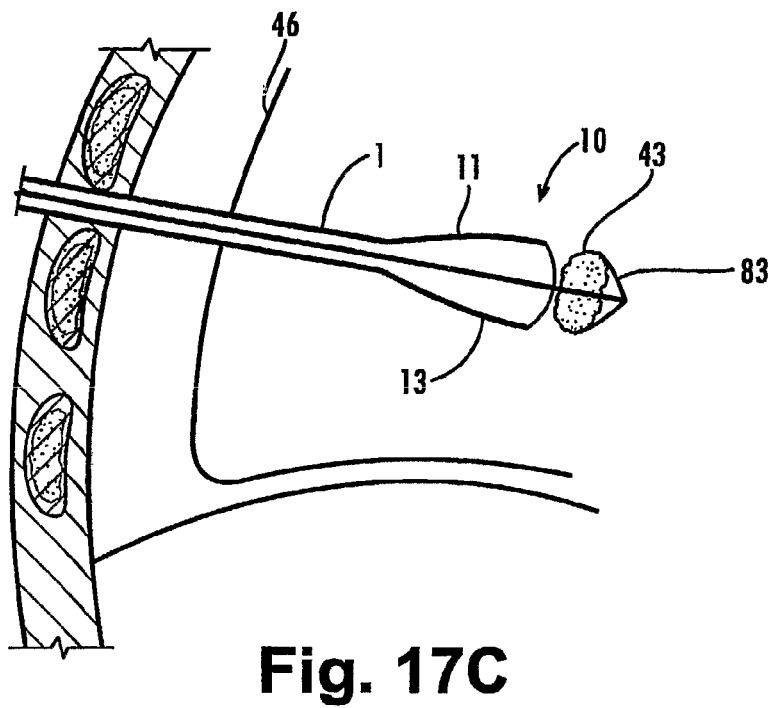
Figure 17D:
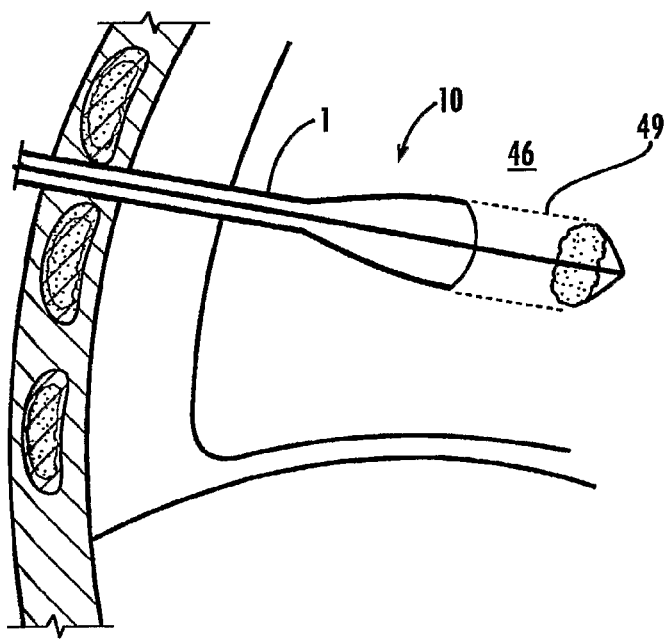
Figure 17E:
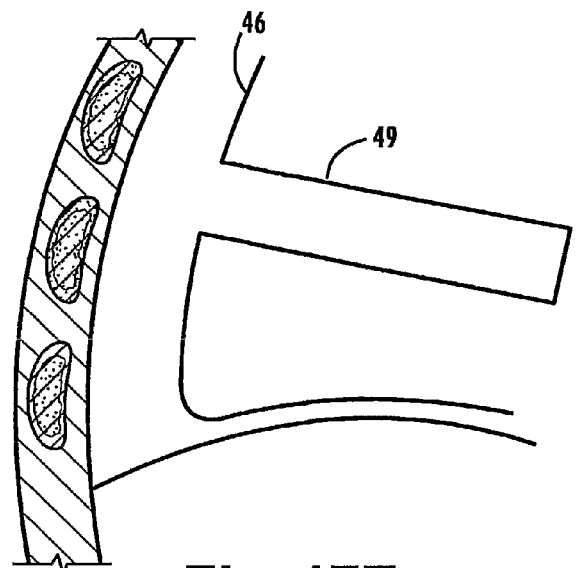

FIGS. 17A-E illustrate a method for obtaining a biopsy of lung tissue 46 using the biopsy tool 7 of the embodiment of FIGS. 14A and 14B, in combination with the pull-type cutting device 1 of the embodiment of FIG. 2, in accordance with an embodiment of the present invention. The biopsy tool 7 is advanced through to the target tissue 43, a shown in FIG. 17A. The snare 81 is advanced beyond the needle distal end 85 and the snare head 82 is deployed, as shown in FIG. 17B. The target tissue 43 is therefore, between the snare head 82 and the operator. The needle 80 is slidably withdrawn along the snare shaft 84 and removed there from, leaving the snare 81 in place. The pull-type cutting device 1 is slidably advanced along the snare shaft 84 such that the cutting head 10 is adjacent the target tissue 43. The expandable portion 13 including the cutting portion 11 is deployed, as shown in FIG. 17C. The pull-type cutting device 1 is pulled toward the operator cutting a tract 49 into the lung tissue 46, as shown in FIG. 17D. The tract 49 having been made to at least the diameter of the target tissue 43, the target tissue 43 is excised and the snare 81 removed, as shown in FIG. 17E. A tract 49 cored from the lung tissue 46 can be left as is to heal or sealed to prevent bleeding and/or air leakage, as provided below.

A variety of biopsy techniques commonly employ a small bore needles to sample tissue deep within an internal organ, or the surrounding lymph nodes for the diagnosis of cancer and other diseases. One major limitation is the amount of tissue, and thus the quantity and quality of the tissue sample for analysis. It is desirable to sample larger tissue specimens, but there are a number of difficulties in introducing large bore devices into an organ or lymph node to obtain a larger tissue sample with better preserved tissue architecture. Furthermore, while it is possible to stick a needle into most body organs with an acceptable, but not negligible complication profile, as the diameter of the access device goes up, so does the complication rate. This is especially the case in the lung, where it is desirable to sample lung nodules that are less than 1.5 cm, but the risk of bleeding and air leakage is significant. Furthermore, the proximity of major vascular structures in the lung, liver, and other locations makes the process of pushing large diameter cutting elements into the body dangerous. It is therefore also desirable to gain access deep within a solid organ or body space containing lymph nodes without endangering the tissues and vital structures around the target tissue for biopsy.

In one embodiment of the invention an instrument is provided whereby a small bore needle is advanced to a target tissue, such as a lung nodule deep in the lung, using image guidance. The needle passes through the desired tissue, and a catch and stabilization element is actuated. The nodule is secured, and cut free. With the nodule now free, the catheter traversing the specimen has the following features. The distal tip has a sealing mechanism that can include laser, RF, other energy sources, or a mechanism to deliver specific tissue sealants or plugs. Just proximal to the tissue specimen, mounted on the catheter, is an expandable cutting member that when expanded exposes a cutting element on the proximal side. The operator pulls the device back towards the outer surface of the body, along the original needle tract. As the operator pulls back, the tissue is cut, making a precisely cut channel so that the biopsy specimen, which is larger than the original needle tract, can be pulled out through the newly cut channel. As the tract is cut, the catch device enclosing the biopsy specimen is pulled out, the distal end of the catheter is utilized to seal the tract left behind.

FIGS. 18A and 18B are a side cross-sectional and end view of a pull-type cutting device 8 in a deployed or expanded configuration, in accordance with an embodiment of the present invention. The pull-type cutting device 8 comprises a shaft 20 having a shaft distal end 22 and a shaft proximal end 21 and a lumen 23 extending there through. Disposed about the shaft distal end 21 is a cutting head 100. The cutting head 100 comprises an expandable portion 113 having a cutting portion 111 proximal from the shaft distal end 22. The expandable portion 113 is in fluid communication with a fluid lumen 25 which is adapted to supply fluid to the expandable portion 113 so as to inflate the expandable portion 113. The lumen 23 is adapted to pass over a guide wire or snare shaft 84. Extending from the cutting portion 111 are a plurality of stand-off blades 116 supporting a loop cutting element 112. Examples of cutting elements 112 include, but are not limited to, blades, radiofrequency, laser, and electrocautery cutting elements, that are adapted to create an incision when pulled against and through tissue. As the pull-type cutting device 8 is pulled through the tissue, the cutting element 112 cores the tissue, wherein the core of tissue can be pushed out by the subsequent pull-out of the snare 80, substantially as shown in FIG. 17D. Since the pulling and cutting action is towards the operator, this results in an improved safety profile as it lessens the risk that an internal organ or other structure can be damaged as the body space opening is created. In an embodiment, any pieces of cut tissue are deposited into cavity 115.

Figure 18C:
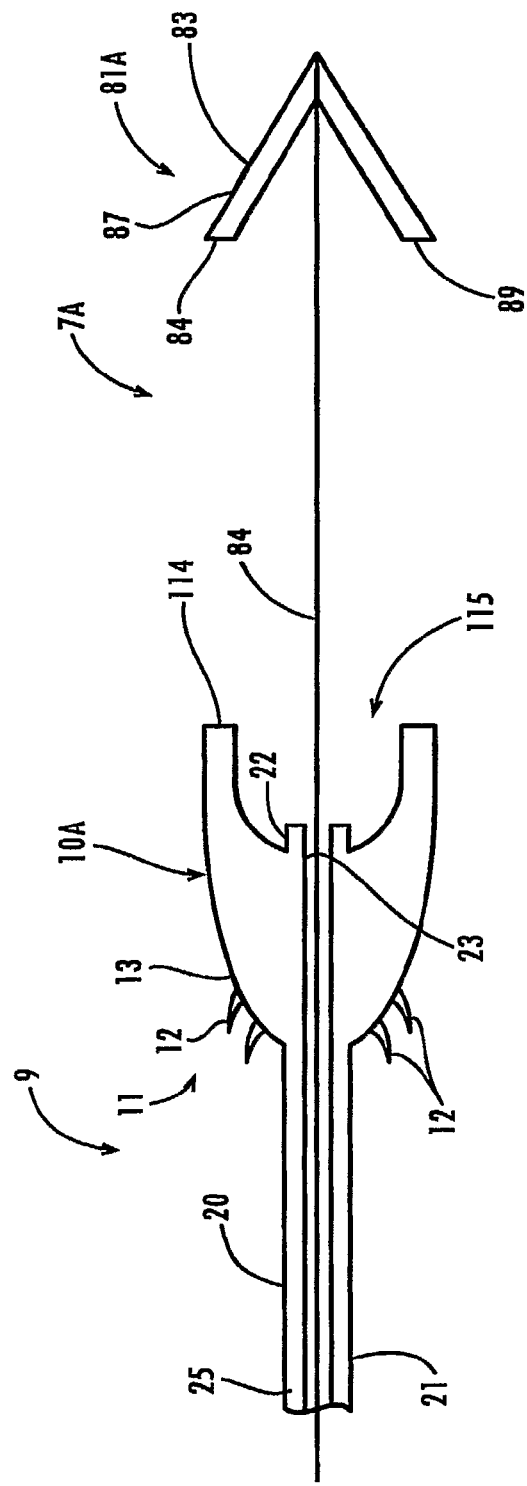
FIGS. 18C and 18D are side cross-sectional views of a pull-type cutting device in a deployed or expanded configuration and a snare, in accordance with an embodiment of the present invention.
Figure 18D:
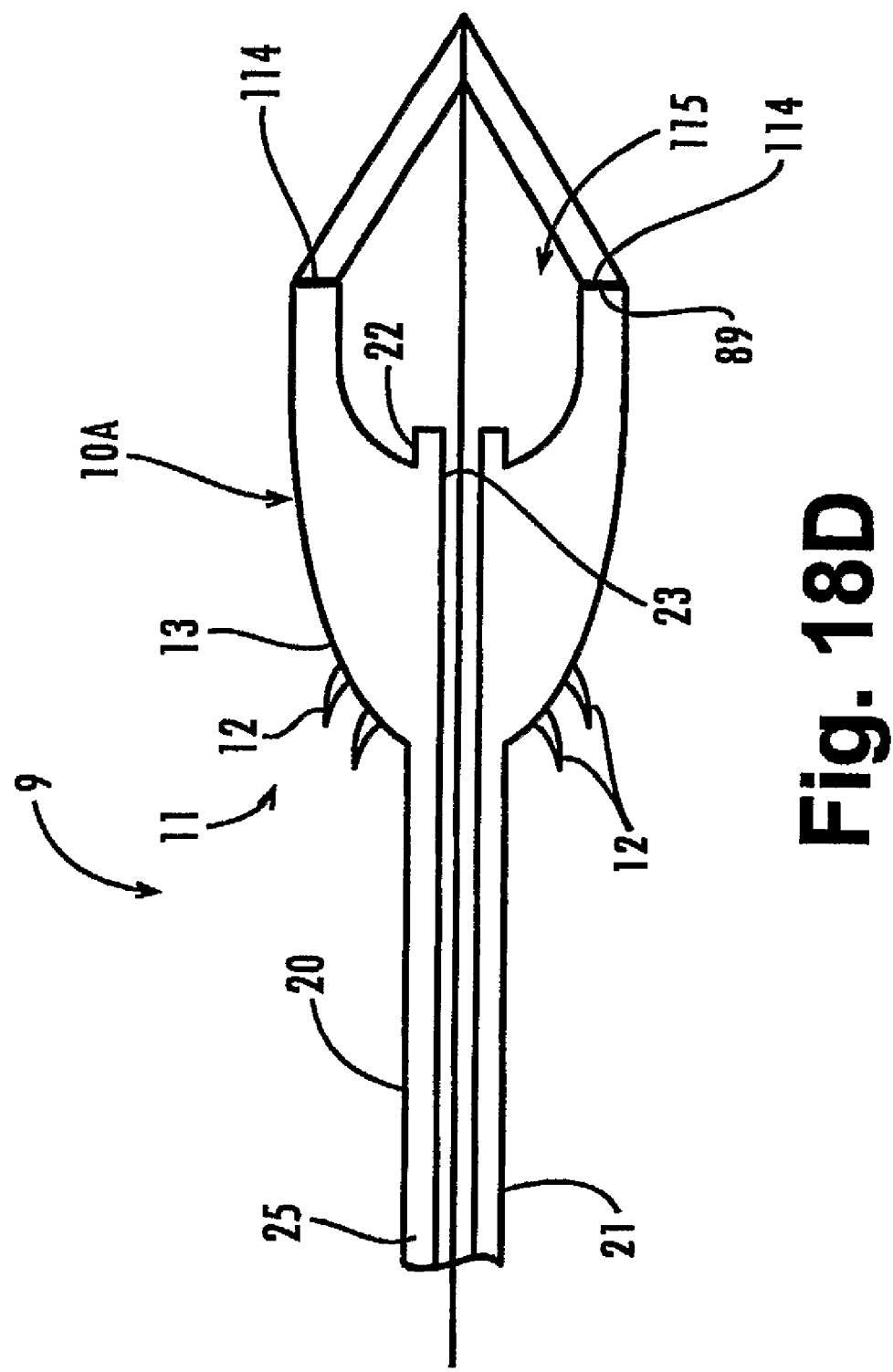

FIGS. 18C and 18D are side cross-sectional views of a pull-type cutting device 9 in a deployed or expanded configuration and a snare 81A, in accordance with an embodiment of the present invention. The pull-type cutting device 9 comprises a shaft 20 having a shaft distal end 22 and a shaft proximal end 21 and a lumen 23 extending there through. Disposed about the shaft distal end 21 is a cutting head 10A. The cutting head 10A comprises an expandable portion 13 having a cutting portion 11 proximal from the shaft distal end 22. The expandable portion 13 is in fluid communication with a fluid lumen 25 which is adapted to supply fluid to the expandable portion 13 so as to inflate the expandable portion 13. The lumen 23 is adapted to pass over a guide wire or snare shaft 84. At the shaft distal end 22, the expandable portion 13 defines a cavity 115. Extending from the cutting portion 11 are a plurality of cutting elements 12. Examples of cutting elements 12 include, but are not limited to, blades, radiofrequency, laser, and electrocautery cutting elements, that are adapted to create an incision when pulled against and through tissue. As the pull-type cutting device 9 is pulled through the tissue, the cutting elements 12 cut through the tissue. The snare 81A comprises a snare head 83 having a proximal end 89 comprising a coupling element. The expandable portion distal end 114 comprises a coupling element adapted to couple with the coupling element on the snare head proximal end 89, as shown in FIG. 18D. The snare head 83 further comprises a sealing element 87 adapted to seal the tissue as it is drawn past and through tissue.

Figure 17F:
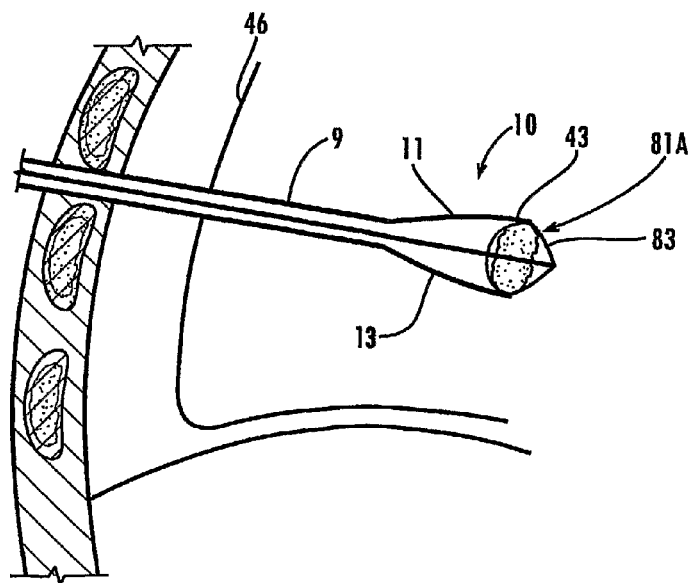
FIGS. 17F-17G illustrate a method for obtaining a biopsy of lung tissue using the biopsy tool in combination with a pull-type cutting device, in accordance with an embodiment of the present invention.
Figure 17G:
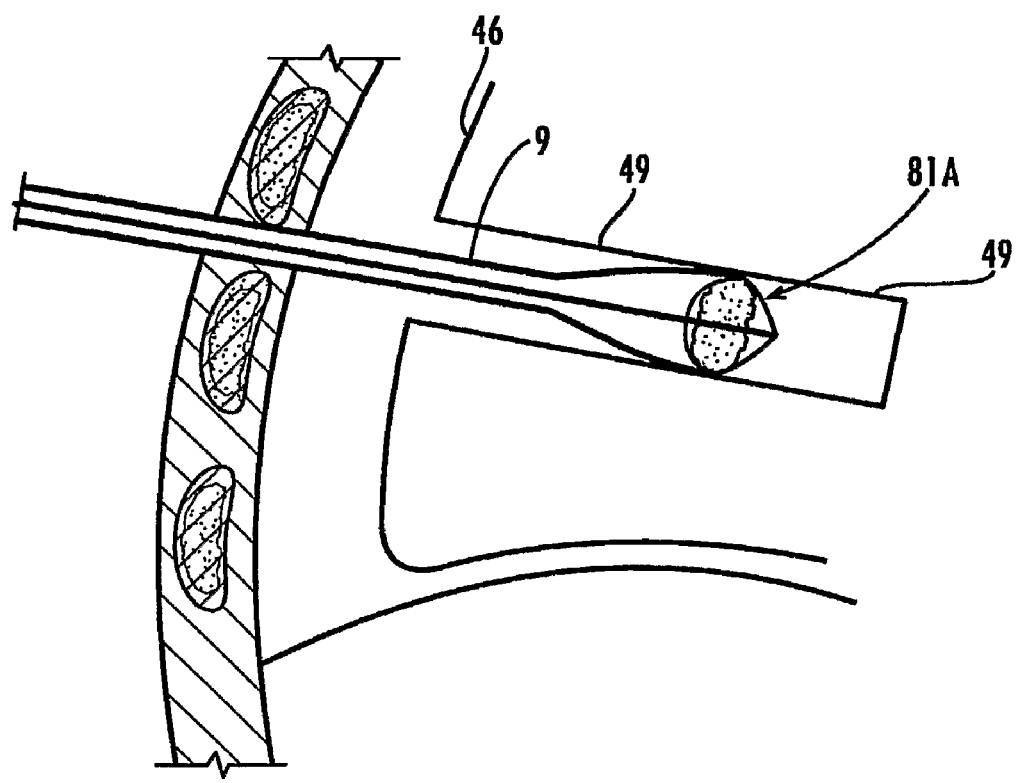

Referring again to FIGS. 17A-17B and FIGS. 17F-17G illustrate a method for obtaining a biopsy of lung tissue 46 using the biopsy tool 7,7A of the embodiment of FIGS. 14A and 14B and FIGS. 18C and 18D, in combination with the pull-type cutting device 9 of the embodiment of FIGS. 18C and 18D, in accordance with an embodiment of the present invention. The biopsy tool 7 is advanced through to the target tissue 43, as shown in FIG. 17A. The snare 81A is advanced beyond the needle distal end 85 and the snare head 82 is deployed, as shown in FIG. 17B. The target tissue 43 is therefore, between the snare head 82 and the operator. The needle 80 is slidably withdrawn along the snare shaft 84 and removed there from, leaving the snare 81A in place. The pull-type cutting device 9 is slidably advanced along the snare shaft 84 such that the cutting head 10 is adjacent the target tissue 43. The expandable portion 13 including the cutting portion 11 is deployed, as shown in FIG. 17F. The snare 81A is pulled towards the cutting head 10A with the snare head proximal end 89 placed into engagement with and coupled to the expandable portion distal end 114. The pull-type cutting device 9 and the snare 81A are pulled as a unit toward the operator cutting a tract 49 into the lung tissue 46, as shown in FIG. 17G. The tract 49 is sealed by the activation of the sealing element 87 on the snare 81A to prevent bleeding and/or air leakage.

In the following embodiments of methods in accordance with the present invention, any of the previous methods may be taken to gain image guided access to the target tissue, dilate the tract, excise the target tissue, and pull the target tissue out through the dilated tract. After the procedure, there remains a tissue tract or channel deep into the lung which potentially can bleed and leak air.

In an embodiment, a method and device is provided to drain the tract 49 while it heals from the dissection, dilation and excision from the body wall, through the pleural space to the lung parenchyma. As the lung is penetrated with the needle, and as the tract 49 is dilated and the target tissue excised, the cut surface of the lung parenchyma is prone to bleed when blood vessels are cut, and leak air when airways are cut. The method and device are adapted to provide hemostasis (no bleeding) and pneumostasis (no air leaking).

Figure 19:
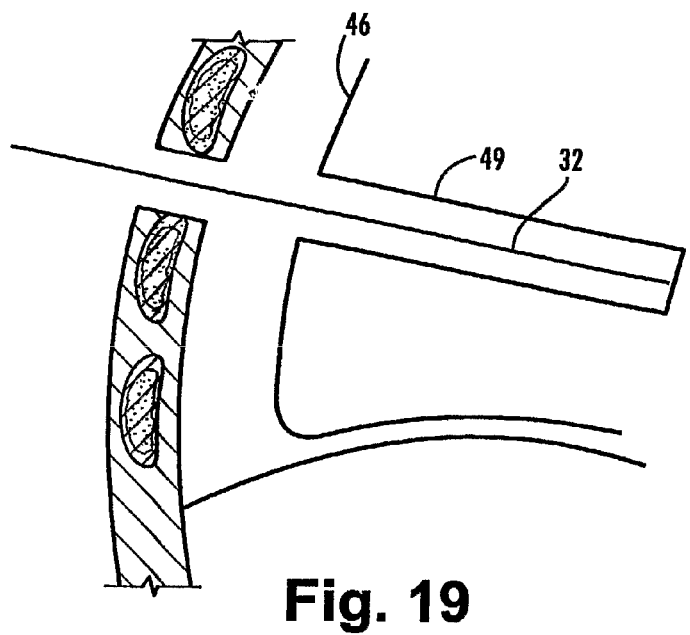
FIG. 19 is a side cross-sectional view of a tract in body tissue made in accordance with an embodiment of the present invention.

In accordance with the methods provided above, target tissue is excised resulting in a tract 49 in the tissue, as shown in FIG. 19. Upon removal of the biopsy device, a guide wire 32 is left behind in the tract 49. The guide wire 32 can be placed in the track 49 by passing the guide wire 32 through a guide wire lumen in the biopsy device, such as a guide wire lumen provided in the snare shaft 84, an accordance with an embodiment of the snare shaft 84.

Figure 20:
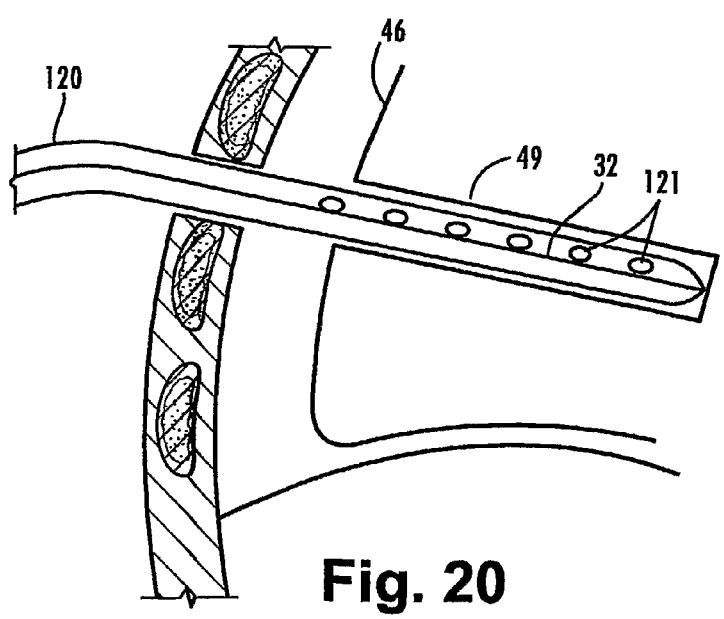
FIG. 20 is a cross-sectional view of a body space tube that has been advanced over a guide wire left in the tract after the target tissue has been extracted, in accordance with an embodiment of the present invention.

FIG. 20 is a cross-sectional view of a body space tube 120 that has been advanced over the guide wire 32 left in the tract 49 after the target tissue is extracted, in accordance with an embodiment of the present invention. The body space tube 120 comprises a plurality of apertures 121 that are positioned in the tract 49 in the lung tissue 46. The body space tube 120 is left in the tract 49 and attached to a suction apparatus to provide suction to the lung and pull the tissue in close apposition to the body space tube 120. Over a period of time, the lung tissue extraction tract 49 heals, and any blood or air is exited through the tube to an external receptacle, such as, but not limited to, a chest tube canister.

In an embodiment of the present invention, the external receptacle has a mechanism to insert a test strip into the line of air and fluid drainage, and if the test strip reacts with carbon dioxide, the color changes. If no carbon dioxide is present, the test strip does not change. The sample of gas/liquid is taken from within the pleural space to determine if air, containing carbon dioxide, is leaking out of the cut surface of the internal diameter of the tract. If it is, the tube needs to stay in place. If it is not, the tube can be removed.

This method and apparatus has applications beyond use with the lung, such as, but not limited to, cases where a chest tube is used and the question is if an air leak remains.

In an embodiment of the present invention, the body space tube 120 is biodegradable and can be cut off at the skin and left in situ.

In another embodiment of the present invention, the body space tube 120 is made of a pro-inflammatory substance that encourages inflammation and tissue in growth to limit potential for subsequent hemothorax, pneumothorax or bronchopleural fistula.

In an embodiment, the body space tube 120 is a very thin filament with multiple channels on the side. The multi channel filament left behind in the tissue tract and placed to an external suction source to drain any blood and air from the biopsy tract while the healing process takes place.

In another embodiment of the present invention, the tube with multi channels to the surrounding tract is filled with a porous sponge-like material. Suction is applied to the external lumen of the tube. The tissue around the tube is sucked down onto the tube. The porous sponge-like material keeps the lung and coagulum, fibrous material, and other material from clogging the internal diameter of the small tube while the tissue around it heals.

In another embodiment of the present invention, the body space tube 120 is drained internally to the bronchus, esophagus or peritoneal space.

Figure 21A:
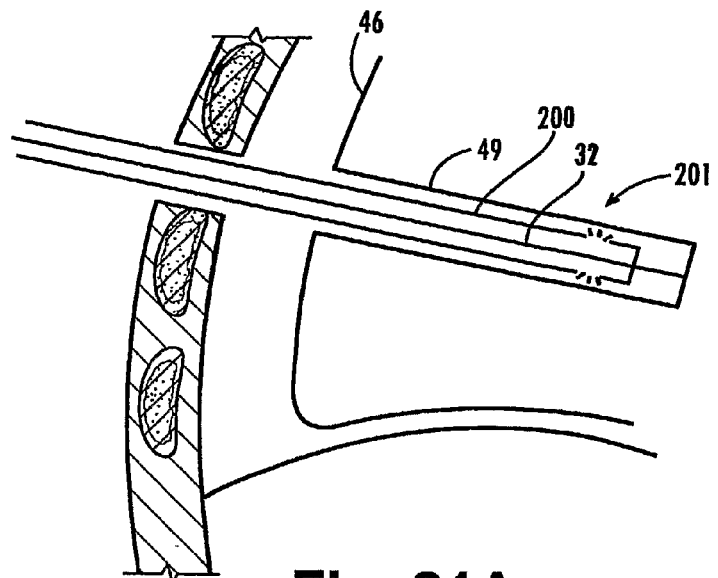
FIGS. 21A and 21B are side cross-sectional views of sealing devices, in accordance with embodiments of the present invention.

FIG. 21A is a side cross-sectional view of a sealing device 200, in accordance with the present invention. In an embodiment of the present invention, after the target tissue is extracted and a guide wire 32 is left behind in the tract 49, a sealing device 200 is passed over the guide wire 32 into the lung tissue tract 49. The sealing device 200 comprises a distal tip 201 that can impart physical energy, such as that associated with RF or Laser. Examples include, but are not limited to, diode laser, a laser of any of a number of frequencies designed to impart heat to the surrounding tissue that seals the tract. Another example provides a distal tip 201 comprising a cryogenic mechanism adapted to seal the tract 49 using cryoablation. The distal tip 201 is actuated and pulled back towards the operator. As it is pulled back the energy is imparted to the surrounding tract 49 and the tract 49 is burned and sealed, preventing the egress of blood or air.

In another embodiment, since there is no fluid in the tract 49 to be sealed, fluid is expelled through the distal tip 201 as the fluid heated with RF (i.e. Tissuelink Wet Electrode) or laser (so that the fluid becomes heated beyond the temperature of the surrounding tissue) and the tissue is sealed. The combination of the fluid and the RF seals the surrounding tissues and prevents the leakage of blood, air, lymph tissue, etc.

In another embodiment of the present invention, the sealing mechanism is contained on the outer lumen of a balloon tipped catheter. The balloon is expanded to fill the tissue tract and as the balloon is retracted towards the operator, the energy is imparted to the surrounding tissue and the tissue is sealed.

Figure 21B:
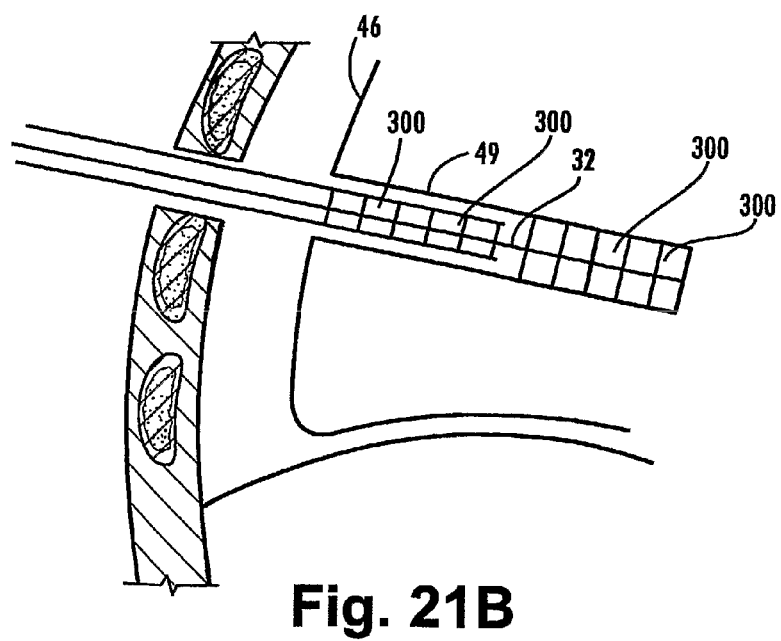

FIG. 21B is a side cross-sectional view of a sealing device 200, in accordance with the present invention including a tissue sealing substance is extruded to fill the tract 49. In an embodiment the tissue sealing substance is a polymer that increases in size or generates heat as it is actuated with an activating substance, such as external ultrasound.

In another embodiment, a spiral suture is wrapped around just under the surface of the tract 29 as it is weaved in a spiral fashion around the tract 49, and then actuated in such a fashion that the tract is pulled down upon itself and closed so there is no remaining space for blood or air to escape. In other embodiments of the present invention, other mechanisms are actuated to pull the walls of the tract down upon itself, eliminating the space for blood or air to escape.

Figure 22A:
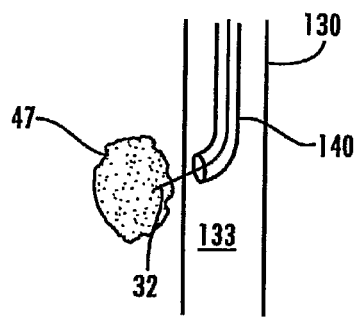
FIGS. 22A-F illustrate a method for obtaining a biopsy of target tissue that is adjacent a body lumen using embodiments of biopsy tools provided above, and a method for sealing the body lumen after the target tissue, or a portion thereof, is excised, in accordance with an embodiment of the present invention.
Figure 22D:
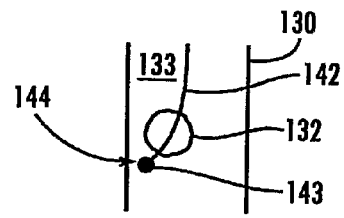
Figure 22B:
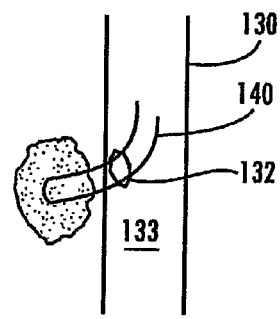
Figure 22E:
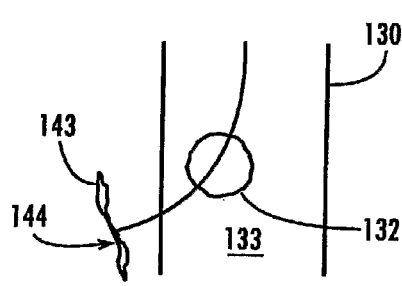
Figure 22C:
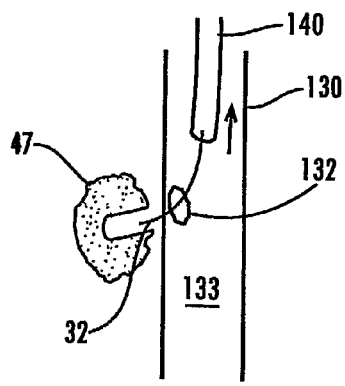
Figure 22F:
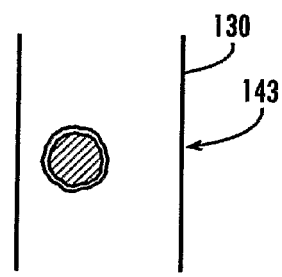

FIGS. 22A-F illustrate a method for obtaining a biopsy of target tissue 47 that is adjacent a body lumen 130, such as, but not limited to, the esophagus and bronchus, using embodiments of biopsy tools 140 provided above, and a method for sealing the body lumen 130 after the target tissue 47, or a portion thereof, is excised, in accordance with an embodiment of the present invention. Using endoscopic ultrasound or other imaging techniques, a guide wire 32 is advanced through the body lumen 130, piercing the wall 133 of the body lumen 130 and placed adjacent the target tissue 47. The biopsy tool 140 is advanced along the guide wire 32 creating an aperture 132 in the body lumen 130, as shown in FIGS. 22A and 22B. The target tissue 47 is removed using methods described above and the guide wire 32 is left behind, as shown in FIG. 22C. A sealing device 142 is provided comprising an expandable sealing element 143 at a distal end 144. The sealing device 142 is advanced over the guide wire 32 with the distal end 144 passing through the aperture 132 in the wall of the body lumen 130. The expandable sealing element 143 is expanded and pulled back against the wall 133 of the body lumen 130, covering the aperture 132.

Figure 23A:
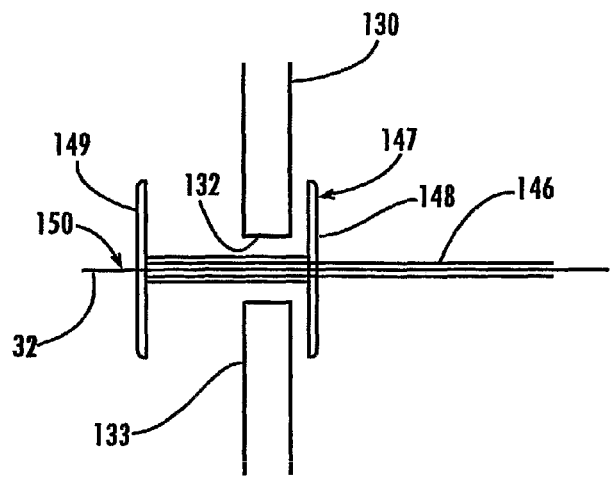
FIGS. 23A and 23B are side cross-sectional views of a sealing device adapted for sealing apertures in body lumens, in a pre-finished and finished configuration, respectively, in accordance with an embodiment of the present invention.
Figure 23B:
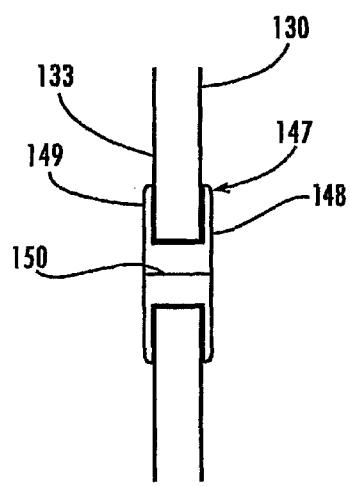

FIGS. 23A and 23B are side cross-sectional views of a sealing device 146 adapted for sealing apertures 132 in body lumens 130, in a pre-finished and finished configuration, respectively, in accordance with an embodiment of the present invention. The sealing device 146 comprises a distal end having a double-phalange plug 148. The sealing device is advanced over the guide wire 32 via a guide wire lumen 150 traversing an aperture 132 in a body lumen 130. A first phalange 149 is positioned adjacent one side of the aperture 132 and a second phalange 148 is position on the opposite side of the aperture 132. The first and second phalanges 149, 148 are brought together to impinge upon and seal the aperture 132 capturing a portion of the wall 133 adjacent the aperture 132 there between. The guide wire lumen 150 is self-sealing upon removal of the guide wire 32 there from. This embodiment can be used for esophageal perforations as well.

When a device or tube is removed from the chest, it leaves a tract from the external skin, through the chest wall to the pleural space. As the patient breaths, air can be entrained back into the pleural space, as the process breathing requires creating negative pressure within the chest relative to the external environment. When air is sucked back into the chest it creates a condition known as pneumothorax, which can be life threatening. It is generally taught to tunnel obliquely from one level to another to create a tissue flap to collapse upon itself when a tube is removed so that air cannot be sucked back into the chest. When performing thoracoscopy, however, it is desirable to tunnel directly to the pleural space, without traveling obliquely, as it facilitates the introduction and removal of the operating instruments.

In an embodiment, a method and apparatus are provided whereby a plug or series of stitches are on a wire within the chest in a compressed configuration. When it is desired to seal the pleural space, the wire is pulled back towards the operator, bringing the plug or stitches in apposition to the internal opening of the body space. The device is then actuated to insert the plug or stitches into the internal body space opening, and the wire breaks away, thereby closing the hole and preventing fluid from leaking out or air from getting sucked back in.

This embodiment could be used to seal a variety of body spaces, including surgically created internal to external port sites (such as is seen with thoracoscopy, laparoscopy), as well as to seal the bronchus, when a deep parenchymal lung biopsy is carried out from an end bronchial position. Likewise, this could be used to seal the esophagus when a transesophageal biopsy is performed, as is done for Endoscopic Ultrasound guided biopsy of mediastinal lymph nodes and other structures. This could be used for other procedures where the pleural, peritoneal or other space (GU, GYN, etc) are accessed through the gut.

One of the difficulties of CT guided biopsy of the lung is the fact that the ribs and other chest wall structures can get in the way and not provide an adequate window from which to biopsy the lung. Thoracoscopy can overcome this by starting within the pleural space, but one cannot currently localize a nodule within the lung by thoracoscopy. In this embodiment, a thoracope is fitted with an ultrasound probe on its distal tip. The tip has a lubricious covering that allows the operator to run the ultrasound probe over the surface of the lung until the nodule is localized. Once the nodule is localized, a suction apparatus around the perimeter of the ultrasound probe is actuated so that lung is sucked into the scope/probe, thus securing the area and locking the probe into place. The operator then advances a needle through the lung under ultrasound guidance to access the nodule. Then the nodulectomy can be carried out in a variety of ways, including as have been described above.

Embodiments providing methods and apparatus to excise lung tissue and nodules are presented. These embodiments are less-traumatizing than conventional biopsy approaches, and utilize a single-port, minimally invasive technique. These embodiments may be practiced in conjunction with the anesthesia and port-cutting technology described above. That technology and the associated methods can be used to provide access for carrying out a procedure to excise lung tissue as described here, using image guidance to allow precise, directed lung nodule excision. These techniques utilize suction within the pleural space and lung tissue excision tract after dilation to remove blood, air and prevent lung collapse during the procedure. The disclosed embodiments also utilize a balloon-dilation technique to dilate the entire excision tract from the port in the chest wall to the location of the nodule to be excised (for example within the lung), which provides a robust and simple approach to facilitate excision of a large sample of target tissue. Integrated sealing also is used to minimize complications of bleeding and air leak. The procedures may be performed with CT guidance. CT is particularly well suited for solid organ interventions. Recent advancement of technology has brought about CT fluoroscopy, which shows the motion of organs and devices in real time. With CT fluoroscopy the trajectory of a needle can be tracked in real time, which allows the physician to make adjustments as appropriate. This advantage has made procedures shorter with equivalent or better success rates than those with standard intermittent CT imaging, though standard CT imaging may still be used.

Figure 24:
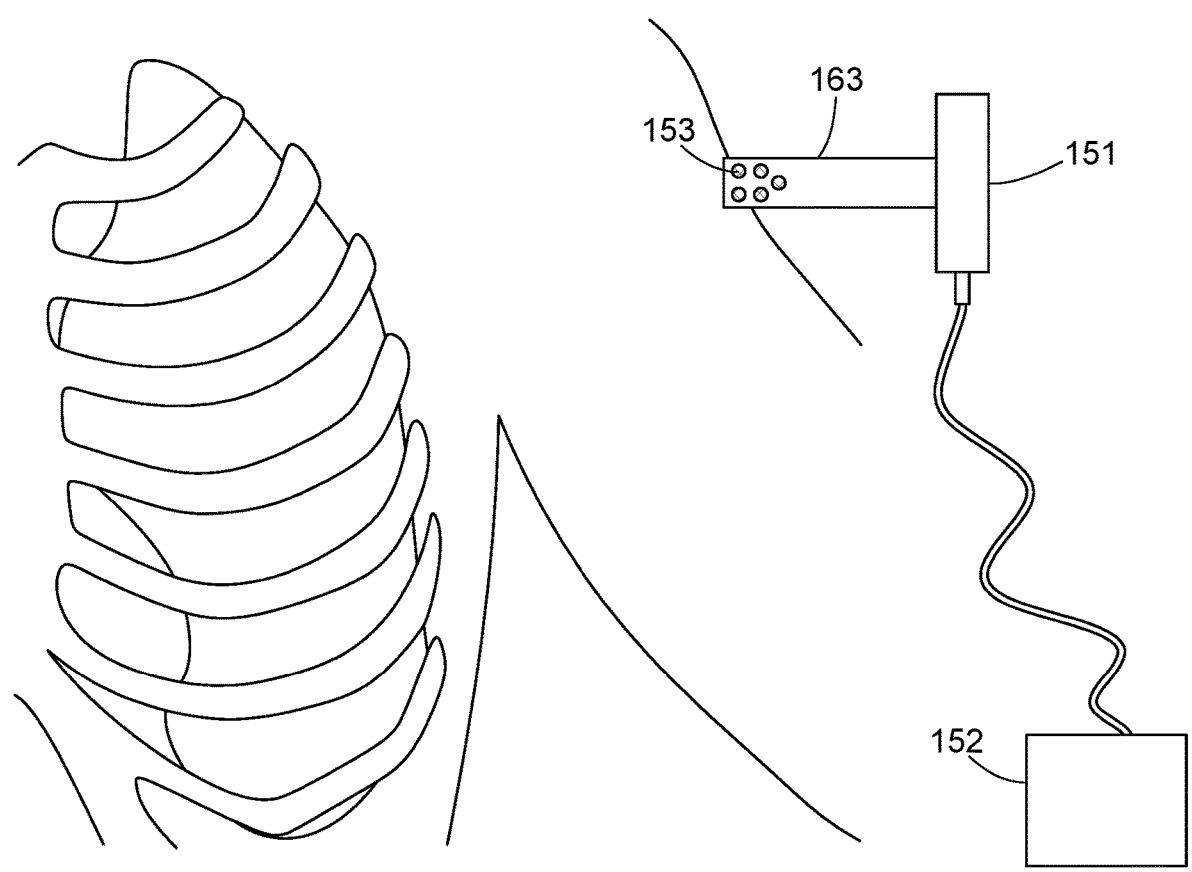
FIG. 24 illustrates a working port in communication with a vacuum source, in accordance with an embodiment of the present invention.
Figure 25:
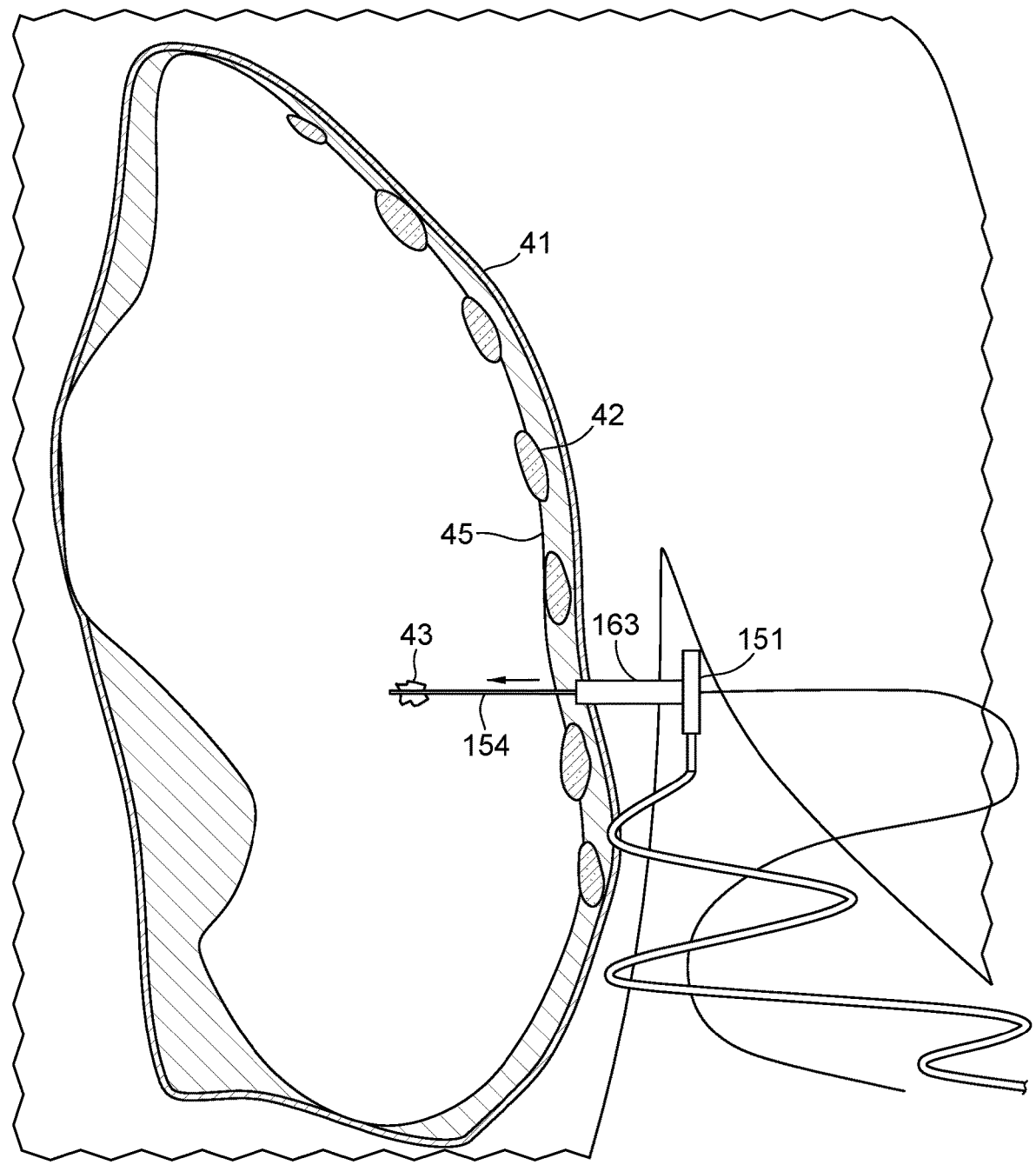

In accordance with an embodiment, a working port 151 as shown in FIGS. 24 and 25 can be introduced through an intercostal space through the chest wall to provide access to the pleural cavity of a patient. The working port 151 comprises a hollow tubular member 163 having a proximal end with one or more apertures 153, which can be inserted through an opening in the chest wall introduced via the technology and techniques described hereinabove. A distal end of the port 151 is in communication with a vacuum source 152. The vacuum source 152 can be used to drain the pleural space (between the chest wall and the lung), the lung excision tract (within the lung parenchyma), or both. The tubular member 163 is of a predetermined length such that the proximal end can extend into the chest, e.g. within the pleural space, when inserted through the opening in the chest wall and the distal end resides outside of the body. For example, the length of the tubular member 163 of the working port 151 can be 5, 10, 15, 20, or 25 cm. As the size and shape of each patient is unique, the depth that the working port 151 is inserted into the patient's chest may vary. For example, the distal (away from patient) end of the working port 151 may not be in contact with the chest wall outer surface 41 of the patient. The tubular member 163 of the working port 151 has a predetermined diameter to accommodate insertion therein of devices and surgical tools for performing an operation or surgery within the chest cavity (e.g. within the pleura), for example the devices described herein and used in the excision process here described. For example, the inner diameter of the tubular member 163 of the working port 151 can be 3, 5, 7, 10, 12, 15, 18, or 20 mm. The vacuum source 152 is coupled to the distal end of the working port 151 that resides outside of the body, and is effective to draw a vacuum on the working port 151. The resulting vacuum drawn through the aperture(s) 153 therein maintains a negative pressure within the chest to keep the lungs fully expanded during an operation. In one embodiment, the vacuum drawn through the aperture(s) 153 is −5 cmH$_2$O to −100 cmH$_2$O.

Figure 26:
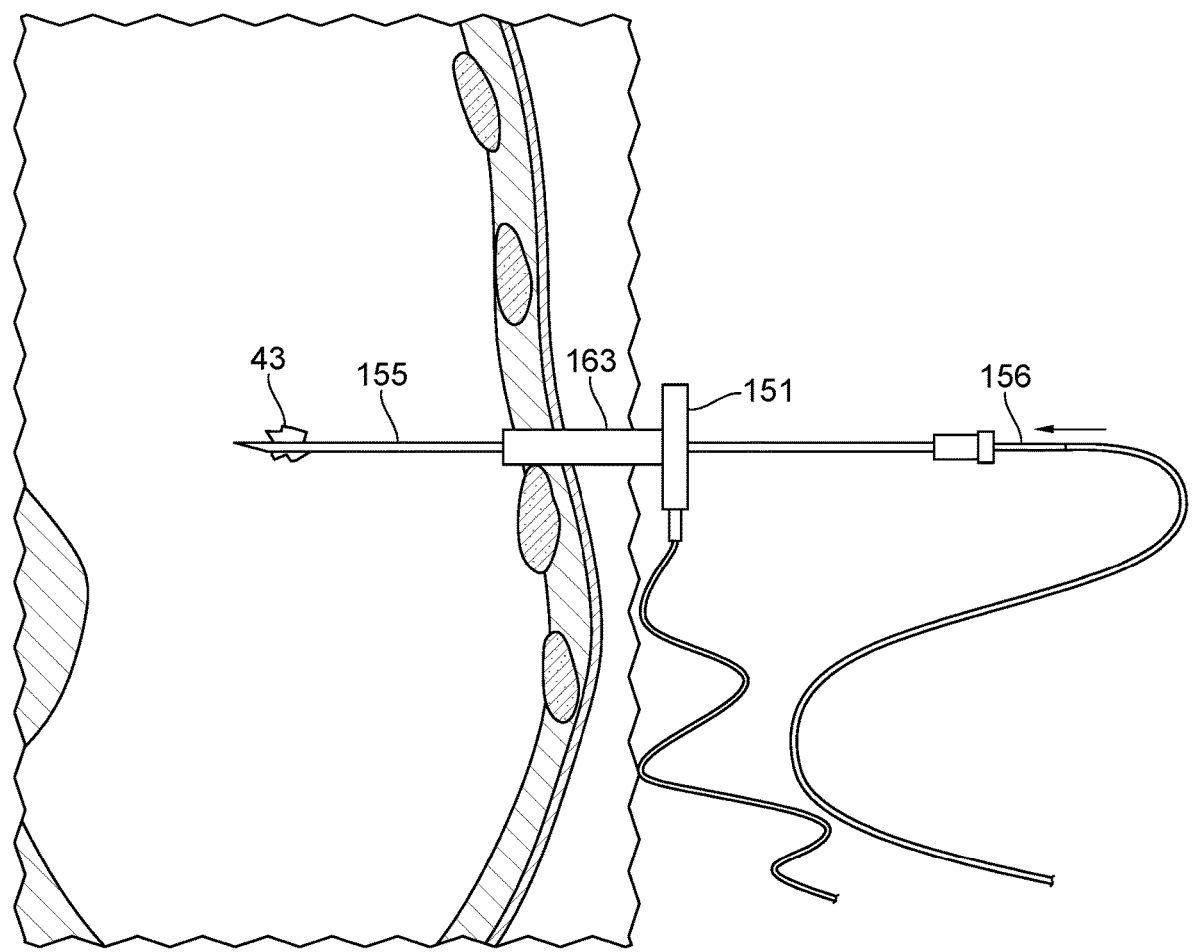

As shown in FIG. 25, in an initial stage of an exemplary procedure for excising lung tissue, first the port 151 is inserted through the opening in the chest wall as described herein, preferably until its proximal end reaches or is located in the vicinity of the pleura. Then with the port 151 installed, a needle 154 is advanced from outside the chest through the working port 151 and toward the target tissue 43 within the lung. The needle 154 is advanced until its proximal (toward patient) end has advanced through the pleura, into the lung and beyond the target tissue 43. Advancement of the needle 154 can be accomplished under CT fluoroscopy in order to track and adjust its trajectory in real time, which allows for adjustments to be made when necessary. In an embodiment, the needle 154 has a feature at its tip that imparts energy to tissue to cauterize or seal the tissue as the needle 154 is advanced. For example, the needle tip may be configured to deliver thermal, radio-frequency or electrical energy to tissue with which it comes into contact along its advance, in order to cauterize that tissue as the tip is advanced. In particular, the needle 154 may be configured as a radio-frequency transducer, or it may be connected to a voltage source to supply thermal and/or electrical energy during use. In a preferred technique, the needle 154 is inserted until its tip reaches, or preferably arrives beyond, the target tissue 43 relative to the port 151. Thereafter, as seen in FIG. 26 a trocar needle 155 is advanced through the working port 151 and over the already emplaced needle 154, which guides the trocar needle 155 along a trajectory so that its proximal end arrives adjacent, preferably beyond, the target tissue 43 relative to the port 151. In one embodiment, once the trocar needle 155 is in place the needle 154 is then withdrawn. However, the needle 154 may also remain in place to serve as a guide for later-inserted implements (i.e. an excision device, a sealing device, balloon catheters or other implements for dilation, a suction apparatus, etc.). In another embodiment, once the trocar needle 155 is in place, a guide wire can be advanced through it so the track to the target tissue is preserved for the subsequent advancement and removal for later inserted implements, for example over the guide wire. If desired, the needle 154 can be withdrawn once such guide wire is in place. In another embodiment, a guide wire is advanced through the working port 151 and over the already emplaced needle 154, which guides the guide wire along a trajectory so that its proximal end arrives adjacent, preferably beyond, the target tissue 43 relative to the port 151. In this embodiment, the guide wire itself would include a longitudinally extending bore to accommodate the needle 154 therein, and use of the trocar needle 155 is optional. Instead, the guide wire can preserve a track to the target tissue 43 for the subsequent advancement and removal of later-inserted implements.

Figure 27:
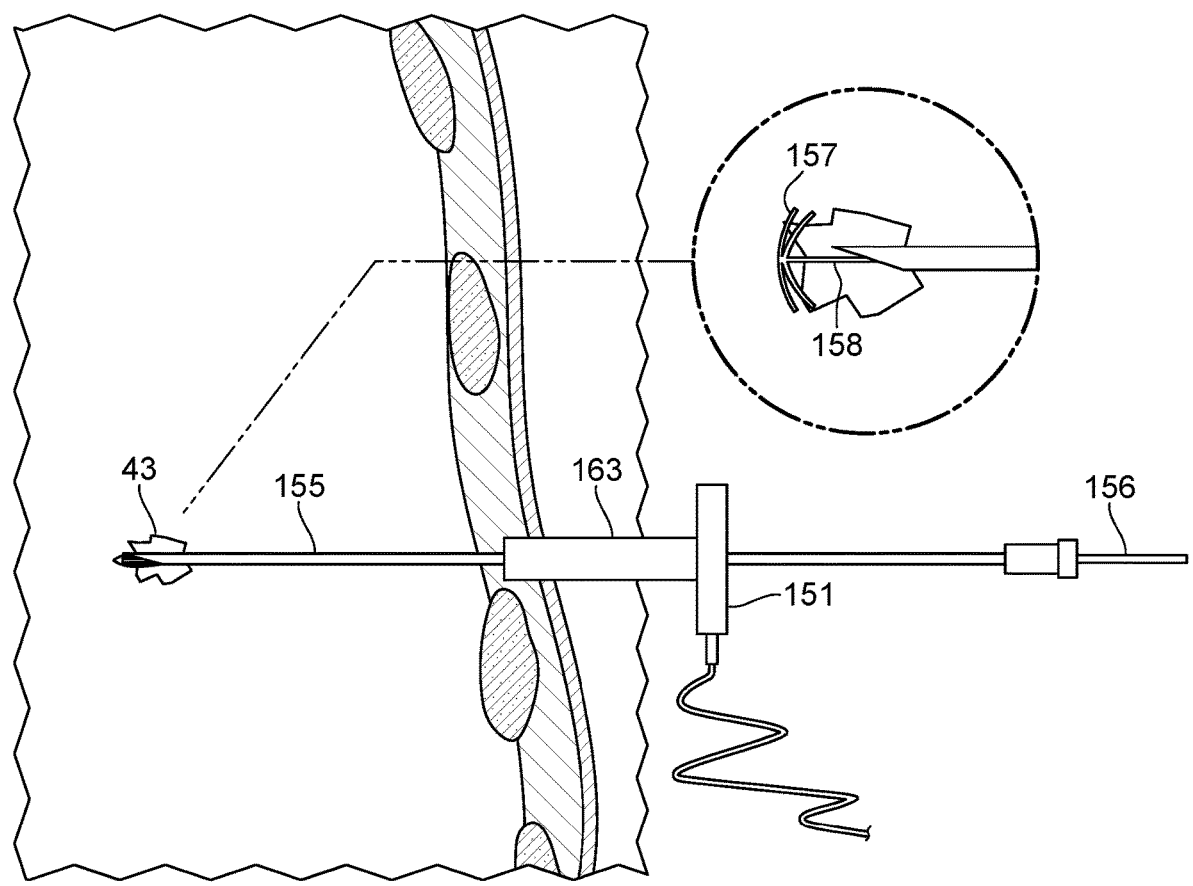

With the trocar needle 155 now in place and providing a channel from outside the patient to a location just beyond the target tissue 43, a catch wire 156 is advanced through the trocar needle 155 until its proximal end arrives just beyond the trocar needle 155 and the target tissue 43. In an embodiment, the catch wire 156 comprises (e.g.) nylon, braided cotton string, and/or other flexible filaments. At that point a tissue anchor 157 attached to or adjacent the proximal end of the catch wire 156 can be deployed as shown in FIG. 27. In an embodiment, the tissue anchor 157 is in the form of a compressed wire hook comprised of a shape memory metal such as Nitinol. In another embodiment, the tissue anchor 157 is in the form of a three pronged treble hook. Once the tissue anchor 157 of the catch wire 156 is advanced out of the trocar needle 155 and just beyond the target tissue 43 (i.e. after it is no longer constrained within the bore of the trocar needle 155), it can expand to its predetermined, deployed configuration. For example, the tissue anchor 157 can be elastically deformed to an undeployed configuration while it is constrained within the diameter of the trocar needle 155. But once advanced beyond the trocar needle 155, the tissue anchor 157 then can elastically expand to its deployed, unconstrained state as shown in the call-out in FIG. 27. The catch wire 156 is then retracted away from the target tissue 43, thereby tensioning the catch wire 156 from the target tissue 43 with the catch wire 156 being anchored from behind (i.e. the proximal side of) the target tissue 43 via the tissue anchor 157. In this manner, the catch wire 156 can be used to provide a distal (i.e. away from the patient) counterforce against subsequent operative steps that involve advancement toward the target tissue 43 from the outside (i.e. dilating, coring, etc.). The target tissue 43 is thus localized and anchored at the proximal end of a tissue-excision tract that extends from outside the body, through the pleural space, and into the lung up to the target tissue 43, using the tissue anchor 157.

Figure 28:
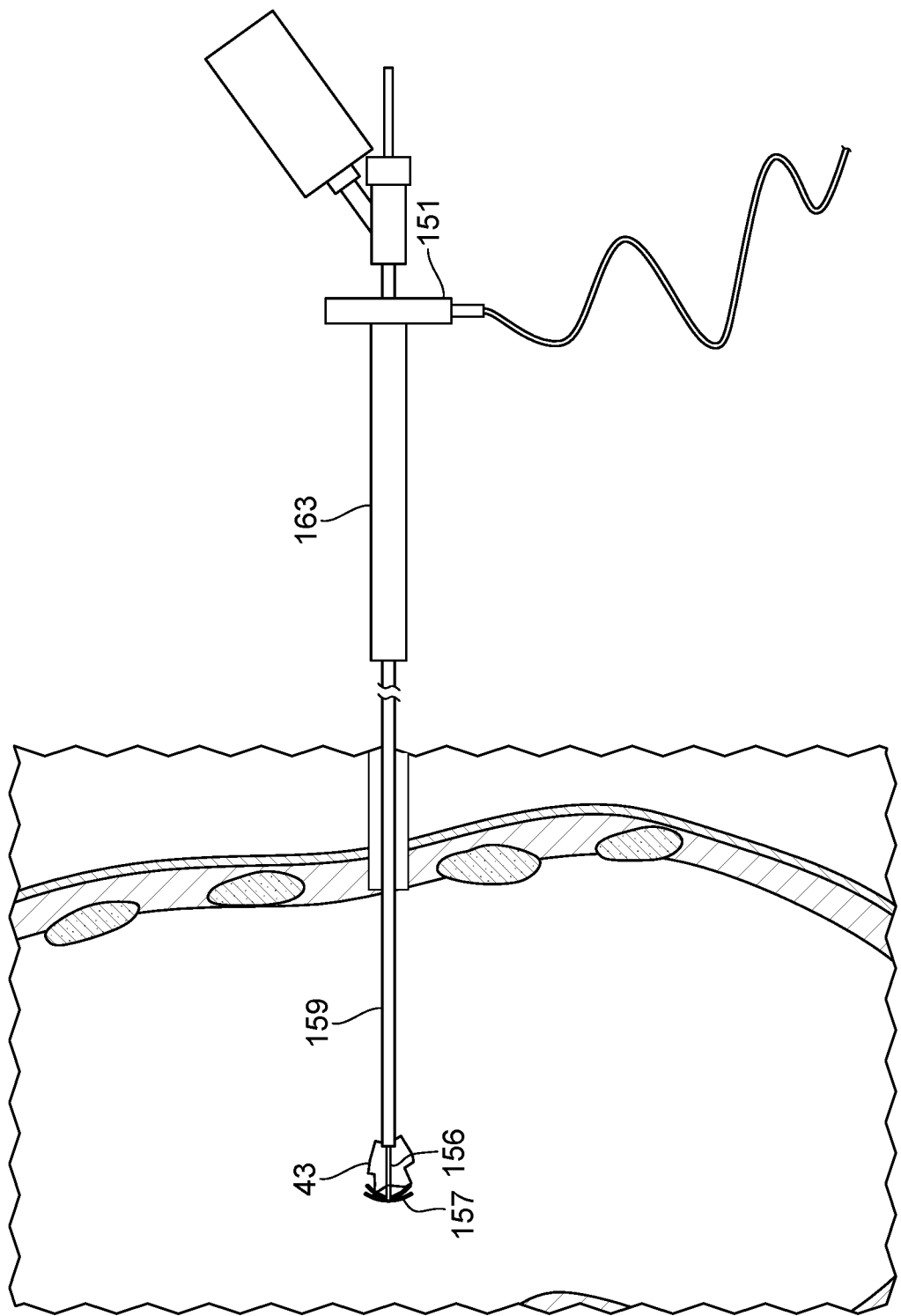

The trocar needle 155 is then withdrawn, leaving behind the catch wire 156 whose proximal end is secured at the target tissue 43 via the tissue anchor 157. A dilation catheter 159 is next advanced through the working port 151 and over the catch wire 156 against a counterforce applied by tensioning the catch wire 156 in a distal direction from outside the chest. The dilation catheter 159 is advanced through the pleural space and into the lung over the catch wire 156, up to the target tissue 43 now positioned adjacent the tissue anchor 157 as seen in FIG. 28. Optionally, as also seen in the figure the working port 151 can be withdrawn prior to insertion of the dilation catheter 159 so as not to obstruct dilation of the channel along the tissue tract between the chest wall and the target tissue 43. In other embodiments, the working port 151 remains positioned within the chest wall. The dilation catheter 159 can be a balloon catheter that extends at least from the chest wall through the pleural space and into the lung, up to the target tissue 43 along the tract followed by the catch wire 156.

The dilation catheter 159 may be a balloon catheter made of any appropriate flexible material for use as an inflation balloon, such as nylon, polyester, polytetrafluoroethylene (PTFE), latex, rubber, and mixtures thereof. In one embodiment, the dilation catheter 159 is made from a low or non-compliant material, such as for example, nylon or polyester. A low or non-compliant catheter will increase in diameter by up to a maximum of about 5% of its unexpanded diameter in response to increasing the pressure for inflating the dilation catheter 159 to 5, 10, 15, 20, 25, 30, 35, or 40 atmospheres. Alternatively, the dilation catheter 159 may be made from a hybrid or highly compliant material where the diameter of the balloon may increase as much as about 40% during inflation. The hybrid or highly compliant dilation catheter 159 may proportionally increase in diameter in response to increases in inflation pressure which may allow for fewer balloon sizes to be used. In one embodiment, the inflated dilation catheter 159 has an outside diameter of 1 mm to 30 mm, preferably 3 mm to 25 mm, more preferably 5 mm to 20 mm, and more preferably 8 mm to 15 mm. In any event, it is desirable that the dilation catheter 159 dilate the tract to a greater overall diameter than the target tissue to be excised; preferably up to 5%, 10%, 15%, or 20% greater than the target-tissue diameter.

The dilation catheter 159 may be coated with a pharmacologic material, an anti-thrombogenic material, prothrombogenic material, an anti-infective material, anti-neoplastic material, radiation, any material used to seal tissue or any combination of these.

A carbon dioxide sensor can be positioned on the dilation catheter 159 to sample gas/liquid within the pleural space to determine if air (containing carbon dioxide) is leaking out of the lungs, which may indicate an unintended puncture or laceration of an airway or an improper or incomplete seal at the point where the catheter or other operative instruments penetrate the lung to reach the target tissue 43 therein.

Figure 29:
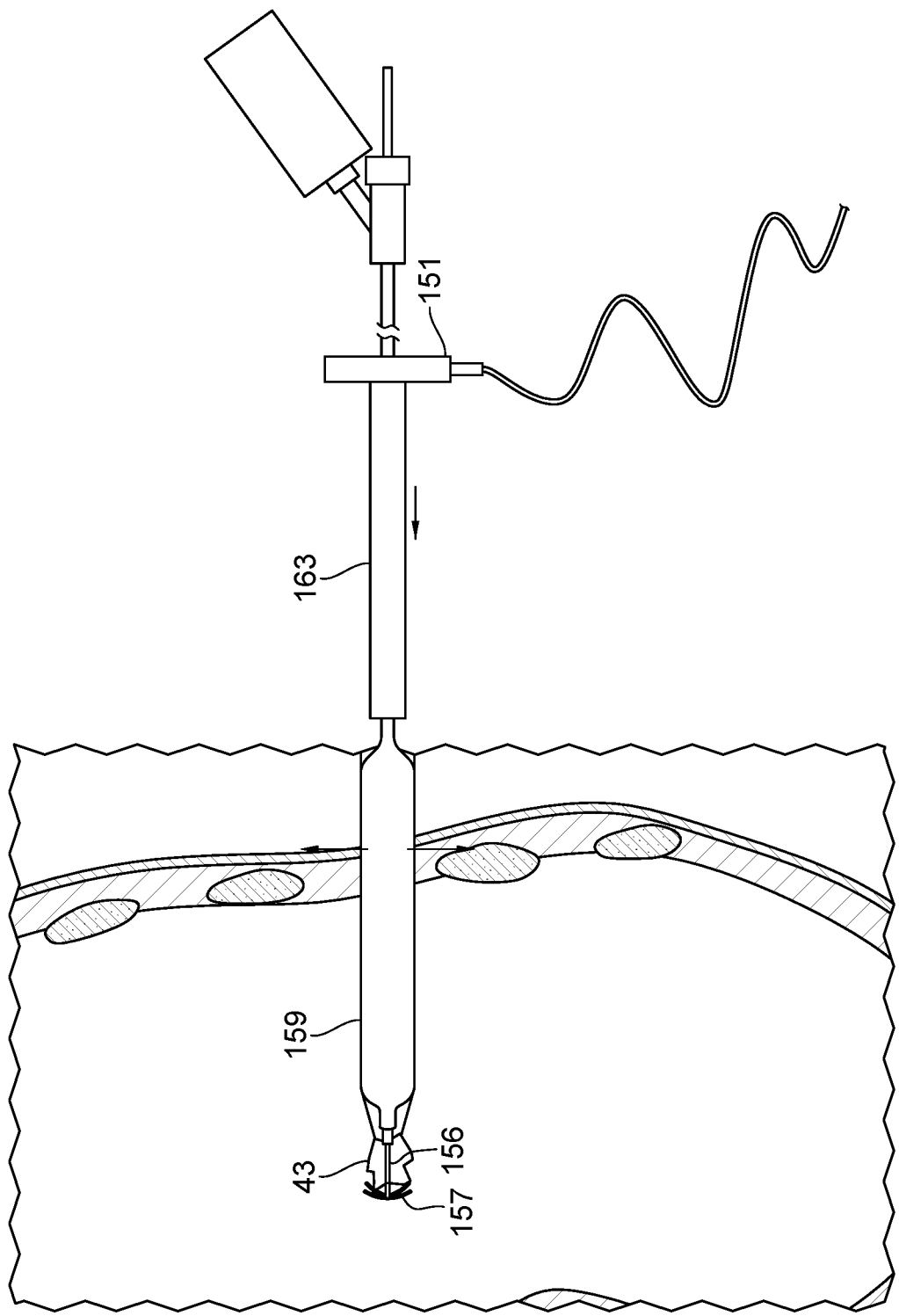

As shown in FIG. 29, the dilation catheter 159 is inflated to dilate a channel along the tissue tract from the chest wall to the target tissue 43. The diameter of the channel corresponds to the inflation diameter of the dilation catheter 159. The dilation catheter 159 is adapted to communicate inflation fluid to the expandable (balloon) portion thereof so as to inflate and deploy the expandable portion to a desired diameter for the channel, corresponding to a particular inflation pressure. That is, the inflation pressure can be continually increased until the desired channel diameter has been achieved. In an embodiment, an ablation device (not shown) is provided on the outer surface of the dilation catheter 159. As the dilation catheter 159 inflates, the ablation device introduces energy to the surrounding tissue to stem bleeding and seal against air leakage while expanding the tissue tract.

Figure 30:
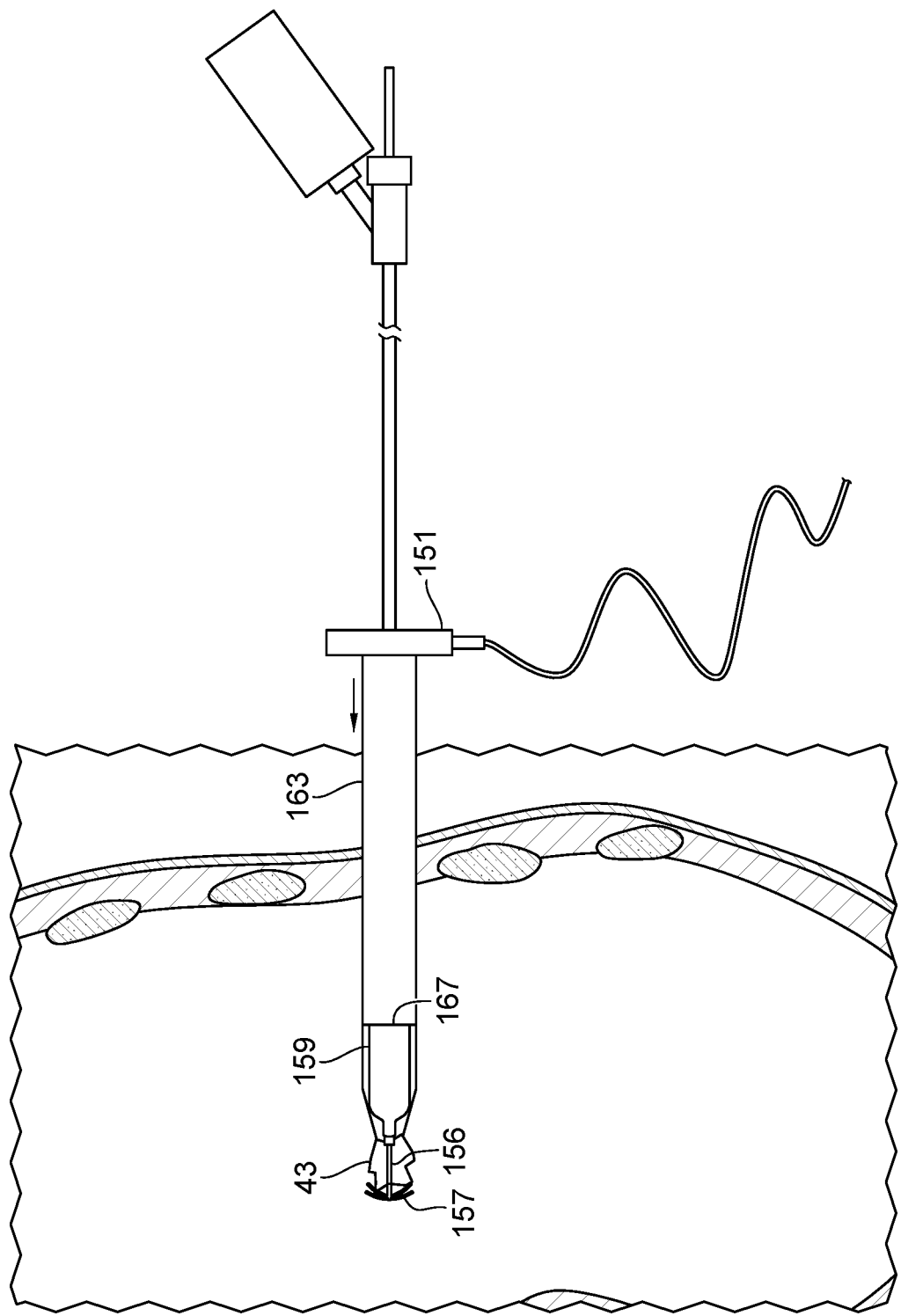
Figure 31:
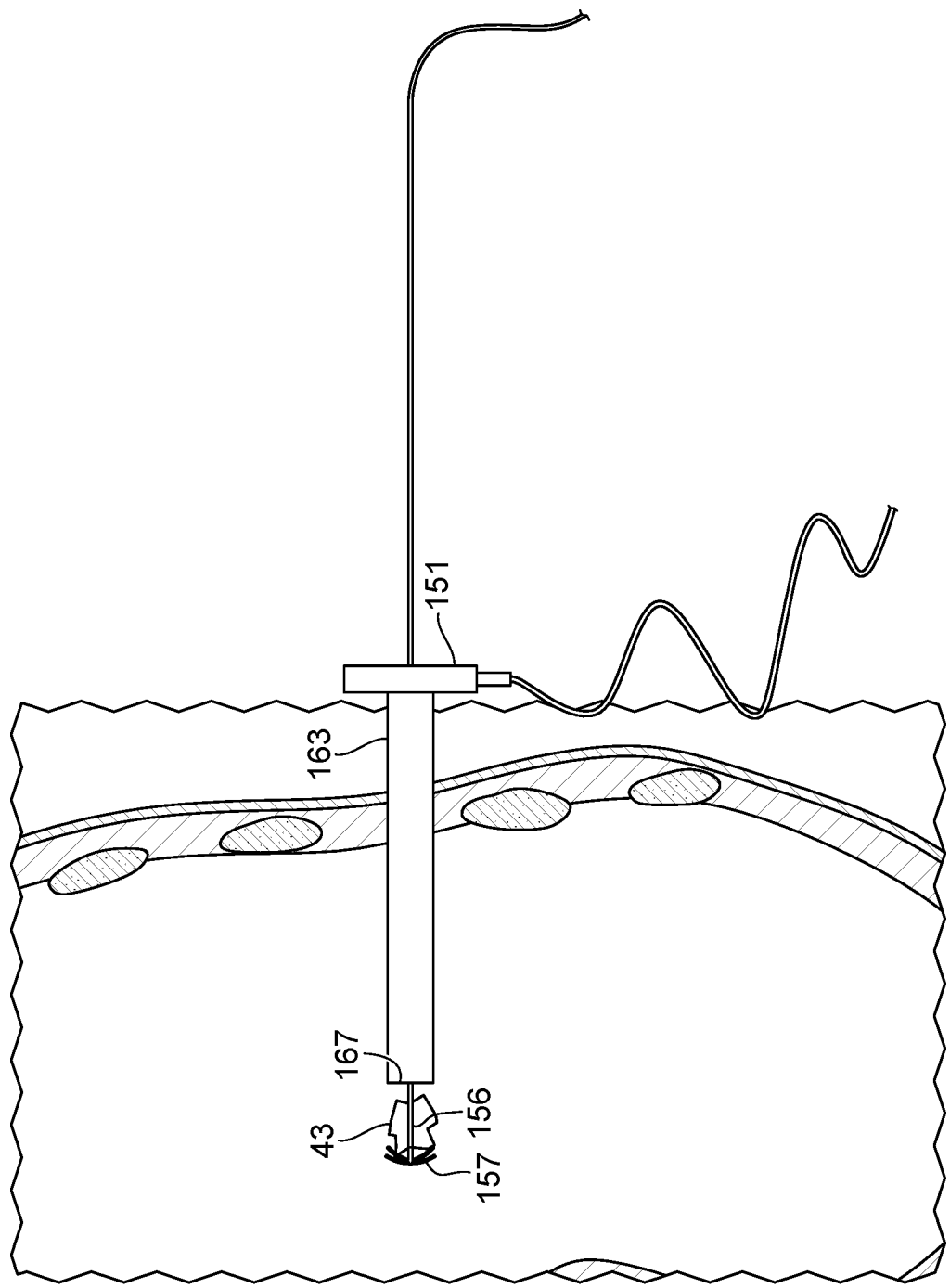

Once the desired channel diameter has been achieved by any form of dilation, a cylindrical sleeve, for example the tubular member 163 of the working port 151, can be advanced over the dilation catheter 159 until the proximal end thereof is positioned adjacent the target tissue 43 within the lung, through the pleura and the adjacent portion of the lung along the tissue tract leading from the chest-wall opening as shown in FIGS. 30 and 31. In an embodiment, the proximal end of the tubular member 163 of the working port 151 has a sharpened edge 167 to facilitate advancement thereof over the inflated dilation catheter 159 and past the surrounding tissue, through the pleural space and into the lung up to the target tissue 43. After that tubular member 163 (or other sleeve) is advanced to the target tissue 43, the dilation catheter 159 is deflated and withdrawn from the patient, leaving behind a fixed-diameter channel extending from the opening in the chest wall all the way to the target tissue 43 to be excised. The vacuum provided at the aperture (s) 153 of the working port 151, in addition to maintaining negative pressure in the pleural space, also draws the tissue tract against the working port 151 to facilitate prevention of air leak leading to lung collapse or bleeding prior to sealing.

In another embodiment, once the desired tissue-tract diameter has been achieved the dilation catheter 159 is deflated and withdrawn from the patient without or prior to the emplacement of any sleeve about the dilation catheter. The tubular member 163 of the working port 151 can be advanced through the open tract until the proximal end thereof is positioned adjacent the target tissue 43 within the lung, through the pleura and the adjacent portion of the lung along the tissue tract leading from the chest-wall opening. In an embodiment, the proximal end of the tubular member 163 of the working port 151 has a sharpened edge 167 to facilitate advancement thereof, through the pleural space and into the lung up to the target tissue 43. Notably, although a dilation catheter is disclosed for dilating the tissue tract, other modes of dilation also could be used; for example the successive advancement of increasingly larger diameter needles as disclosed in earlier embodiments.

Figure 32:
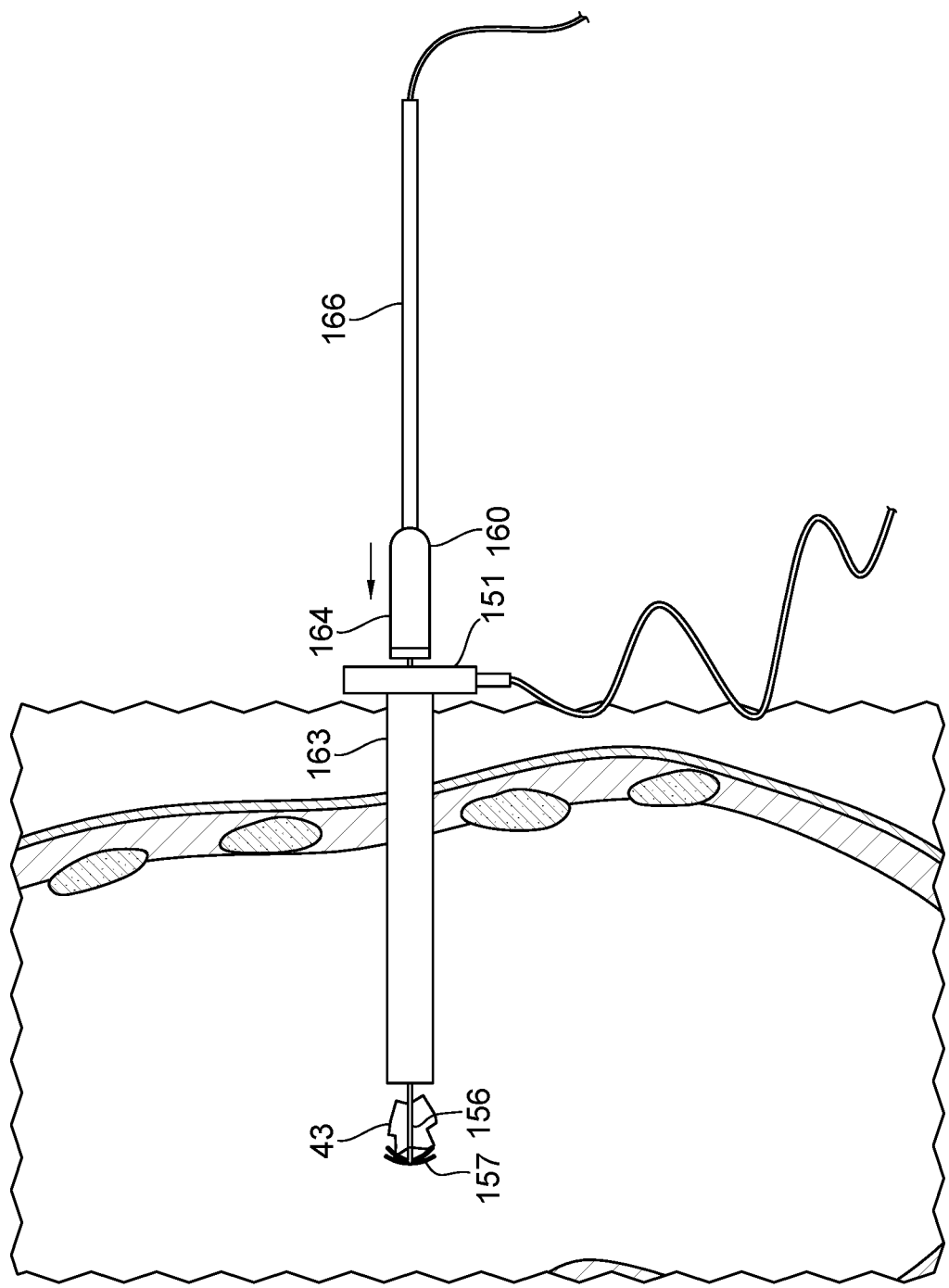

An excision device 160 is then advanced through the tissue tract (e.g. a fixed-diameter channel provided by the tubular member 163 of the working port 151 or other sleeve, or within an unsheathed tract if no sheath or sleeve is emplaced), over the catch wire 156, until it reaches the target tissue 43 as shown in FIGS. 32-34. The excision device 160 is advanced against the distal counterforce exerted against the target tissue 43 from behind by tensioning the catch wire 156, which is fixed to the target tissue 43 by the tissue anchor 157. This prevents the target tissue 43 from being pushed further into the patient by advancement of the excision device 160, possibly toward larger vascular or airway structures. It also fixes the target tissue 43 in place to assist in the subsequent coring step.

Preferably the excision device 160 comprises a hollow tubular member or sleeve 164 that terminates in a sharp circumferential cutting edge 165 at its proximal end, which is advanced toward the target tissue 43. In this manner the sleeve 164 of the excision device 160 is configured to core out a plug of tissue via simultaneous advancement and rotation through the tissue. The excision device 160 preferably is connected at its distal end to a rigid actuation rod 166 by which it is advanced from outside the body, and can be rotated via rotation of the actuation rod 166. To excise the target tissue 43, the excision device 160 is advanced through the fixed-diameter sleeve (e.g. the tubular member 163 of the working port 151) until its sharpened cutting edge 165 arrives adjacent the target tissue 43. Preferably the diameter of its tubular member 164 (and that of the surrounding sleeve) has (have) been selected to accommodate at least a portion of the target tissue 43, more preferably the full dimensions of the target tissue 43 as well as some surrounding tissue. Upon arriving adjacent the target tissue 43, the excision device 160 can be alternately rotated clockwise and counterclockwise via manipulation of the actuation rod 166 from outside the body, while simultaneously pressing it forward toward the target tissue 43 against the counterforce applied thereto by tensioning the catch wire 156. By this operation, the sharpened edge 165 of the excision device 160 makes a circular slice of the tissue surrounding the target tissue 43, and is advanced over the target tissue 43 through that slice, preferably until its proximal cutting edge reaches the tissue anchor 157. At that point the excision device 160 has cored out the target tissue 43 as well as some surrounding tissue, with the core located within the hollow tubular member 164 of the excision device 160. The target tissue 43 then is excised and removed from the body by simultaneously withdrawing both the catch wire 156 and the excision device 160 through the fixed-diameter channel (or through the tissue tract if no fixed-diameter sleeve was placed), through the opening in the chest wall to the outside. This can be seen in FIG. 35. Then the target 43, enclosed within the tissue core that is located within the excision device 160 can be delivered to a specimen collection vessel, Petri dish or other receptacle for ex vivo testing and analysis, such as pathological or microbiological analysis.

Figure 35:
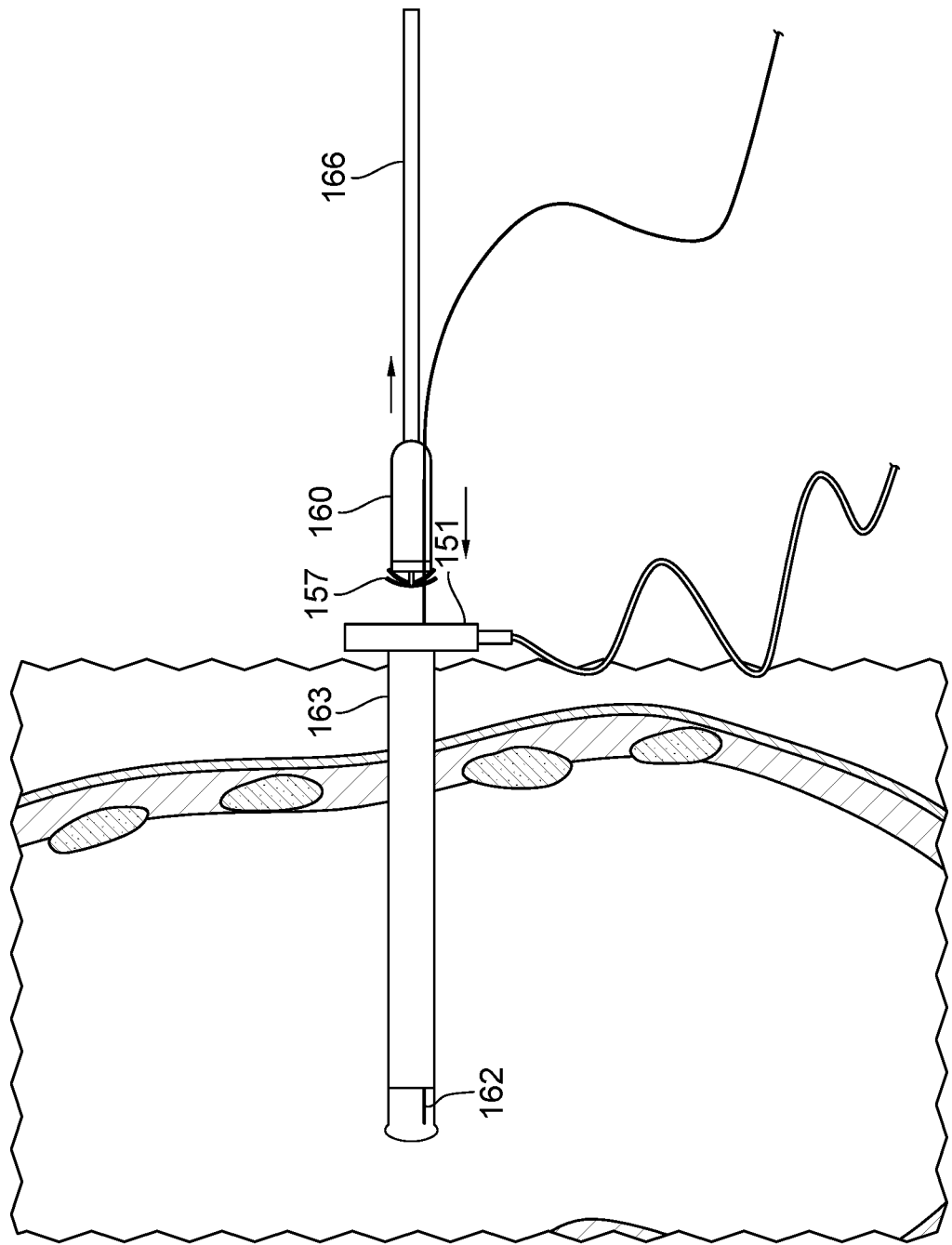
Figure 36:
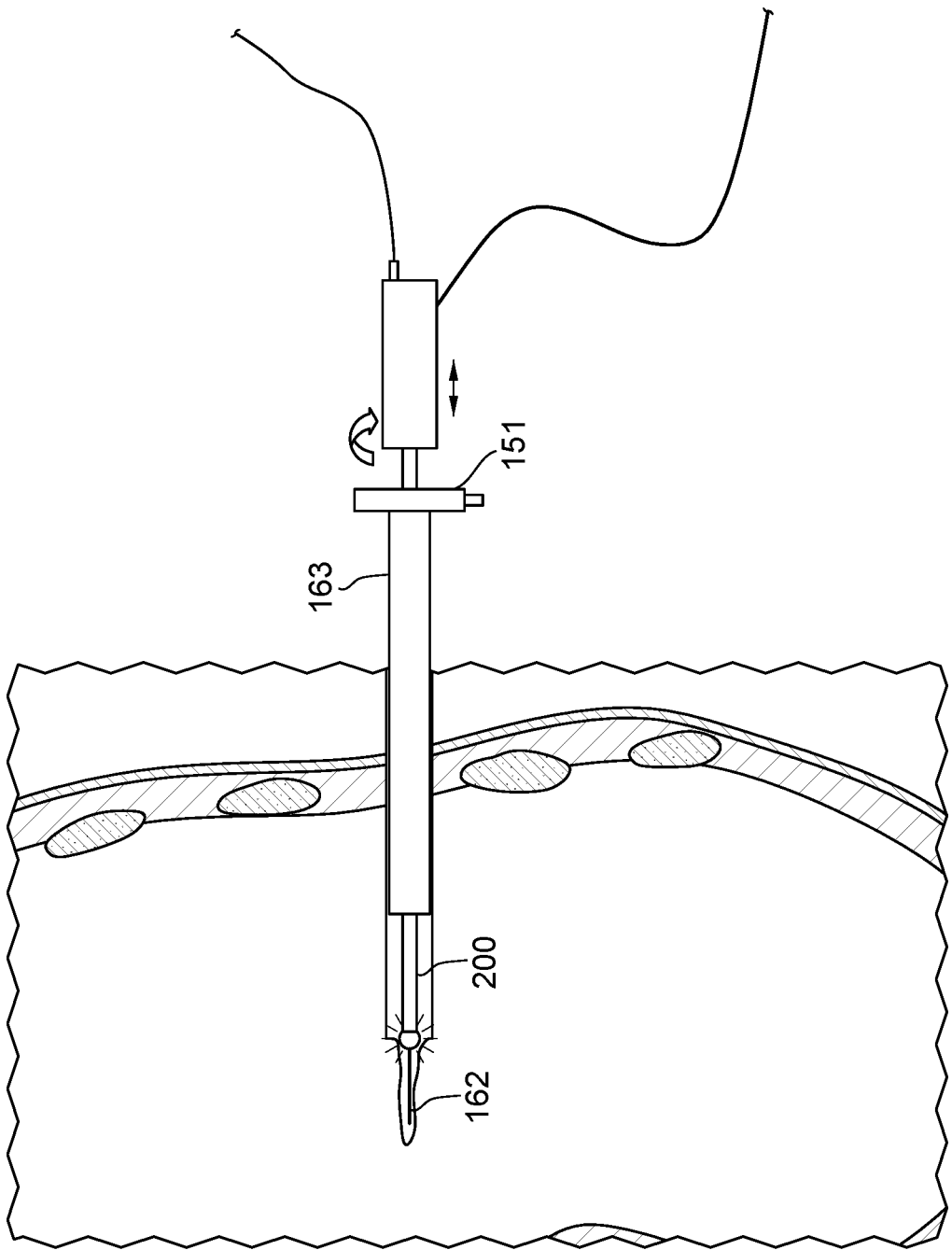

After the target tissue 43 is excised, a sealing guidewire 162 can be passed through the channel or tissue tract (e.g. through the tubular member 163 of the working port 151 if still in place), until its proximal end reaches the vicinity from which the target tissue 43 was excised, as shown in FIGS. 35 and 36. A sealing device 200 is then advanced over the sealing guidewire 162. In another embodiment, the sealing device 200 is advanced over the needle 154 that was advanced through the pleura and maintained in place to serve as a guide for the sealing device 200. The vacuum provided at the aperture(s) 153 of the working port 151 (if present), in addition to maintaining negative pressure in the pleural space or within the parenchymal track through the lung to prevent lung collapse from air leak or bleeding, also draws the tissue tract against the sealing device 200 to facilitate uniform, robust sealing. The sealing device 200 comprises a proximal tip that can impart energy to facilitate sealing, such as thermal energy, electrical energy, RF or from a laser. Examples include, but are not limited to, a diode laser, a laser of any of a number of frequencies designed to impart heat to the surrounding tissue that seals the tract. Another example includes a proximal tip comprising a cryogenic mechanism adapted to seal the tract using cryoablation. Further examples provide a sealing device 200 that utilizes steam/vapor or microwave sealing. The sealing device 200 is actuated and pulled back towards the operator to initiate sealing the tract. If a fixed-diameter sleeve (such as the tubular member 163 of the working port 151) is present, then the proximal end of the sealing device 200 is advanced beyond the proximal end of that sleeve, and both can be withdrawn together. In this manner, as the sleeve is withdrawn exposing fresh tissue, the proximal end of the sealing device 200 arrives at and supplies energy to that tissue to cauterize it. This procedure may be followed until the entire assembly has been withdrawn and the entire length of the tissue tract cauterized or sealed. The energy is imparted to the surrounding tissue tract as the sealing device 200 cauterizes (e.g. burns and seals) that tissue, preventing the egress of blood or air.

In another embodiment, fluid can be expelled through the proximal end of the sealing device 200 as it is withdrawn. Example fluids that can be expelled through the proximal end of the sealing device 200 include: natural/biological adhesives (such as polypeptide/protein-based adhesives, fibrin-based adhesives, gelatin-based adhesives, collagen-based adhesives, albumin-based adhesives, polysaccharide-based adhesives, chitosan-based adhesives, human blood-based adhesives, and animal-based adhesives) and synthetic and semi-synthetic adhesives (such as cyanoacrylates, polyethylene glycol hydrogels, urethane-based adhesives, and other synthetic adhesives). The fluid can fill the volume of the tract and can be heated with RF energy (e.g. wet electrode) or laser beyond the temperature of the surrounding tissue, to a temperature sufficient to cauterize and seal the surrounding tissue. The combination of the fluid and the RF seals the surrounding tissues and prevents the leakage of blood, air, lymph tissue, etc.

After the tract has been sealed, the wound is assessed for bleeding or air leakage. If a leak is found, the tract can be retreated, or alternatively a chest tube can be inserted to drain fluid from the pleural space surrounding the lung and/or from the chest outside the pleura. Advantageously, the chest tube may be inserted in the already extant tract, thus eliminating the need to introduce an additional wound to the patient. The chest tube can be left in the tract and attached to a suction apparatus to provide suction to the lung and pull the tissue in close apposition to the chest tube in the conventional manner. Over a period of time, as the tract heals and internal bleeding subsides, the chest tube can be removed in the conventional manner and the wound dressed.

In an embodiment, a carbon dioxide sensor is positioned within or in communication with the working port 151 during the entire procedure to sample gas/liquid within the pleural space to determine if air containing carbon dioxide is leaking out of the cut surface of the tract in real time. In this embodiment such a $CO_2$ sensor can provide an indication if the lung has been nicked and is therefore leaking air, or if the operative puncture through the lung to reach the operative site adjacent the target tissue 43 has not been completely or properly sealed.

In an alternative method, an excision device 160 can be advanced over the inflated dilation catheter 159, as shown in FIGS. 30 and 31 to excise the target tissue located proximally of the inflated dilation catheter 159. In this embodiment the excision device 160 can take the form of the working port 151 above described, but with tubular member 163 of the working port 151 configured to core out a plug of tissue via simultaneous advancement and rotation through the tissue. That is, the working port 151 serves as the excision device to core out the target tissue beyond the inflated dilation catheter. To excise the target tissue 43, the excision device 160/working port 151 is advanced until its sharpened edge 167 arrives adjacent the target tissue 43. Preferably the diameter of its tubular member 163 has been selected to accommodate at least a portion of the target tissue 43, more preferably the full dimensions of the target tissue 43 as well as some surrounding tissue. Upon arriving adjacent the target tissue 43, the excision device 160/working port 151 can be alternately rotated clockwise and counterclockwise from outside the body, while simultaneously pressing it forward toward the target tissue 43 against the counterforce applied thereto by tensioning the catch wire 156. By this operation, the sharpened edge 167 makes a circular slice of the tissue surrounding the target tissue 43, and is advanced over the target tissue 43 through that slice, preferably until its proximal sharpened edge 167 reaches the tissue anchor 157. At that point the excision device 160/working port 151 has cored out the target tissue 43 as well as some surrounding tissue, with the core located within the tubular member 163. The target tissue 43 then is excised and removed from the body by simultaneously withdrawing both the catch wire 156 and the excision device 160/working port 151 through the tissue tract and through the opening in the chest wall to the outside. As will be appreciated, in this embodiment the dilation catheter 159 also should be withdrawn in tandem with the withdrawal of the working port 151 acting as the excision device, in order to permit the core of target tissue 43 therein to be withdrawn distally through the tissue tract. To achieve this the dilation catheter 159 can be deflated, slightly or completely, to facilitate its withdrawal together with the working port 151 and the core of target tissue 43 beyond the dilation catheter 159 proximal end. A sealing device 200 may thereafter be inserted into the tissue tract, optionally along or over the needle if it has remained in place since the beginning of the procedure, and then actuated to seal the tract upon withdrawal thereof in the manner above described. The target 43, enclosed within the tissue core that is located within the tubular member 163 can be delivered to a specimen collection vessel, Petri dish or other receptacle for ex vivo testing and analysis, such as pathological or microbiological analysis.

Figure 37:
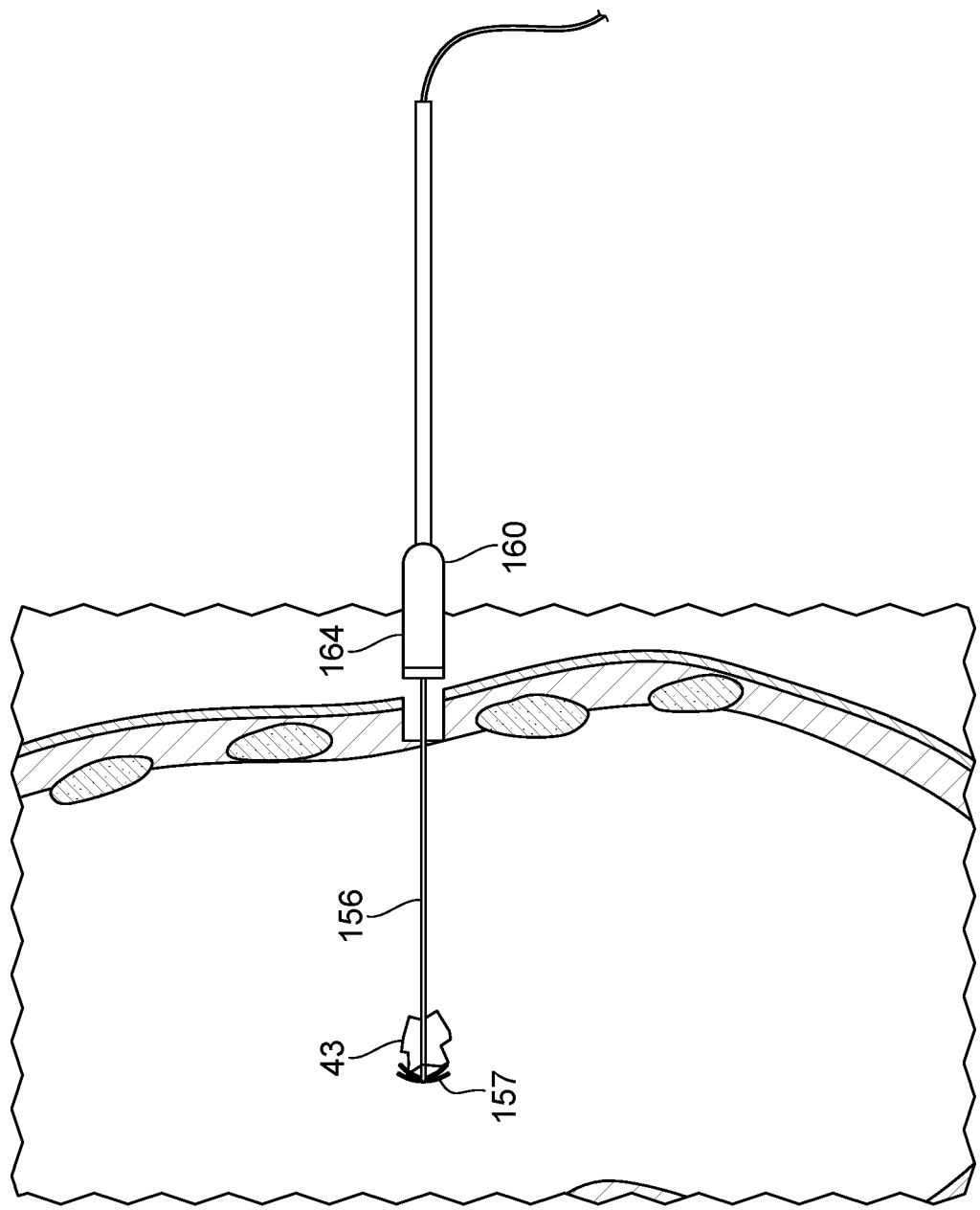

In another embodiment, rather than advancing a dilation catheter 159 through the working port 151 and over the catch wire 156 as illustrated in FIG. 28, the excision device 160 is advanced directly over the catch wire 156, until it reaches the target tissue 43 as shown in FIG. 37. To facilitate this the excision device 160 includes a central bore through which the catch wire 156 can pass in order to guide the excision device 160 through the tissue tract to the target tissue. The excision device 160 is advanced against the distal counterforce exerted against the target tissue 43 from behind by tensioning the catch wire 156, which is fixed to the target tissue 43 by the tissue anchor 157. This prevents the target tissue 43 from being pushed further into the patient by advancement of the excision device 160, possibly toward larger vascular or airway structures. It also fixes the target tissue 43 in place to assist in the subsequent coring step, as described regarding FIGS. 32-35.

Figure 38:
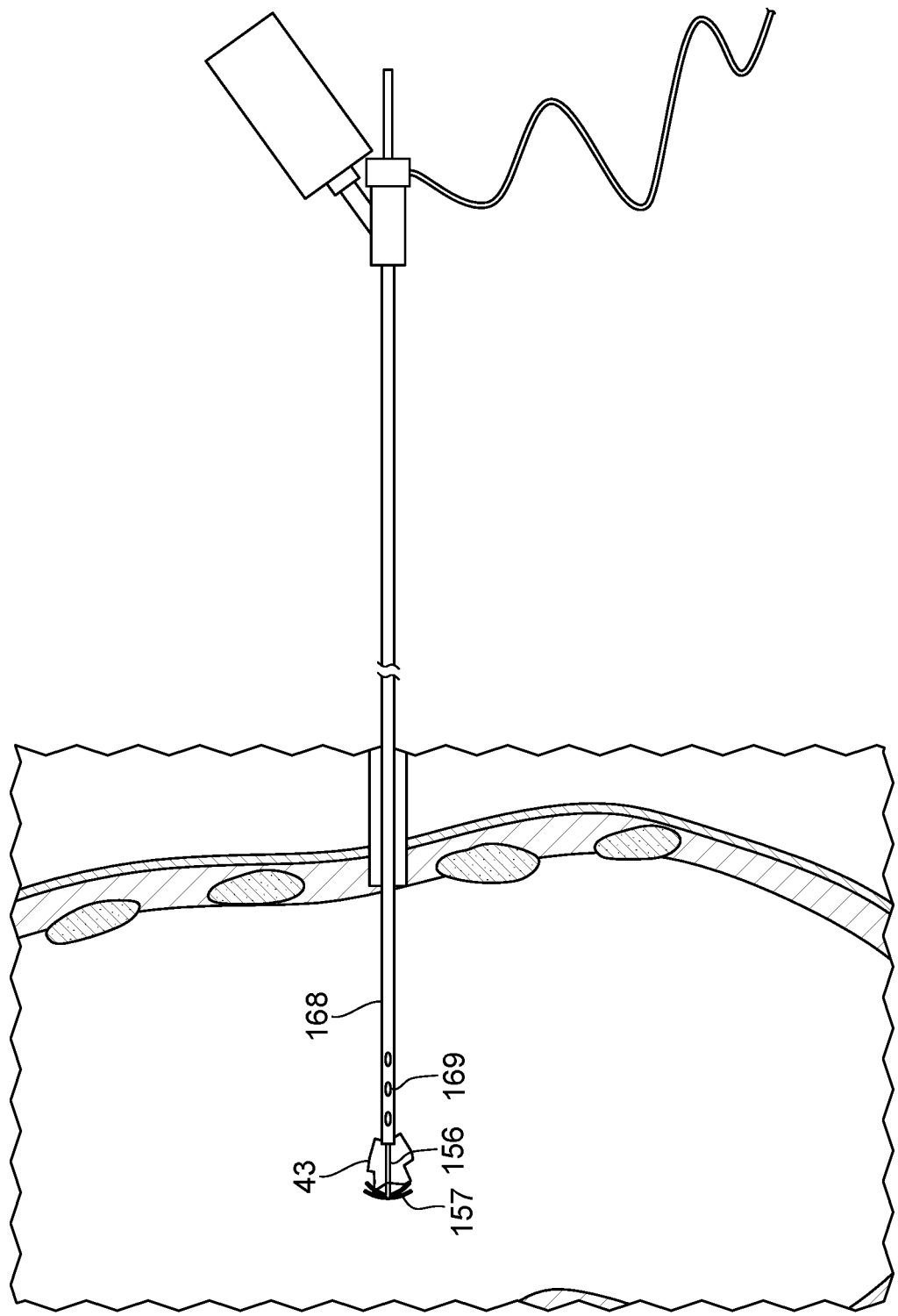

In another embodiment, after the catch wire 156 is anchored from behind the target tissue 43 via the tissue anchor 157, a suction catheter 168 can be advanced over the catch wire 156, as illustrated in FIG. 38. The suction catheter 168 can be advanced against the counterforce applied to the target tissue 43. The suction catheter 168 is a hollow tubular member having a proximal end with one or more apertures 169. A distal end of the suction catheter 168 is in communication with a vacuum source. The suction catheter 168 is of a predetermined length such that the proximal end can extend into the chest, e.g. within the pleural space and through the lung up to the target tissue 43, when inserted through the opening in the chest wall and the distal end resides outside of the body. The inner diameter of the suction catheter 168 is greater than the outer diameter of the catch wire 156. The vacuum source coupled to the distal end of the suction catheter 168 resides outside of the body, and is effective to draw a vacuum on the suction catheter 168. The resulting vacuum drawn through the aperture(s) 169 therein maintains a negative pressure within the chest to keep the lungs fully expanded during an operation, and further pulls the lung tract down toward the suction catheter 168. This suction allows the removal of blood, fluid, and air that could otherwise collapse the lung away from the chest wall (i.e. prevent an intra procedural hemopneumothorax). In one embodiment, the vacuum drawn through the aperture(s) 169 is −5 cmH$_2$O to −100 cmH$_2$O. With the suction catheter 168 in place, the remaining steps (dilation of tract with the dilation catheter 159, excision of target tissue 43 with the excision device 160, and sealing of the tract with the sealing device 200) can be performed while vacuum is maintained within the tissue tract.

Figures 39, 40:
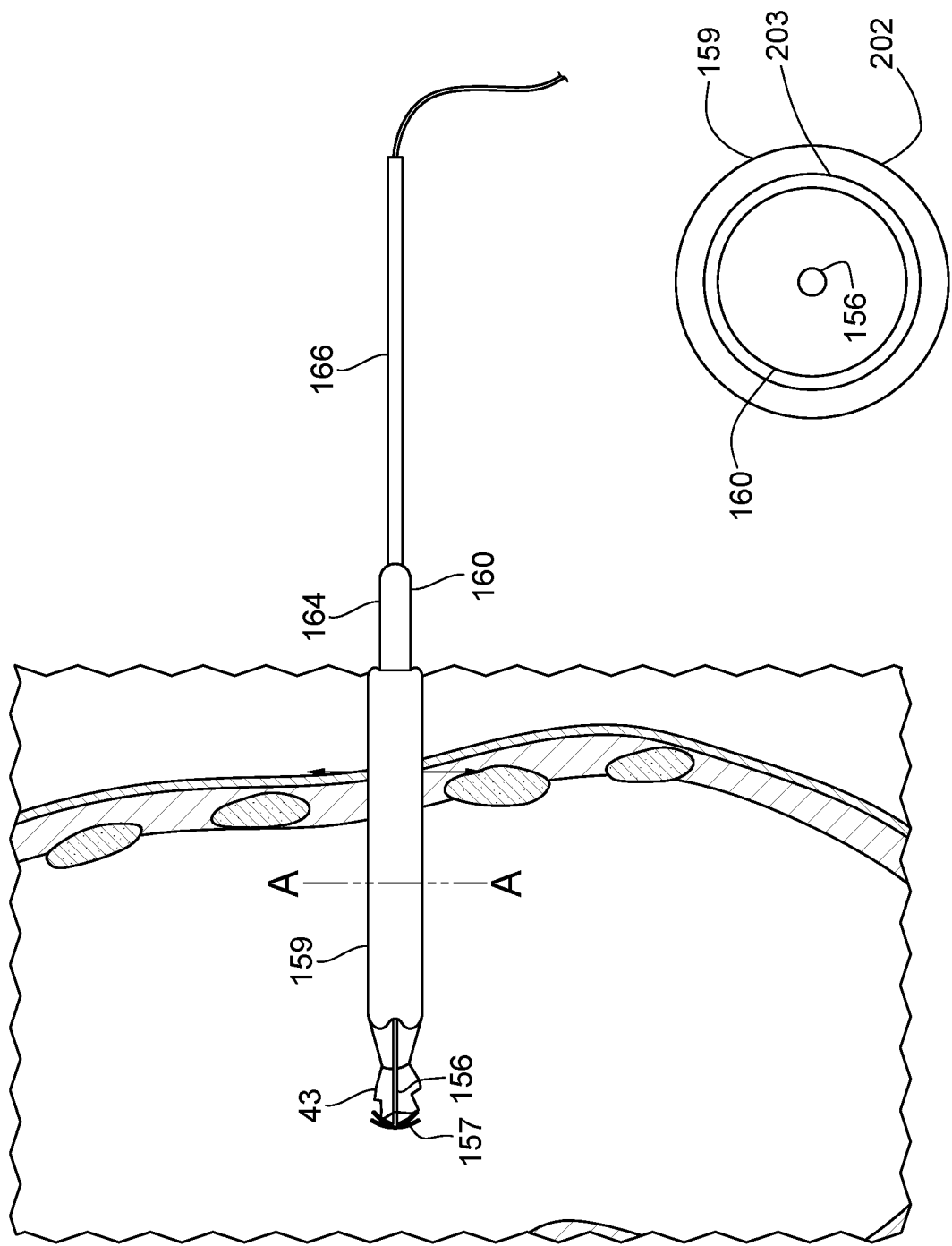

In another embodiment, the dilation catheter 159 with an elongated toroidal configuration is advanced over the catch wire 156 in a deflated state against a counterforce applied by tensioning the catch wire 156 in a distal direction from outside the chest, as shown in FIGS. 39 and 40. The dilation catheter 159 is advanced through the pleural space and into the lung over the catch wire 156, up to the target tissue 43 positioned adjacent the tissue anchor 157. The dilation catheter 159 can be a balloon catheter that extends at least from the chest wall through the pleural space and into the lung, up to the target tissue 43 along the tract followed by the catch wire 156. The dilation catheter 159 in FIG. 39 is illustrated as including concentric first (outer) and second (intermediate) tubes 202 and 203, respectively, as shown in the cross-section of line A-A and FIG. 40. When the dilation catheter 159 is inflated the first and second tubes 202 and 203 have constant diameters and define therebetween an annular space such that the dilation catheter 159 has the form of an elongated toroid whose volume is a ring-shaped cylindrical projection defined between the first tube 202 and the second tube 203. Preferably one or both of the tubes 202 and 203 (preferably at least the outer tube 202) is/are formed a part of the continuous flexible wall of the dilation catheter 159, such that it is ordinarily collapsed or collapsible when the catheter 159 is not inflated, and attains its expanded, fixed diameter as shown in FIG. 40 only upon inflation of the catheter 159 with inflation fluid. In this embodiment a channel is formed at the center of the dilation catheter 159 extending along its length. The catch wire 156 extends through the channel of the dilation catheter 159. Once the dilation catheter has been inserted and dilated, the excision device 160 can be advanced through the channel over the catch wire 156, until it reaches the target tissue 43. The excision device 160 is advanced against the distal counterforce exerted against the target tissue 43 from behind by tensioning the catch wire 156, which is fixed to the target tissue 43 by the tissue anchor 157. This prevents the target tissue 43 from being pushed further into the patient by advancement of the excision device 160, possibly toward larger vascular or airway structures. It also fixes the target tissue 43 in place to assist in the subsequent coring step, as described regarding FIGS. 32-35. Upon reaching the target tissue the excision device 160 can be actuated to core out the target tissue or a part thereof, and withdrawn as disclosed for preceding embodiments. Thereafter, a sealing device 200 as previously described can be inserted through the channel in order to seal the tract upon deflation and withdrawal of the dilation catheter 159, preferably in tandem with actuation and withdrawal of the sealing device 200 at a location just beyond the proximal end of the deflated dilation catheter 159. As will be appreciated, this embodiment will be effective only if the target tissue to be excised (or that portion thereof that is to be excised) is small enough to fit through the channel at the center of the dilation catheter. That size can be determined ahead of time via CT fluoroscopy or other appropriate technique as noted above, so that a properly sized dilation catheter 159 can be selected for the procedure.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A method of excising a target tissue, comprising:
dilating a tissue tract that extends from an opening in a body wall toward a target tissue;
advancing a catch wire through said tissue tract until an end of the catch wire is positioned adjacent or beyond the target tissue;
anchoring the catch wire from a location adjacent the target tissue;
advancing an excision device toward the target tissue, over the catch wire and against a counterforce applied by tensioning the catch wire; and
applying suction to said excision device in order to draw suction within a pleural space of a patient effective to maintain a negative pressure therein in order to prevent collapse of the patient's lung while excising said target tissue.

2. The method of claim 1, comprising tensioning said catch wire from a tissue anchor against the target tissue.

3. The method of claim 1, the excision device comprising a circumferential cutting edge.

4. The method of claim 3, further comprising making a slice in the tissue surrounding the target tissue via the cutting edge, and advancing the excision device over the target tissue through the slice until said target tissue is located within a hollow sleeve of said excision device.

5. The method of claim 4, further comprising simultaneously withdrawing both the catch wire and the excision device through the tissue tract.

6. The method of claim 4, further comprising withdrawing the excision device through the tissue tract.

7. The method of claim 1, further comprising sealing the tissue tract.

8. The method of claim 1, further comprising dilating said tissue tract via inflation of a dilation catheter, and inserting a fixed-diameter sleeve over the inflated dilation catheter to provide a fixed-diameter passageway along the tissue tract prior to advancement of the excision device.

9. The method of claim 1, further comprising: advancing a sealing device through the tissue tract to a vicinity from which the target tissue was excised, and simultaneously actuating and withdrawing the sealing device to seal the tissue tract.

10. A method of excising a target tissue, comprising:
tensioning a catch wire from a location adjacent a target tissue within a patient;
dilating a tissue tract within the patient that extends toward the target tissue;
advancing an excision device through the tissue tract over the catch wire and against a counterforce applied by tensioning the catch wire, thereby coring tissue surrounding the target tissue;
withdrawing the excision device having the target tissue disposed therein through the tissue tract;
applying suction to said excision device in order to draw suction within a pleural space of the patient effective to maintain a negative pressure therein in order to prevent collapse of the lung while coring said target tissue.

11. The method of claim 10, comprising coring said tissue surrounding the target tissue via a circumferential cutting edge, and thereafter advancing a hollow sleeve of said excision device over the target tissue until the target tissue is located within the sleeve.

12. The method of claim 10, further comprising sealing the tissue tract.

13. An apparatus for excising a target tissue, the apparatus comprising:
a catch wire with a tissue anchor at an end thereof, the catch wire configured to be tensioned by engaging the tissue anchor against the target tissue and pulling the catch wire away from the target tissue; and
an excision device comprising a hollow sleeve configured and dimensioned to be advanced over the catch wire,
wherein the excision device is configured such that when suction is applied to the excision device, suction is drawn within a pleural space of a patient effective to maintain a negative pressure therein in order to prevent collapse of the patient's lung while excising said target tissue.

14. The apparatus according to claim 13, further comprising an inflatable dilation catheter configured to dilate a tissue tract that extends toward the target tissue.

15. The apparatus according to claim 14, the dilation catheter being configured to be inserted into a tissue tract over and along the catch wire.

16. The apparatus according to claim 14, wherein the hollow sleeve terminates in a circumferential cutting edge.

17. The apparatus according to claim 14, the apparatus further comprising a fixed-diameter sleeve configured to be inserted over the inflated dilation catheter to provide a fixed-diameter passageway along the tissue tract to accommodate the excision device.

18. The apparatus according to claim 13, the apparatus being configured such that both the catch wire and the excision device are simultaneously withdrawable through a tissue tract within a patient.

* * * * *